US006624139B1

(12) United States Patent
Wei et al.

(10) Patent No.: US 6,624,139 B1
(45) Date of Patent: Sep. 23, 2003

(54) HYPERSENSITIVE RESPONSE ELICITOR-INDUCED STRESS RESISTANCE

(75) Inventors: Zhong-Min Wei, Kirkland, WA (US); Richard L. Schading, West Melbourne, FL (US)

(73) Assignee: Eden Bioscience Corporation, Bothell, WA (US)

( * ) Notice: Subject to any disclaimer, the term of this patent is extended or adjusted under 35 U.S.C. 154(b) by 0 days.

(21) Appl. No.: 09/431,614

(22) Filed: Nov. 2, 1999

Related U.S. Application Data

(60) Provisional application No. 60/107,243, filed on Nov. 5, 1998.

(51) Int. Cl.$^7$ .......................... A01N 37/18; A61K 35/66; C12N 15/31

(52) U.S. Cl. ............................ 514/2; 514/12; 530/350; 536/23.7; 435/847; 435/874; 435/910; 424/93.5; 424/93.4; 800/298; 800/307; 800/314; 800/317.1; 800/323.1; 800/317.4

(58) Field of Search ................................. 800/298, 307, 800/314, 317.1, 317.4, 323.1, 323.2, 323.3; 424/93.5, 93.4; 514/2, 12; 435/847, 874, 910; 536/23.7; 530/350

(56) References Cited

U.S. PATENT DOCUMENTS

| | | |
|---|---|---|
| 4,569,841 A | 2/1986 | Liu |
| 4,597,972 A | 7/1986 | Taylor |
| 4,601,842 A | 7/1986 | Caple et al. |
| 4,740,593 A | 4/1988 | Gonzalez et al. |
| 4,851,223 A | 7/1989 | Sampson |
| 4,886,825 A | 12/1989 | Ruess et al. |
| 4,931,581 A | 6/1990 | Schurter et al. |
| 5,057,422 A | 10/1991 | Bol et al. |
| 5,061,490 A | 10/1991 | Paau et al. |
| 5,135,910 A | 8/1992 | Blackburn et al. |
| 5,173,403 A | 12/1992 | Tang |
| 5,217,950 A | 6/1993 | Blackburn et al. |
| 5,243,038 A | 9/1993 | Ferrari et al. |
| 5,244,658 A | 9/1993 | Parke |
| 5,260,271 A | 11/1993 | Blackburn et al. |
| 5,348,743 A | 9/1994 | Ryals et al. |
| 5,494,684 A | 2/1996 | Cohen |
| 5,523,311 A | 6/1996 | Schurter et al. |
| 5,550,228 A | 8/1996 | Godiard et al. |
| 5,552,527 A | 9/1996 | Godiard et al. |
| 5,708,139 A | 1/1998 | Collmer et al. |
| 5,850,015 A | 12/1998 | Bauer et al. |
| 6,001,959 A | 12/1999 | Bauer et al. |

FOREIGN PATENT DOCUMENTS

| | | |
|---|---|---|
| EP | 0 612 848 A3 | 2/1994 |
| WO | WO 93/23532 | 11/1993 |
| WO | WO 94/01546 | 1/1994 |
| WO | WO 94/26782 | 11/1994 |
| WO | WO 95/19443 | 7/1995 |
| WO | WO 96/39802 | 12/1996 |
| WO | WO 98/15547 | 4/1998 |
| WO | WO 98/24297 | 6/1998 |
| WO | WO 98/32844 | 7/1998 |
| WO | WO 98/37752 | 9/1998 |
| WO | WO 98/54214 | 12/1998 |
| WO | WO 99/07206 | 2/1999 |
| WO | WO 99/07207 | 2/1999 |

OTHER PUBLICATIONS

US 5,650,387, 7/1997, Wei et al. (withdrawn)
Collmer et al., "*Erwinia chysanthemi* and *Pseudomonas syringae*: Plant Pathogens Trafficking in Extracellular Virulence Proteins," pp. 43–78.
Frederick et al., "The WTS Water–Soaking Genes of *Erwinia stewartii* are Related to hrp Genes," Seventh International Symposium on Molecular Plant Microbe Interactions, Abstract No. 191 (Jun. 1994).
Wei et al., "Proteinaceous Elicitors of the Hypersensitive Response from *Xanthomonas compestris* pv. *glycines*," Seventh International Symposium on Molecular Plant Microbe Interactions, Abstract No. 244 (Jun. 1994).
Preston et al., "The HrpZ Proteins of *Pseudomonas syringae* pvs. *syringae*, *glycinea*, and *tomato* are Encoded by an Operon Containing *Yersinia ysc* Homologs and Elicit the Hypersensitive Response in Tomato but not Soybean," *Mol. Plant–Microbe Interact.*, 8(5):717–32 (1995).
Bauer et al., "*Erwinia chrysanthemi* hrp Genes and their Involvement in Elicitation of the Hypersensitive Response in Tobacco," Sixth International Symposium on Molecular Plant Microbe Interactions, Abstract No. 146 (Jul. 1992).
Stryer, L., "Enzymes are Highly Specific," *Biochemistry*, San Francisco; W.H. Freeman and Company, p. 116 (1975).
Keen et al., "Inhibition of the Hypersensitive Reaction of Soybean Leaves to Incompatible Pseudomonas spp. by Blasticidin S, Streptomycin or Elevated Temperature," *Physiological Plant Pathology*, 18:325–337 (1981).
Lerner, R.A., "Tapping the Immunological Repertoire to Produce Antibodies of Predetermined Specificity," *Nature*, 299:592–96 (1982).
Staskawicz et al., "Cloned Avirulence Gene of *Pseudomonas Syringae* pv. *glycinea* Determines Race–specific Incompatibility on *Glycine max* (L.) Merr.," *Proc. Natl. Acad. Sci. USA*, 81:6024–28 (1984).

(List continued on next page.)

Primary Examiner—Christopher S. F. Low
Assistant Examiner—Chih-Min Kam
(74) Attorney, Agent, or Firm—Nixon Peabody LLP

(57) ABSTRACT

The present invention is directed to imparting stress resistance to plants. This can be achieved by applying a hypersensitive response elicitor in a non-infectious form to plants or plant seeds under conditions effective to impart stress resistance to plants or plants grown from the plant seeds. Alternatively, transgenic plants or plant seeds transformed with a DNA molecule encoding the elicitor can be provided and the transgenic plants or plants resulting from the transgenic plant seeds are grown under conditions effective to impart stress resistance to plants or plants grown from the plant seeds.

14 Claims, No Drawings

OTHER PUBLICATIONS

Bauer et al., "*Erwinia chrysanthemi* Harpin$_{Ech}$: An Elicitor of the Hypersensitive Response that Contributes to Soft–Rot Pathogenesis," *MPMI*, 8(4):484–91 (1995).

Huang et al., "Characterization of the hrp Cluster from *Pseudomonas syringae* pv. *syringae* 61 and TnphoA Tagging of Genes Encoding Exported or Membrane–Spanning Hrp Proteins," *Molec. Plant–Microbe Interact.*, 4(5):469–76 (1991).

Huang et al., "The *Pseudomonas syringae* pv. *syringae* 61 hrpH Product, an Envelope Protein Required for Elicitation of the Hypersensitive Response in Plants," *J. Bacteriol.*, 174(21):6878–85 (1992).

Bonas, U., "hrp Genes of Phytopathogenic Bacteria," *Current Topics in Microbio.*, 192:79–98 (1994).

Arlat et al., "PopA1, A Protein Which Induces a Hypersensitivity–Like Response on Specific Protein Petunia Genotypes, is Secreted via the Hrp Pathway of *Pseudomonas solanacearum*," *The EMBO J.*, 13(3):543–53 (1994).

Kessmann et al., "Induction of Systemic Acquired Disease Resistance in Plants By Chemicals," *Ann. Rev. Phytopathol.*, 32:439–59 (1994).

Kelman, A., "The Relationship of Pathogenicity in *Pseudomonas solanacearum* To Colony Appearance on a Tetrazolium medium," *Phytopathology*, 44:693–95 (1954).

Winstead et al., "Inoculation Techniques For Evaluating Resistance to *Pseudomonas solanacearum*," *Phytopathology*, 42:628–95 (1952).

Ahl et al., "Iron Bound–Siderophores, Cyanic Acid, and Antibodies Involved in Suppression of *Thielaviopsis basiocola* by a *Pseudomonas fluorescens* Strain," *J. Phytopathology*, 116:121–34 (1986).

Anderson et al., "Responses of Bean to Root Colonization with *Pseudomonas putida* in a Hydroponic System," *Phytopathology*, 75(9):992–95 (1985).

Gardner et al., "Growth Promotion and Inhibition by Antibiotic–Producing Fluorescent Pseudomonads on Citrus Roots," *Plant an Soil*, 77:103–13 (1984).

Kloepper, J.W., "Effect of Seed Piece Inoculation with Plant Growth–Promoting Rhizobacteria on Populations of *Erwinia carotovora* on Potato Roots and In Daughter Tubers," *Phytopathology*, 73(2):217–19 (1983).

Atkinson et al., "The Hypersensitive Reaction of Tobacco to *Pseudomonas syringae* pv. *pisi*," *Plant Physiology*, 79:843–47 (1985).

Huynh et al., "Bacterial Blight of Soybean: Regulation of a Pathogen Gene Determining Host Cultivar Specificity," *Science*, 245:1374–77 (1986).

Kloepper et al., "Plant Growth–Promoting Rhizobacteria on Canola (Rapeseed)," *Plant Disease*, 72(1):42–6 (1988).

Kloepper et al., "Enhanced Plant Growth by Siderophores Produced by Plant Growth–Promoting Rhizobacteria," *Nature*, 286:885–86 (1980).

Kloepper et al., "Pseudomonas Siderophores: A Mechanism Explaining Disease–Suppressive Soils," *Current Microbiology*, 4:317–20 (1980).

Kloepper et al., "Emergence–Promoting Rhizobacteria: Description and Implications for Agriculture," In: *Iron, Siderophores, and Plant Disease*, Swinborne (ed.), Plenum, NY, 155–64 (1986).

Kloepper et al., "Relationship of in vitro Antibiosis of Plant Growth–Promoting Rhizobacteria to Plant Growth and the Displacement of Root Microflora," *Phytopathology*, 71(10):1020–24 (1981).

Kloepper et al., "Effects of Rhizosphere Colonization by Plant Growth–Promoting Rhizobacteria on Potato Plant Development and Yield," *Phytopathology*, 70(11):1078–82 (1980).

Kloepper et al., "Plant Growth Promotion Mediated by Rhizobacteria Bacterial Colonizers," In: *The Rhizosphere and Plant Growth*, 315–32, Keister et al. (eds), pp. 315–26 (1991).

Lifshitz et al., "Growth Promotion of Canola (rapeseed) Seedlings by a Strain of *Pseudomonas putida* Under Gnotobiotic Conditions," Conditions, *Microbiol.* 33:390–95 (1987).

Liu et al., "Induction of Systemic Resistance in Cucumber Against Bacterial Angular Leaf Spot by Plant Growth Promoting Rhizobacteria," *Phytopathology*, 85(8):843–47 (1995).

Loper et al., "Influence of Bacterial Sources of Indole–3–acetic Acid on Root Elongation of Sugar Beet," *Phytopathology*, 76(4):386–89 (1986).

Schroth et al., "Disease–Suppressive Soil and Root–Colonizing Bacteria," *Science*, 216:1376–81 (1982).

Stutz et al., "Naturally Occurring Fluorescent Pseudomonads Involved Suppression of Black Root Rot of Tobacco," *Phytopathology*, 76(2):181–85 (1986).

Lindgren et al., "Gene Cluster of *Pseudomonas Syringae* pv. "*phaseolicola*" Controls Pathogenicity of Bean Plants and Hypersensitivity on Nonhost Plants," *J. Bacteriol.*, 168(2):512–22 (1986).

Bauer et al., "Cloning of a Gene from *Erwinia Amylovora* Involved in Induction of Hypersensitivity and Pathogenicity," *Plant Pathogenic Bacteria*, Proceedings of the Sixth International Conference on Plant Pathogenic Bacteria, Maryland, pp. 425–29 (1987).

Wei et al., "Induction of Systemic Resistance of Cucumber to *Colletotrichum orbiculare* by Select Strains of Plant Growth–Promoting Rhizobacteria," *Phytopathology*, 81:1508–12 (1991).

Wei et al., "Induction of Systemic Resistance with Seed Treatment by PGPR Strains," pp. 191–194.

Weller, D.M., "Biological Control of Soilborne Plant Pathogens in the Rhizosphere with Bacteria," *Ann. Rev. Phytopathol.*, 26:379–407 (1988).

Young et al., "PGPR: Is There a Relationship Between Plant Growth Regulators and the Stimulation of Plant Growth or Biological Activity?," pp. 182–186 (1991). Organisation International De Lutte Biologique et integree Centre les Animauex et les Plantes Nursibles, Paris, France.

Wei, et al., "Induced Systemic Resistance by Select Plant Growth–Promoting Rhizobacteria Against Bacterial Wilt of Cucumber and the Beetle Vectors," *Phytopathology*, 86:1154, Abstract No. 313 (1995).

Wieringa–Brants et al., Induced Resistance in Hypersensitive Tobacco Against Tobacco Mosaic Virus by Injection of Intercellular Fluid from Tobacco Plants with Systemic Acquired Resistance, *Phytopathology*, 118:165–70 (1987).

Malamy et al., "Salicylic Acid: A Likely Endogenous Signal in the Resistance Response of Tobacco to Viral Infection," *Science*, 250:1003–04 (1990).

Dean et al., "Immunisation Against Disease: The Plant Fights Back," pp. 383–411. Symposium series—British mycological Society, 1987, vol. 13.

Cameron et al., "Biologically Induced Systemic Acquired Resistance in *Arabidopsis thaliana*," *The Plant Journal*, 5(5):715–25 (1994).

Laby et al., "Structural and Functional Analysis of *Erwinia amylovora* Harpin, An Elicitor of the Plant Hypersensitive Response," *Phytopathology*, 84:345 (1994).

Van Gijsegem et al., "Evolutionary Conversation of Pathogenicity Determinants Among Plant and Animal Pathogenic Bacteria," *Trends Micorbiol.*, 1:175–80 (1993).

Kamoun, et al., "Extracellular Protein Elicitors from Phytophthora: Host Specificity and Induction of Resistance to Bacterial and Fungal Phytopathogens," *Molecular Plant–Microbe Interactions*, 6(1):15–25 (1993).

Baillieul, et al., "A New Elicitor of the Hypersensitive Response in Tobacco: A Fungal Glycoprotein Elicits Cell Death, Expression of Defense Genes, Production of Salicylic Acid, and Induction of Systemic Acquired Resistance," *The Plant Journal*, 8(4):551–60 (1995).

Collings et al., "Plant Gene Expression in Response to Pathogens," *Plant Molecular Biology*, 9:389–410 (1987).

Shatzman et al., "Expression, Identification, and Characterization of Recombinant Gene Products in *Escherichia coli*," *Methods in Enzymology*, 152:661–73 (1987).

Tenhaken, et al., "Function of the Oxidative Burst in Hypersensitive Disease Resistance," *Proc. Natl. Acad. Sci. USA*, 92:4158–63 (1995).

Bonnet, et al., "Induction de nécroses foliaries, de protéines b et de résistance dans les interactions tabac Phytophthora," *Agronomie*, 6(9):829–37 (1986).

Gallitelli, et al., "Satellite–Mediated Protectin of Tomato Against Cucumber Mosaic Virus: II. Field Test Under Natural Epidemic Conditions in Southern Italy," *Plant Disease*, 75(1):93–5 (1991).

Kang et al., "Control of Tomato Disease by Interference by Interference of an Attenuated Virus," *Res. Rept. RDA (Hort.)*, 27(1):17–26 (1985).

Montasser, et al., "Satellite–Mediated Protection of Tomato Against Cucumber Mosaic Virus: I. Greenhouse Experiments and Simulated Epidemic Conditions in the Field," *Plant Disease*, 75(1):86–92 (1991).

Marks, R.J., "Varietal Resistance to Potato Cyst Nematode," *Agricultural Entomology*, pp. 63–67 (1979).

Walton, et al., "Host–Selective Toxins and Disease Specificity: Perspectives and Progress," *Annu. Rev. Phytopathol.*, 31:275–303 (1993).

Atkinson, M.M., "Molecular Mechanisms of Pathogen Recognition by Plants," *Advances in Plant Pathology*, 10:36–64 (1993).

Godiard, et al., "Differential Regulation in Tobacco Cell Suspensions of Genes Involved in Plant–Bacteria Interactions by Pathogen–Related Signals," *Plant Molecular Biology*, 17:409–13 (1991).

Ricci, et al., "Structure and Activity of Proteins from Pathogenic Fungi Phytophthora Eliciting Necrosis and Acquired Resistance in Tobacco," *Eur. J. Biochem.*, 183:555–63 (1989).

Lakhmatova, I.T., "Induction of Plant Resistance to Viral Diseases: Application of Vaccination," *Sel'skokhozyaistvennaya Biologiya*, Biologiya 3:39–51 (1991).

*Biologicheskii Zhurnal Armenii*, 31(3):305–09 (1978).

Lakhmatova, I.T., "Using Biologically Active Substances to Induced Plant Resistance to Viruses Immunization," *Sel'skokhozyaistvennaya Biologiya*, 3:13–22 (1992).

Shields, R., "Towards Insect–Resistant Plants," *Nature*, 328:12–13 (1987).

Huang et al., "Molecular Clonin oa a *Pseudomonas syringae* pv. *syringae* Gene Cluster That Enables *Pseudomonas fluorescens* To Elicit the Hypersensitive Response in Tobacco Plants," *J. Bacteriol.*, 170(10):4758–56 (1988).

Ricci, et al., "Differential Production of Parasiticein, an Elicitor of Necrosis and Resistance in Tobacco, by Isolates of *Phytophthora Parasitica*," *Plant Pathology*, 41:298–307 (1992).

Honée, et al., "Molecular Characteristics of the Interaction Between the Fungal Pathogen *Cladosporium fulvum* and Tomato," *Advances in Molecular Genetics of Plant–Microbe Interactions*, 3:199–206 (1994).

Keller, et al., "Responses of Tobacco to Elicitins, Proteins From Phytophthora Spp. Eliciting Acquired Resistance," *Advances in Molecular Genetics of Plant–Microbe Interactions*, 3:327–32 (1994).

Keen, et al., "Bacteria Expressing Avirulence Gene D Produce a Specific Elicitor of the Soybean Hypersensitive Reaction," *Molecular Plant–Microbe Interactions*, 3(2):112–21 (1990).

Bauer, et al., "*Erwinia chrysanthemi* hrp Genes and Their Involvement in Soft Rot Pathogenesis and Elicitation of the Hypersensitive Response," *MPMI*, 7(5):573–81 (1994).

Schottens–Toma et al., "Purification and Primary Structure of a Necrosis–inducing Peptide from the Apoplastic Fluids of Tomato Infected with *Cladosporium fulvum* (syn. *Fulvia fulva*)," *Physiological and Molecular Plant Pathology*, 33:59–67 (1988).

Steinberger et al., "Creation and Complementation of Pathogenicity Mutants of *Erwinia amylovora*," *Molecular Plant–Microbe Interactions*, 1(3):135–44 (1988).

Beer et al., "The Hypersensitive Response in Elicited by *Escherichia coli* Containing a Cluster of Pathogenicity Genes From *Erwinia amylovora*," *Phytopathology*, 70(10):1156 (Abstract 169) (1989).

Hiatt et al., "Production of Antibodies in Transgenic Plants," *Nature*, 342:76–8 (1989).

Hippe et al., "In Situ Localization of a Foreign Protein in Transgenic Plants by Immunoelectron Microscopy Following High Pressure Freezing. Freeze Substitution and Low Temperature Embedding," *European Journal of Cell Biology*, 50:230–34(1989).

Huang et al., "Isolation and Purification of a Factor from *Pseudomonas solanacearum* That Induces a Hypersensitive–like Response in Potato Cells," *Molecular Plant–Microbe Interactions*, 2(3):132–38 (1989).

James et al., "Genetic Transformation of Apple (*Malus pumila* Mill.) Using a Disarmed Ti–binary Vector," *Plant Cell Reports*, 7:658–61 (1989).

Laby et al., "Cloning and Preliminary Characterization of an hrp Gene Cluster of *Erwinia amylovora*," *Phytopathology*, 79(10):1211 (Abstract 607) (1989).

Dow et al., "Extracellular Proteases from *Xanthomonas campestris* pv. Campestris, the Black Rot Pathogen," *Applied and Environmental Microbiology*, 56(10):2994–98 (1990).

Walters et al., "Gene for Pathogenicity and Ability to Cause the Hypersensitive Reaction Cloned from *Erwinia amylovora*," *Physiological and Molecular Plant Pathology*, 36:509–21 (1990).

Wu et al., "Cloning, Genetic Organization, and Characterization of a Structural Gene Encoding Bacillopeptidase F from *Bacillus subtilis*," *The Journal of Biological Chemistry*, 265(12):6845–50 (1990).

Bauer et al., "Further Characterization of an hrp Gene Cluster of *Erwinia amylovora*," *Molecular Plant–Microbe Interactions*, 4(5):493–99 (1991).

Beer et al., "The hrp Gene Cluster of *Erwinia amylovora*," *Advances in Molecular Genetics of Plant–Microbe Interactions*, 1:53–60 (1991).

Benvenuto et al., "Phytoantibodies': A General Vector for the Expression of Immunoglobulin Domains in Transgenic Plants," *Plant Molecular Biology*, 17:865–74 (1991).

Milat et al., "Physiological and Structural Changes in Tobacco Leaves Treated with Cryptogein, a Proteinaceous Elicitor From *Phytophthora cryptogea*," *Phytopathology*, 81(11):1364–68 (1991).

Ruberti et al., "A Novel Class of Plant Proteins Containing a Homeodomain with a Closely Linked Leucine Zipper Motif," *The EMBO Journal*, 10(7):1787–91 (1991).

Quigley et al., "Nucleotide Sequence and Expression of a Novel Glycine–Rich Protein Gene from *Arabidopsis thaliana*," *Plant Molecular Biology*, 17:949–52 (1991).

Van Kan et al., "Cloning and Characterization of cDNA of Avirulence Gene avr9 of the Fungal Pathogen *Cladosporium Fulvum*, Causal Agent of Tomato Leaf Mold," *Molecular Plant–Microbe Interactions*, 4(1):52–9 (1991).

Waldmann, T.A., "Monoclonal Antibodies in Diagnosis and Therapy," *Science*, 252:1657–62 (1991).

Willis et al., "hrp Genes of Phytopathogenic Bacteria," *Molecular Plant–Microbe Interactions*, 4:(2) 132–38 (1991).

Beer et al., "Are Hairpins Universal Elicitors of the Hypersensitive Response of Phytopathogenic Bacteria?," *Advances in Molecular Genetics of Plant–Microbe Interactions*, 2:281–86 (1992).

Laby et al., "Hybridization and Functional Complementation of the hrp Gene Cluster from *Erwinia amylovora* Strain Ea321 With DNA of Other Bacteria," *Molecular Plant–Microbe Interactions*, 5(5):412–19 (1992).

Sandhu, "Protein Engineering of Antibodies," *Crit. Rev. in Biotech.*, 12(5/6):437–62 (1992).

Wei et al., "Harpin, Elicitor of the Hypersensitive Response Produced by the Plant Pathogen *Erwinia amylovora*," *Science*, 257:85–8 (1992).

He et al., "*Pseudomonas syringae* pv. *syringae* Harpin$_{Pss}$: A Protein that is Secreted via the Hrp Pathway and Elicits the Hypersensitive Response in Plants," *Cell*, 73:1255–66 (1993).

Bonas, U., "Bacterial Home Goal by Harpins," *Trends in Microbiology*, 2:1–2 (1994).

Boccara, et al., "Plant Defense Elicitor Protein Produced by *Erwinia chrysanthemi*," *Mechanisms of Plant Defense Responses*, p. 166 (1993).

Qui et al., "Treatment of Tomato Seed with Harpin Enhances Germination and Induces Resistance to *Ralstonia solanacearum*," *Phytopathology*, 87:6, S80 (1997) (abstract only).

Burr et al., "Increased Potato Yields by Treatment of Seedpieces with Specific Strains of *Pseudomonas Fluorescens* And *P. putida*," *Phytopathology*, 68:1377–1383 (1978).

Ricci et al., "Proteinaceous Elicitors of Plant Defense Responses," B. Fritig eds., *Mechanisms of Plant Defense Responses*, Netherlands, pp. 121–130 (1993).

Keen et al., "Syringolide Elicitors Specified By Avirulence Gene D Alleles In *Pseudomonas syringae*," *Advances in Molecular Genetics of Plant–Microbe Interactions*, 3:41–48 (1994).

Klessig et al., "The Salicylic Acid Signal In Plants," *Plant Molecular Biology*, 26:1439–1458 (1994).

Bogdanove et al., "Unified Nomenclature For Broadly Conserved hrp Genes of Phytopathogenic Bacteria," *Molecular Microbiology*, 20(3):681–683 (1996).

Bonnet et al., "Acquired Resistance Triggered By Elicitins In Tobacco and Other Plants," *European Journal of Plant Pathology*, 102:181–192 (1996).

Cui et al., "The RsmS¯Mutants of *Erwinia carotovora* subsp. *carotovora* Strain Ecc71 Overexpress hrpN$_{Ecc}$ and Elicti a Hypersensitive Reaction–like Response in Tobacco Leaves," *Molecular Plant–Microbe Interactions*, 9(7):566–573 (1996).

Gopalan et al., "Bacterial Genes Involved in the Elicitation of Hypersensitive Response and Pathogenesis," *Plant Disease*, 80(6):604–610 (1996).

Hoffland et al., "Comparison of Systemic Resistance Induced by Avirulent and Nonpathogenic Pseudomonas Species," *Phytopathology*, 86(7):757–762 (1996).

Ryals et al., "Systemic Acquired Resistance," *The Plant Cell*, 8:1809–1819 (1996).

Wei et al., "Induced Systemic Resistance to Cucumber Dieseases and Increased Plant Growth by Plant Growth–Promoting Rhizobacteria Under Field Conditions," *Phytopathology*, 86:221–224 (1996).

Wengelnik et al., "Expression and Localization of HrpA1, a Protein of *Xanthomonas campestris* pv. *vesicatoria* Essential for Pathogenicity and Induction of the Hypersensitive Reaction," *Journal of Bacteriology*, 178:1061–1069 (1996).

Inbar et al., "Elicitors of Plant Defensive Systems Reduce Insect Densities and Disease Incidence," *Journal of Chemical Ecology*, 24(1):135–149 (1998).

Jin et al., "A Truncated Fragment of Harpin$_{Pss}$ Induces Systemic Resistance To *Xanthomonas campetris* pv. *oryzae* In Rice," *Physiological and Molecular Plant Pathology*, 51:243–257 (1997).

Alfano et al., "Analysis of the Role of the *Pseudomonas Syringae* pv. *Syringae* HrpZ Harpin in Elicitation of the Hypersensitive Response in Tobacco Using Functionally Non–Polar hrpZ Deletion Mutations, Truncated HrpZ Fragments, and hrmA Mutations," *Molecular Microbiology*, 19:715–728 (1996).

Linthorst et al., "Constitutive Expression of Pathogenesis–Related Proteins PR–1, GRP, and PR–S in Tobacco Has No Effect on Virus Infection," *The Plant Cell*, 1:285–291 (1989).

Malamy et al., Salicylic Acid and Plant Disease Resistance, *The Plant Journal*, 2:643–654 (1992).

McGurl et al., "Structure, Expression, and Antisense Inhibition of the Systemin Precursor Gene," *Science*, 255:1570–1573 (1992).

Wei et al., "hrpL Activates *Erwinia amylovora* hrp Gene Transcription and Is a Member of the ECF Subfamily of o Factors," *Journal of Bacteriology*, 177:6201–6210 (1995).

Nissinen et al., "Clavibacter Michiganensis Subsp. Sepedonicus Elicits a Hypersensitive Response in Tobacco and Secreted Hypersensitive Response–Inducing Protein," *Phytopathology*, 87:678–684 (1997) (Abstract only).

Schulte et al., Expression of the *Xanthomonas compestris* pv. Vesicatoria hrp Gene Cluster, Which Determines Pathogenicity and Hypersensitivity on Pepper and Tomato, Is Plant Inducible, *Journal of Bacteriology*, 174:815–823 (1992).

Yu, "Elicitins from Phytophthora and Basic Resistance in Tobacco," *Proc. Natl. Acad. Sci. USA*, 92:4088–4094 (1995).

Wu et al., "Disease Resistance Conferred by Expressin of a Gene Encoding $H_2O_2$–Generating Glucose Oxidase in Transgenic Potato Plants," *The Plant Cell*, 7:1357–1368 (1995).

Kim et al., "HrpW of *Erwinia Amylovora*, a New Harpin That Contains a Domain Homologous to Pectate Lyases of a Distinct Class," *Journal of Bacteriology* 180:5203–5210 (1998).

Charkowski et al., "The *Pseudomonas syringae* pv. Tomato HrpW Protein Has Domains Similar to Harpins and Pectate Lyases and Can Elicit the Plant Hypersensitive Response and Bind to Pectate," *Journal of Bacteriology* 180:5211–5217. (1998).

Lorang et al., "Characterization of avrE from *Pseudomonas syringae* pv. Tomato: A hrp–Linked Avirulence Locus Consisting Of at Least Two Transcriptional Units," *MPMI* 8:49–57 (1995).

Barcelo et al., "Plant Water Relations as Affected by Heavy Metal Stress: A Review," *Journal of Plant Nutrition* 13(1), 1–37 (1990).

D. Schoeneweiss, "Water Stress Predisposition to Disease— An Overview," *In Water, Fungi and Plants*, pp. 157–174 (1986).

K. Bradford, "Water Stress and the Water Relations of Seed Development: A Critical Review," *Crop Science*, 34(1):1–11 (1994).

J.P. Grime, "Whole–Plant Responses to Stress in Natural and Agricultural Systems," Society for Experimental Biology 39:31–46 (1989).

Taiz and Ziegler, *Plant Physiology*, The Benjamin/Cummings Publ. Co.,Inc., Redwood City, pp. 346–369 (1991).

HYPERSENSITIVE RESPONSE ELICITOR-INDUCED STRESS RESISTANCE

This application claims benefit of U.S. Provisional Patent Application Ser. No. 60/107,243, filed Nov. 5, 1998.

FIELD OF THE INVENTION

The present invention relates to imparting stress resistance to plants with a hypersensitive response elicitor.

BACKGROUND OF THE INVENTION

Under both natural and agricultural conditions, plants are exposed to various forms of environmental stress. Stress is mainly measured with respect to growth (i.e. biomass accumulation) or with respect to the primary assimilation processes (i.e. carbon dioxide and mineral intake). Soil water deficits, suboptimal and supraoptimal temperatures, salinity, and poor aeration of soils may each cause some growth restrictions during the growing season, so that the yield of plants at the end of the season expresses only a small fraction of their genetic potential. Indeed, it is estimated that in the United States the yield of field-grown crops is only 22% of genetic potential. The same physicochemical factors can become extreme in some habitats, such as deserts or marshes, and only specially adapted vegetation can complete its life cycle in the unusually hostile conditions. In less extreme environments, individual plants can become acclimated to changes in water potential, temperature, salinity, and oxygen deficiency so that their fitness for those environments improves. Some species are better able to adapt than others, and various anatomical, structural, and biochemical mechanisms account for acclimation.

Under riatural and agriculture conditions, plants must constantly endure stress. Some environmental factors can become stressful in a very short period of time (e.g., high or low temperature) or may take long periods of time to stress plants (e.g., soil water content or mineral nutrients). Generally, environmental stress effecting plants can be in the form of climate related stress, air pollution stress, chemical stress, and nutritional stress. Examples of climate related stress include drought, water, frost, cold temperature, high temperature, excessive light, and insufficient light. Air pollution stress can be in the form of carbon dioxide, carbon monoxide, sulfur dioxide, $NO_x$, hydrocarbons, ozone, ultraviolet radiation, and acidic rain. Chemical stress can result from application of insecticides, fungicides, herbicides, and heavy metals. Nutritional stress can be caused by fertilizers, micronutrients, and macronutrients.

For most plants, water is essential for growth. Some plants are able to preserve some water in the soil for later use, while others complete their life cycles during a wet season before the onset of any drought. Other plants are able to aggressively consume water to save themselves while causing water deprivation for other plants in that location. Plants lacking any of these capabilities are severely hampered by the absence of water.

Chilling injury occurs in sensitive species at temperatures that are too low for normal growth but not sufficiently low to form ice. Such injury typically occurs in species of tropical or subtropical origin. When chilling occurs, discoloration or lesions appear on leaves giving them a water-soaked appearance. If roots are chilled, the plants may wilt. On the other hand, freezing temperatures and the accompanying formation of ice crystals in plants can be lethal if ice crystals extend into protoplasts or remain for long periods. Stress is also caused by the other temperature extremes with few plants being able to survive high temperatures. When higher plant cells or tissues are dehydrated or are not growing, they can survive higher temperatures than cells which are hydrated, vegetative, and growing. Tissues which are actively growing can rarely survive at temperatures above 45° C.

High salt concentrations are another form of environmental stress which can afflict plants. In natural conditions, such high concentrations of salt are found close to seashores and estuaries. Farther inland, natural salt may seep from geological deposits adjoining agricultural areas. In addition, salt can accumulate in irrigation water when pure water is evaporated or transpired from soil. About ⅓ of all irrigated farmland is effected by high salt concentrations. High salt content not only injures plants but degrades soil structure by decreasing porosity and water permeability.

Air pollution in the form of ozone, carbon dioxide, carbon monoxide, sulfur dioxide, $NO_x$, and hydrocarbons can very adversely effect plant growth by creating smog and environmental warming.

The present invention is directed to overcoming various forms of environmental stress and imparting resistance in plants to such stress.

SUMMARY OF THE INVENTION

The present invention relates to the use of a hypersensitive response elicitor protein or polypeptide to impart stress resistance to plants. In one embodiment of the present invention, the hypersensitive response elicitor protein or polypeptide is applied to plants or plant seeds under conditions effective to impart stress resistance. Alternatively, stress resistance is imparted by providing a transgenic plant or plant seed transformed with a DNA molecule which encodes for a hypersensitive response elicitor protein or polypeptide and growing the transgenic plant or plants produced from the transgenic plant seeds under conditions effective to impart stress resistance.

Stress encompasses any environmental factor having an adverse effect on plant physiology and development. Examples of such environmental stress include climate-related stress (e.g., drought, water, frost, cold temperature, high temperature, excessive light, and insufficient light), air polllution stress (e.g., carbon dioxide, carbon monoxide, sulfur dioxide, $NO_x$, hydrocarbons, ozone, ultraviolet radiation, acidic rain), chemical (e.g., insecticides, fungicides, herbicides, heavy metals), and nutritional stress (e.g., fertilizer, micronutrients, macronutrients). Applicants have found that use of hypersensitive response elicitors in accordance with the present invention impart resistance to plants against such forms of environmental stress.

DETAILED DESCRIPTION OF THE INVENTION

The present invention relates to the use of a hypersensitive response licitor protein or polypeptide to impart stress resistance to plants. In one embodiment of the present invention, the hypersensitive response elicitor protein or polypeptide is applied to plants or plant seeds under conditions effective to impart stress resistance. Alternatively, the stress resistance is imparted by providing a transgenic plant or plant seed transformed with a DNA molecule which encodes for a hypersensitive response elicitor protein or polypeptide and growing the transgenic plant or plants produced from the transgenic plant seeds under conditions effective to impart stress resistance.

The hypersensitive response elicitor polypeptides or proteins according to the present invention are derived from hypersensitive response elicitor polypeptides or proteins of a wide variety of fungal and bacterial pathogens. Such polypeptides or proteins are able to elicit local necrosis in plant tissue contacted by the elicitor. Examples of suitable bacterial sources of polypeptide or protein elicitors include Erwinia, Pseudomonas, and Xanthamonas species (e.g., the following bacteria: *Erwinia amylovora, Erwinia chrysanthemi, Erwinia stewartii, Erwinia carotovora, Pseudomonas syringae, Pseudomonas solancearum, Xanthomonas campestris*, and mixtures thereof). In addition to hypersensitive response elicitors from these Gram negative bacteria, it is possible to use elicitors from Gram positive bacteria. One example is *Clavibacter michiganensis* subsp. sepedonicus.

An example of a fungal source of a hypersensitive response elicitor protein or polypeptide is Phytophthora. Suitable species of Phytophthora include *Phytophthora parasitica, Phytophthora cryptogea, Phytophthora cinnamomi, Phytophthora capsici, Phytophthora megasperma*, and *Phytophthora citrophthora.*

The hypersensitive response elicitor polypeptide or protein from *Erwinia chrysanthemi* has an amino acid sequence corresponding to SEQ. ID. No. 1 as follows:

```
Met Gln Ile Thr Ile Lys Ala His Ile Gly Gly Asp Leu Gly Val Ser
1               5                   10                  15

Gly Leu Gly Ala Gln Gly Leu Lys Gly Leu Asn Ser Ala Ala Ser Ser
            20                  25                  30

Leu Gly Ser Ser Val Asp Lys Leu Ser Ser Thr Ile Asp Lys Leu Thr
        35                  40                  45

Ser Ala Leu Thr Ser Met Met Phe Gly Gly Ala Leu Ala Gln Gly Leu
    50                  55                  60

Gly Ala Ser Ser Lys Gly Leu Gly Met Ser Asn Gln Leu Gly Gln Ser
65                  70                  75                  80

Phe Gly Asn Gly Ala Gln Gly Ala Ser Asn Leu Leu Ser Val Pro Lys
                85                  90                  95

Ser Gly Gly Asp Ala Leu Ser Lys Met Phe Asp Lys Ala Leu Asp Asp
            100                 105                 110

Leu Leu Gly His Asp Thr Val Thr Lys Leu Thr Asn Gln Ser Asn Gln
        115                 120                 125

Leu Ala Asn Ser Met Leu Asn Ala Ser Gln Met Thr Gln Gly Asn Met
    130                 135                 140

Asn Ala Phe Gly Ser Gly Val Asn Asn Ala Leu Ser Ser Ile Leu Gly
145                 150                 155                 160

Asn Gly Leu Gly Gln Ser Met Ser Gly Phe Ser Gln Pro Ser Leu Gly
                165                 170                 175

Ala Gly Gly Leu Gln Gly Leu Ser Gly Ala Gly Ala Phe Asn Gln Leu
            180                 185                 190

Gly Asn Ala Ile Gly Met Gly Val Gly Gln Asn Ala Ala Leu Ser Ala
        195                 200                 205

Leu Ser Asn Val Ser Thr His Val Asp Gly Asn Asn Arg His Phe Val
    210                 215                 220

Asp Lys Glu Asp Arg Gly Met Ala Lys Glu Ile Gly Gln Phe Met Asp
225                 230                 235                 240

Gln Tyr Pro Glu Ile Phe Gly Lys Pro Glu Tyr Gln Lys Asp Gly Trp
                245                 250                 255

Ser Ser Pro Lys Thr Asp Asp Lys Ser Trp Ala Lys Ala Leu Ser Lys
            260                 265                 270

Pro Asp Asp Asp Gly Met Thr Gly Ala Ser Met Asp Lys Phe Arg Gln
        275                 280                 285

Ala Met Gly Met Ile Lys Ser Ala Val Ala Gly Asp Thr Gly Asn Thr
    290                 295                 300

Asn Leu Asn Leu Arg Gly Ala Gly Gly Ala Ser Leu Gly Ile Asp Ala
305                 310                 315                 320

Ala Val Val Gly Asp Lys Ile Ala Asn Met Ser Leu Gly Lys Leu Ala
                325                 330                 335

Asn Ala
```

This hypersensitive response elicitor polypeptide or protein has a molecular weight of 34 kDa, is heat stable, has a glycine content of greater than 16%, and contains substantially no cysteine. The *Erwinia chrysanthemi* hypersensitive response elicitor polypeptide or protein is encoded by a DNA molecule having a nucleotide sequence corresponding to SEQ. ID. No. 2 as follows:

```
CGATTTTACC CGGGTGAACG TGCTATGACC GACAGCATCA CGGTATTCGA CACCGTTACG    60
GCGTTTATGG CCGCGATGAA CCGGCATCAG GCGGCGCGCT GGTCGCCGCA ATCCGGCGTC   120
GATCTGGTAT TTCAGTTTGG GGACACCGGG CGTGAACTCA TGATGCAGAT TCAGCCGGGG   180
CAGCAATATC CCGGCATGTT GCGCACGCTG CTCGCTCGTC GTTATCAGCA GGCGGCAGAG   240
TGCGATGGCT GCCATCTGTG CCTGAACGGC AGCGATGTAT TGATCCTCTG GTGGCCGCTG   300
CCGTCGGATC CCGGCAGTTA TCCGCAGGTG ATCGAACGTT TGTTTGAACT GGCGGGAATG   360
ACGTTGCCGT CGCTATCCAT AGCACCGACG GCGCGTCCGC AGACAGGGAA CGGACGCGCC   420
CGATCATTAA GATAAAGGCG GCTTTTTTTA TTGCAAAACG GTAACGGTGA GGAACCGTTT   480
CACCGTCGGC GTCACTCAGT AACAAGTATC CATCATGATG CCTACATCGG GATCGGCGTG   540
GGCATCCGTT GCAGATACTT TTGCGAACAC CTGACATGAA TGAGGAAACG AAATTATGCA   600
AATTACGATC AAAGCGCACA TCGGCGGTGA TTTGGGCGTC TCCGGTCTGG GGCTGGGTGC   660
TCAGGGACTG AAAGGACTGA ATTCCGCGGC TTCATCGCTG GGTTCCAGCG TGGATAAACT   720
GAGCAGCACC ATCGATAAGT TGACCTCCGC GCTGACTTCG ATGATGTTTG GCGGCGCGCT   780
GGCGCAGGGG CTGGGCGCCA GCTCGAAGGG GCTGGGGATG AGCAATCAAC TGGGCCAGTC   840
TTTCGGCAAT GGCGCGCAGG GTGCGAGCAA CCTGCTATCC GTACCGAAAT CCGGCGGCGA   900
TGCGTTGTCA AAAATGTTTG ATAAAGCGCT GGACGATCTG CTGGGTCATG ACACCGTGAC   960
CAAGCTGACT AACCAGAGCA ACCAACTGGC TAATTCAATG CTGAACGCCA GCCAGATGAC  1020
CCAGGGTAAT ATGAATGCGT TCGGCAGCGG TGTGAACAAC GCACTGTCGT CCATTCTCGG  1080
CAACGGTCTC GGCCAGTCGA TGAGTGGCTT CTCTCAGCCT TCTCTGGGGG CAGGCGGCTT  1140
GCAGGGCCTG AGCGGCGCGG GTGCATTCAA CCAGTTGGGT AATGCCATCG GCATGGGCGT  1200
GGGGCAGAAT GCTGCGCTGA GTGCGTTGAG TAACGTCAGC ACCCACGTAG ACGGTAACAA  1260
CCGCCACTTT GTAGATAAAG AAGATCGCGG CATGGCGAAA GAGATCGGCC AGTTTATGGA  1320
TCAGTATCCG GAAATATTCG GTAAACCGGA ATACCAGAAA GATGGCTGGA GTTCGCCGAA  1380
GACGGACGAC AAATCCTGGG CTAAAGCGCT GAGTAAACCG GATGATGACG GTATGACCGG  1440
CGCCAGCATG GACAAATTCC GTCAGGCGAT GGGTATGATC AAAAGCGCGG TGGCGGGTGA  1500
TACCGGCAAT ACCAACCTGA ACCTGCGTGG CGCGGGCGGT GCATCGCTGG GTATCGATGC  1560
GGCTGTCGTC GGCGATAAAA TAGCCAACAT GTCGCTGGGT AAGCTGGCCA ACGCCTGATA  1620
ATCTGTGCTG GCCTGATAAA GCGGAAACGA AAAAAGAGAC GGGGAAGCCT GTCTCTTTTC  1680
TTATTATGCG GTTTATGCGG TTACCTGGAC CGGTTAATCA TCGTCATCGA TCTGGTACAA  1740
ACGCACATTT TCCCGTTCAT TCGCGTCGTT ACGCGCCACA ATCGCGATGG CATCTTCCTC  1800
GTCGCTCAGA TTGCGCGGCT GATGGGGAAC GCCGGGTGGA ATATAGAGAA ACTCGCCGGC  1860
CAGATGGAGA CACGTCTGCG ATAAATCTGT GCCGTAACGT GTTTCTATCC GCCCCTTTAG  1920
CAGATAGATT GCGGTTTCGT AATCAACATG GTAATGCGGT TCCGCCTGTG CGCCGGCCGG  1980
GATCACCACA ATATTCATAG AAAGCTGTCT TGCACCTACC GTATCGCGGG AGATACCGAC  2040
AAAATAGGGC AGTTTTTGCG TGGTATCCGT GGGGTGTTCC GGCCTGACAA TCTTGAGTTG  2100
GTTCGTCATC ATCTTTCTCC ATCTGGGCGA CCTGATCGGT T                     2141
```

The hypersensitive response elicitor polypeptide or protein derived from *Erwinia amylovora* has an amino acid sequence corresponding to SEQ. ID. No. 3 as follows:

```
Met Ser Leu Asn Thr Ser Gly Leu Gly Ala Ser Thr Met Gln Ile Ser
 1               5                  10                  15

Ile Gly Gly Ala Gly Gly Asn Asn Gly Leu Leu Gly Thr Ser Arg Gln
             20                  25                  30

Asn Ala Gly Leu Gly Gly Asn Ser Ala Leu Gly Leu Gly Gly Gly Asn
             35                  40                  45

Gln Asn Asp Thr Val Asn Gln Leu Ala Gly Leu Leu Thr Gly Met Met
 50                  55                  60

Met Met Met Ser Met Met Gly Gly Gly Leu Met Gly Gly Gly Leu
65                   70                  75                  80

Gly Gly Gly Leu Gly Asn Gly Leu Gly Gly Ser Gly Gly Leu Gly Glu
             85                  90                  95

Gly Leu Ser Asn Ala Leu Asn Asp Met Leu Gly Gly Ser Leu Asn Thr
            100                 105                 110

Leu Gly Ser Lys Gly Gly Asn Asn Thr Thr Ser Thr Thr Asn Ser Pro
            115                 120                 125

Leu Asp Gln Ala Leu Gly Ile Asn Ser Thr Ser Gln Asn Asp Asp Ser
            130                 135                 140

Thr Ser Gly Thr Asp Ser Thr Ser Asp Ser Ser Asp Pro Met Gln Gln
145                 150                 155                 160

Leu Leu Lys Met Phe Ser Glu Ile Met Gln Ser Leu Phe Gly Asp Gly
                165                 170                 175

Gln Asp Gly Thr Gln Gly Ser Ser Ser Gly Gly Lys Gln Pro Thr Glu
            180                 185                 190

Gly Glu Gln Asn Ala Tyr Lys Lys Gly Val Thr Asp Ala Leu Ser Gly
            195                 200                 205

Leu Met Gly Asn Gly Leu Ser Gln Leu Leu Gly Asn Gly Gly Leu Gly
            210                 215                 220

Gly Gly Gln Gly Gly Asn Ala Gly Thr Gly Leu Asp Gly Ser Ser Leu
225                 230                 235                 240

Gly Gly Lys Gly Leu Gln Asn Leu Ser Gly Pro Val Asp Tyr Gln Gln
            245                 250                 255

Leu Gly Asn Ala Val Gly Thr Gly Ile Gly Met Lys Ala Gly Ile Gln
            260                 265                 270

Ala Leu Asn Asp Ile Gly Thr His Arg His Ser Ser Thr Arg Ser Phe
            275                 280                 285

Val Asn Lys Gly Asp Arg Ala Met Ala Lys Glu Ile Gly Gln Phe Met
            290                 295                 300

Asp Gln Tyr Pro Glu Val Phe Gly Lys Pro Gln Tyr Gln Lys Gly Pro
305                 310                 315                 320

Gly Gln Glu Val Lys Thr Asp Asp Lys Ser Trp Ala Lys Ala Leu Ser
            325                 330                 335

Lys Pro Asp Asp Asp Gly Met Thr Pro Ala Ser Met Glu Gln Phe Asn
            340                 345                 350

Lys Ala Lys Gly Met Ile Lys Arg Pro Met Ala Gly Asp Thr Gly Asn
            355                 360                 365

Gly Asn Leu Gln Ala Arg Gly Ala Gly Ser Ser Leu Gly Ile Asp
            370                 375                 380

Ala Met Met Ala Gly Asp Ala Ile Asn Asn Met Ala Leu Gly Lys Leu
385                 390                 395                 400

Gly Ala Ala
```

This hypersensitive response elicitor polypeptide or protein has a molecular weight of about 39 kDa, has a pI of approximately 4.3, and is heat stable at 100° C. for at least 10 minutes. This hypersensitive response elicitor polypeptide or protein has substantially no cysteine. The hypersensitive response elicitor polypeptide or protein derived from *Erwinia amylovora* is more fully described in Wei, Z.-M., R. J. Laby, C. H. Zumoff, D. W. Bauer, S.-Y. He, A. Collmer, and S. V. Beer, "Harpin, Elicitor of the Hypersensitive Response Produced by the Plant Pathogen *Erwinia amylovora*," *Science* 257:85–88 (1992), which is hereby incorporated by reference. The DNA molecule encoding this polypeptide or protein has a nucleotide sequence corresponding to SEQ. ID. No. 4 as follows:

```
AAGCTTCGGC ATGGCACGTT TGACCGTTGG GTCGGCAGGG TACGTTTGAA TTATTCATAA    60
GAGGAATACG TTATGAGTCT GAATACAAGT GGGCTGGGAG CGTCAACGAT GCAAATTTCT   120
ATCGGCGGTG CGGGCGGAAA TAACGGGTTG CTGGGTACCA GTCGCCAGAA TGCTGGGTTG   180
GGTGGCAATT CTGCACTGGG GCTGGGCGGC GGTAATCAAA ATGATACCGT CAATCAGCTG   240
GCTGGCTTAC TCACCGGCAT GATGATGATG ATGAGCATGA TGGGCGGTGG TGGGCTGATG   300
GGCGGTGGCT TAGGCGGTGG CTTAGGTAAT GGCTTGGGTG GCTCAGGTGG CCTGGGCGAA   360
GGACTGTCGA ACGCGCTGAA CGATATGTTA GGCGGTTCGC TGAACACGCT GGGCTCGAAA   420
GGCGGCAACA ATACCACTTC AACAACAAAT TCCCCGCTGG ACCAGGCGCT GGGTATTAAC   480
TCAACGTCCC AAAACGACGA TTCCACCTCC GGCACAGATT CCACCTCAGA CTCCAGCGAC   540
CCGATGCAGC AGCTGCTGAA GATGTTCAGC GAGATAATGC AAAGCCTGTT TGGTGATGGG   600
CAAGATGGCA CCCAGGGCAG TTCCTCTGGG GGCAAGCAGC CGACCGAAGG CGAGCAGAAC   660
GCCTATAAAA AAGGAGTCAC TGATGCGCTG TCGGGCCTGA TGGGTAATGG TCTGAGCCAG   720
CTCCTTGGCA ACGGGGGACT GGGAGGTGGT CAGGGCGGTA ATGCTGGCAC GGGTCTTGAC   780
GGTTCGTCGC TGGGCGGCAA AGGGCTGCAA AACCTGAGCG GGCCGGTGGA CTACCAGCAG   840
TTAGGTAACG CCGTGGGTAC CGGTATCGGT ATGAAAGCGG GCATTCAGGC GCTGAATGAT   900
ATCGGTACGC ACAGGCACAG TTCAACCCGT TCTTTCGTCA ATAAAGGCGA TCGGGCGATG   960
GCGAAGGAAA TCGGTCAGTT CATGGACCAG TATCCTGAGG TGTTTGGCAA GCCGCAGTAC  1020
CAGAAAGGCC CGGGTCAGGA GGTGAAAACC GATGACAAAT CATGGGCAAA AGCACTGAGC  1080
AAGCCAGATG ACGACGGAAT GACACCAGCC AGTATGGAGC AGTTCAACAA AGCCAAGGGC  1140
ATGATCAAAA GGCCCATGGC GGGTGATACC GGCAACGGCA ACCTGCAGGC ACGCGGTGCC  1200
GGTGGTTCTT CGCTGGGTAT TGATGCCATG ATGGCCGGTG ATGCCATTAA CAATATGGCA  1260
CTTGGCAAGC TGGGCGCGGC TTAAGCTT                                     1288
```

Another potentially suitable hypersensitive response elicitor from *Erwinia amylovora* is disclosed in U.S. patent application Ser. No. 09/120,927, which is hereby incorporated by reference. The protein is encoded by a DNA molecule having a nucleic acid sequence of SEQ. ID. No. 5 as follows:

```
ATGTCAATTC TTACGCTTAA CAACAATACC TCGTCCTCGC CGGGTCTGTT CCAGTCCGGG    60
GGGGACAACG GGCTTGGTGG TCATAATGCA AATTCTGCGT TGGGGCAACA ACCCATCGAT   120
CGGCAAACCA TTGAGCAAAT GGCTCAATTA TTGGCGGAAC TGTTAAAGTC ACTGCTATCG   180
CCACAATCAG GTAATGCGGC AACCGGAGCC GGTGGCAATG ACCAGACTAC AGGAGTTGGT   240
AACGCTGGCG GCCTGAACGG ACGAAAAGGC ACAGCAGGAA CCACTCCGCA GTCTGACAGT   300
CAGAACATGC TGAGTGAGAT GGGCAACAAC GGGCTGGATC AGGCCATCAC GCCCGATGGC   360
CAGGGCGGCG GGCAGATCGG CGATAATCCT TTACTGAAAG CCATGCTGAA GCTTATTGCA   420
CGCATGATGG ACGGCCAAAG CGATCAGTTT GGCCAACCTG GTACGGGCAA CAACAGTGCC   480
```

```
TCTTCCGGTA CTTCTTCATC TGGCGGTTCC CCTTTTAACG ATCTATCAGG GGGGAAGGCC    540

CCTTCCGGCA ACTCCCCTTC CGGCAACTAC TCTCCCGTCA GTACCTTCTC ACCCCCATCC    600

ACGCCAACGT CCCCTACCTC ACCGCTTGAT TTCCCTTCTT CTCCCACCAA AGCAGCCGGG    660

GGCAGCACGC CGGTAACCGA TCATCCTGAC CCTGTTGGTA GCGCGGGCAT CGGGGCCGGA    720

AATTCGGTGG CCTTCACCAG CGCCGGCGCT AATCAGACGG TGCTGCATGA CACCATTACC    780

GTGAAAGCGG GTCAGGTGTT TGATGGCAAA GGACAAACCT TCACCGCCGG TTCAGAATTA    840

GGCGATGGCG GCCAGTCTGA AAACCAGAAA CCGCTGTTTA TACTGGAAGA CGGTGCCAGC    900

CTGAAAAACG TCACCATGGG CGACGACGGG GCGGATGGTA TTCATCTTTA CGGTGATGCC    960

AAAATAGACA ATCTGCACGT CACCAACGTG GGTGAGGACG CGATTACCGT TAAGCCAAAC   1020

AGCGCGGGCA AAAAATCCCA CGTTGAAATC ACTAACAGTT CCTTCGAGCA CGCCTCTGAC   1080

AAGATCCTGC AGCTGAATGC CGATACTAAC CTGAGCGTTG ACAACGTGAA GGCCAAAGAC   1140

TTTGGTACTT TTGTACGCAC TAACGGCGGT CAACAGGGTA ACTGGGATCT GAATCTGAGC   1200

CATATCAGCG CAGAAGACGG TAAGTTCTCG TTCGTTAAAA GCGATAGCGA GGGGCTAAAC   1260

GTCAATACCA GTGATATCTC ACTGGGTGAT GTTGAAAACC ACTACAAAGT GCCGATGTCC   1320

GCCAACCTGA AGGTGGCTGA ATGA                                         1344
```

See GenBank Accession No. U94513. The isolated DNA molecule of the present invention encodes a hypersensitive response elicitor protein or polypeptide having an amino acid sequence of SEQ. ID. No. 6 as follows:

```
Met Ser Ile Leu Thr Leu Asn Asn Thr Ser Ser Pro Gly Leu
1               5                   10              15

Phe Gln Ser Gly Gly Asp Asn Gly Leu Gly Gly His Asn Ala Asn Ser
            20                  25              30

Ala Leu Gly Gln Gln Pro Ile Asp Arg Gln Thr Ile Glu Gln Met Ala
            35              40              45

Gln Leu Leu Ala Glu Leu Leu Lys Ser Leu Leu Ser Pro Gln Ser Gly
    50              55              60

Asn Ala Ala Thr Gly Ala Gly Gly Asn Asp Gln Thr Thr Gly Val Gly
65              70              75              80

Asn Ala Gly Gly Leu Asn Gly Arg Lys Gly Thr Ala Gly Thr Thr Pro
                85              90              95

Gln Ser Asp Ser Gln Asn Met Leu Ser Glu Met Gly Asn Asn Gly Leu
            100             105             110

Asp Gln Ala Ile Thr Pro Asp Gly Gln Gly Gly Gly Gln Ile Gly Asp
            115             120             125

Asn Pro Leu Leu Lys Ala Met Leu Lys Leu Ile Ala Arg Met Met Asp
    130             135             140

Gly Gln Ser Asp Gln Phe Gly Gln Pro Gly Thr Gly Asn Asn Ser Ala
145             150             155             160

Ser Ser Gly Thr Ser Ser Ser Gly Gly Ser Pro Phe Asn Asp Leu Ser
                165             170             175

Gly Gly Lys Ala Pro Ser Gly Asn Ser Pro Ser Gly Asn Tyr Ser Pro
            180             185             190

Val Ser Thr Phe Ser Pro Pro Ser Thr Pro Thr Ser Pro Thr Ser Pro
            195             200             205

Leu Asp Phe Pro Ser Ser Pro Thr Lys Ala Ala Gly Gly Ser Thr Pro
    210             215             220
```

```
Val Thr Asp His Pro Asp Pro Val Gly Ser Ala Gly Ile Gly Ala Gly
225                 230                 235                 240

Asn Ser Val Ala Phe Thr Ser Ala Gly Ala Asn Gln Thr Val Leu His
            245                 250                 255

Asp Thr Ile Thr Val Lys Ala Gly Gln Val Phe Asp Gly Lys Gly Gln
            260                 265                 270

Thr Phe Thr Ala Gly Ser Glu Leu Gly Asp Gly Gln Ser Glu Asn
        275                 280                 285

Gln Lys Pro Leu Phe Ile Leu Glu Asp Gly Ala Ser Leu Lys Asn Val
    290                 295                 300

Thr Met Gly Asp Asp Gly Ala Asp Gly Ile His Leu Tyr Gly Asp Ala
305                 310                 315                 320

Lys Ile Asp Asn Leu His Val Thr Asn Val Gly Glu Asp Ala Ile Thr
                325                 330                 335

Val Lys Pro Asn Ser Ala Gly Lys Lys Ser His Val Glu Ile Thr Asn
            340                 345                 350

Ser Ser Phe Glu His Ala Ser Asp Lys Ile Leu Gln Leu Asn Ala Asp
        355                 360                 365

Thr Asn Leu Ser Val Asp Asn Val Lys Ala Lys Asp Phe Gly Thr Phe
370                 375                 380

Val Arg Thr Asn Gly Gly Gln Gln Gly Asn Trp Asp Leu Asn Leu Ser
385                 390                 395                 400

His Ile Ser Ala Glu Asp Gly Lys Phe Ser Phe Val Lys Ser Asp Ser
                405                 410                 415

Glu Gly Leu Asn Val Asn Thr Ser Asp Ile Ser Leu Gly Asp Val Glu
            420                 425                 430

Asn His Tyr Lys Val Pro Met Ser Ala Asn Leu Lys Val Ala Glu
            435                 440                 445
```

This protein or polypeptide is acidic, rich in glycine and serine, and lacks cysteine. It is also heat stable, protease sensitive, and suppressed by inhibitors of plant metabolism. The protein or polypeptide of the present invention has a predicted molecular size of ca. 4.5 kDa.

Another potentially suitable hypersensitive response elicitor from *Erwinia amylovora* is disclosed in U.S. patent application Ser. No. 09/120,663, which is hereby incorporated by reference. The protein is encoded by a DNA molecule having a nucleic acid sequence of SEQ. ID. No. 7 as follows:

```
ATGGAATTAA AATCACTGGG AACTGAACAC AAGGCGGCAG TACACACAGC GGCGCACAAC    60

CCTGTGGGGC ATGGTGTTGC CTTACAGCAG GGCAGCAGCA GCAGCAGCCC GCAAAATGCC   120

GCTGCATCAT TGGCGGCAGA AGGCAAAAAT CGTGGGAAAA TGCCGAGAAT TCACCAGCCA   180

TCTACTGCGG CTGATGGTAT CAGCGCTGCT CACCAGCAAA AGAAATCCTT CAGTCTCAGG   240

GGCTGTTTGG GGACGAAAAA ATTTTCCAGA TCGGCACCGC AGGGCCAGCC AGGTACCACC   300

CACAGCAAAG GGGCAACATT GCGCGATCTG CTGGCGCGGG ACGACGGCGA AACGCAGCAT   360

GAGGCGGCCG CGCCAGATGC GGCGCGTTTG ACCCGTTCGG GCGGCGTCAA ACGCCGCAAT   420

ATGGACGACA TGGCCGGGCG GCCAATGGTG AAAGGTGGCA GCGGCGAAGA TAAGGTACCA   480

ACGCAGCAAA AACGGCATCA GCTGAACAAT TTTGGCCAGA TGCGCCAAAC GATGTTGAGC   540

AAAATGGCTC ACCCGGCTTC AGCCAACGCC GGCGATCGCC TGCAGCATTC ACCGCCGCAC   600

ATCCCGGGTA GCCACCACGA AATCAAGGAA GAACCGGTTG GCTCCACCAG CAAGGCAACA   660

ACGGCCCACG CAGACAGAGT GGAAATCGCT CAGGAAGATG ACGACAGCGA ATTCCAGCAA   720
```

-continued

```
CTGCATCAAC AGCGGCTGGC GCGCGAACGG GAAAATCCAC CGCAGCCGCC CAAACTCGGC    780

GTTGCCACAC CGATTAGCGC CAGGTTTCAG CCCAAACTGA CTGCGGTTGC GGAAAGCGTC    840

CTTGAGGGGA CAGATACCAC GCAGTCACCC CTTAAGCCGC AATCAATGCT GAAAGGAAGT    900

GGAGCCGGGG TAACGCCGCT GGCGGTAACG CTGGATAAAG GCAAGTTGCA GCTGGCACCG    960

GATAATCCAC CCGCGCTCAA TACGTTGTTG AAGCAGACAT TGGGTAAAGA CACCCAGCAC   1020

TATCTGGCGC ACCATGCCAG CAGCGACGGT AGCCAGCATC TGCTGCTGGA CAACAAAGGC   1080

CACCTGTTTG ATATCAAAAG CACCGCCACC AGCTATAGCG TGCTGCACAA CAGCCACCCC   1140

GGTGAGATAA AGGGCAAGCT GGCGCAGGCG GGTACTGGCT CCGTCAGCGT AGACGGTAAA   1200

AGCGGCAAGA TCTCGCTGGG GAGCGGTACG CAAAGTCACA ACAAAACAAT GCTAAGCCAA   1260

CCGGGGGAAG CGCACCGTTC CTTATTAACC GGCATTTGGC AGCATCCTGC TGGCGCAGCG   1320

CGGCCGCAGG GCGAGTCAAT CCGCCTGCAT GACGACAAAA TTCATATCCT GCATCCGGAG   1380

CTGGGCGTAT GGCAATCTGC GGATAAAGAT ACCCACAGCC AGCTGTCTCG CCAGGCAGAC   1440

GGTAAGCTCT ATGCGCTGAA AGACAACCGT ACCCTGCAAA ACCTCTCCGA TAATAAATCC   1500

TCAGAAAAGC TGGTCGATAA AATCAAATCG TATTCCGTTG ATCAGCGGGG GCAGGTGGCG   1560

ATCCTGACGG ATACTCCCGG CCGCCATAAG ATGAGTATTA TGCCCTCGCT GGATGCTTCC   1620

CCGGAGAGCC ATATTTCCCT CAGCCTGCAT TTTGCCGATG CCCACCAGGG GTTATTGCAC   1680

GGGAAGTCGG AGCTTGAGGC ACAATCTGTC GCGATCAGCC ATGGGCGACT GGTTGTGGCC   1740

GATAGCGAAG GCAAGCTGTT TAGCGCCGCC ATTCCGAAGC AAGGGGATGG AAACGAACTG   1800

AAAATGAAAG CCATGCCTCA GCATGCGCTC GATGAACATT TTGGTCATGA CCACCAGATT   1860

TCTGGATTTT TCCATGACGA CCACGGCCAG CTTAATGCGC TGGTGAAAAA TAACTTCAGG   1920

CAGCAGCATG CCTGCCCGTT GGGTAACGAT CATCAGTTTC ACCCCGGCTG GAACCTGACT   1980

GATGCGCTGG TTATCGACAA TCAGCTGGGG CTGCATCATA CCAATCCTGA ACCGCATGAG   2040

ATTCTTGATA TGGGGCATTT AGGCAGCCTG GCGTTACAGG AGGGCAAGCT TCACTATTTT   2100

GACCAGCTGA CCAAAGGGTG GACTGGCGCG GAGTCAGATT GTAAGCAGCT GAAAAAAGGC   2160

CTGGATGGAG CAGCTTATCT ACTGAAAGAC GGTGAAGTGA AACGCCTGAA TATTAATCAG   2220

AGCACCTCCT CTATCAAGCA CGGAACGGAA AACGTTTTTT CGCTGCCGCA TGTGCGCAAT   2280

AAACCGGAGC CGGGAGATGC CCTGCAAGGG CTGAATAAAG ACGATAAGGC CCAGGCCATG   2340

GCGGTGATTG GGTAAATAA ATACCTGGCG CTGACGAAA AAGGGGACAT TCGCTCCTTC   2400

CAGATAAAAC CCGGCACCCA GCAGTTGGAG CGGCCGGCAC AAACTCTCAG CCGCGAAGGT   2460

ATCAGCGGCG AACTGAAAGA CATTCATGTC GACCACAAGC AGAACCTGTA TGCCTTGACC   2520

CACGAGGGAG AGGTGTTTCA TCAGCCGCGT GAAGCCTGGC AGAATGGTGC CGAAAGCAGC   2580

AGCTGGCACA AACTGGCGTT GCCACAGAGT GAAAGTAAGC TAAAAAGTCT GGACATGAGC   2640

CATGAGCACA AACCGATTGC CACCTTTGAA GACGGTAGCC AGCATCAGCT GAAGGCTGGC   2700

GGCTGGCACG CCTATGCGGC ACCTGAACGC GGGCCGCTGG CGGTGGGTAC CAGCGGTTCA   2760

CAAACCGTCT TTAACCGACT AATGCAGGGG GTGAAAGGCA AGGTGATCCC AGGCAGCGGG   2820

TTGACGGTTA AGCTCTCGGC TCAGACGGGG GGAATGACCG GCGCCGAAGG GCGCAAGGTC   2880

AGCAGTAAAT TTTCCGAAAG GATCCGCGCC TATGCGTTCA ACCCAACAAT GTCCACGCCG   2940

CGACCGATTA AAAATGCTGC TTATGCCACA CAGCACGGCT GGCAGGGCG TGAGGGGTTG   3000

AAGCCGTTGT ACGAGATGCA GGGAGCGCTG ATTAAACAAC TGGATGCGCA TAACGTTCGT   3060

CATAACGCGC CACAGCCAGA TTTGCAGAGC AAACTGGAAA CTCTGGATTT AGGCGAACAT   3120
```

```
GGCGCAGAAT TGCTTAACGA CATGAAGCGC TTCCGCGACG AACTGGAGCA GAGTGCAACC      3180

CGTTCGGTGA CCGTTTTAGG TCAACATCAG GGAGTGCTAA AAAGCAACGG TGAAATCAAT      3240

AGCGAATTTA AGCCATCGCC CGGCAAGGCG TTGGTCCAGA GCTTTAACGT CAATCGCTCT      3300

GGTCAGGATC TAAGCAAGTC ACTGCAACAG GCAGTACATG CCACGCCGCC ATCCGCAGAG      3360

AGTAAACTGC AATCCATGCT GGGGCACTTT GTCAGTGCCG GGGTGGATAT GAGTCATCAG      3420

AAGGGCGAGA TCCCGCTGGG CCGCCAGCGC GATCCGAATG ATAAAACCGC ACTGACCAAA      3480

TCGCGTTTAA TTTTAGATAC CGTGACCATC GGTGAACTGC ATGAACTGGC CGATAAGGCG      3540

AAACTGGTAT CTGACCATAA ACCCGATGCC GATCAGATAA ACAGCTGCG CCAGCAGTTC       3600

GATACGCTGC GTGAAAAGCG GTATGAGAGC AATCCGGTGA AGCATTACAC CGATATGGGC      3660

TTCACCCATA ATAAGGCGCT GGAAGCAAAC TATGATGCGG TCAAAGCCTT TATCAATGCC      3720

TTTAAGAAAG AGCACCACGG CGTCAATCTG ACCACGCGTA CCGTACTGGA ATCACAGGGC      3780

AGTGCGGAGC TGGCGAAGAA GCTCAAGAAT ACGCTGTTGT CCCTGGACAG TGGTGAAAGT      3840

ATGAGCTTCA GCCGGTCATA TGGCGGGGGC GTCAGCACTG TCTTTGTGCC TACCCTTAGC      3900

AAGAAGGTGC CAGTTCCGGT GATCCCCGGA GCCGGCATCA CGCTGGATCG CGCCTATAAC      3960

CTGAGCTTCA GTCGTACCAG CGGCGGATTG AACGTCAGTT TTGGCCGCGA CGGCGGGGTG      4020

AGTGGTAACA TCATGGTCGC TACCGGCCAT GATGTGATGC CCTATATGAC CGGTAAGAAA      4080

ACCAGTGCAG GTAACGCCAG TGACTGGTTG AGCGCAAAAC ATAAAATCAG CCCGGACTTG      4140

CGTATCGGCG CTGCTGTGAG TGGCACCCTG CAAGGAACGC TACAAAACAG CCTGAAGTTT      4200

AAGCTGACAG AGGATGAGCT GCCTGGCTTT ATCCATGGCT TGACGCATGG CACGTTGACC      4260

CCGGCAGAAC TGTTGCAAAA GGGGATCGAA CATCAGATGA AGCAGGGCAG CAAACTGACG      4320

TTTAGCGTCG ATACCTCGGC AAATCTGGAT CTGCGTGCCG GTATCAATCT GAACGAAGAC      4380

GGCAGTAAAC CAAATGGTGT CACTGCCCGT GTTTCTGCCG GCTAAGTGC ATCGGCAAAC       4440

CTGGCCGCCG GCTCGCGTGA ACGCAGCACC ACCTCTGGCC AGTTTGGCAG CACGACTTCG      4500

GCCAGCAATA ACCGCCCAAC CTTCCTCAAC GGGGTCGGCG CGGGTGCTAA CCTGACGGCT      4560

GCTTTAGGGG TTGCCCATTC ATCTACGCAT GAAGGGAAAC CGGTCGGGAT CTTCCCGGCA      4620

TTTACCTCGA CCAATGTTTC GGCAGCGCTG GCGCTGGATA ACCGTACCTC ACAGAGTATC      4680

AGCCTGGAAT TGAAGCGCGC GGAGCCGGTG ACCAGCAACG ATATCAGCGA GTTGACCTCC      4740

ACGCTGGGAA AACACTTTAA GGATAGCGCC ACAACGAAGA TGCTTGCCGC TCTCAAAGAG      4800

TTAGATGACG CTAAGCCCGC TGAACAACTG CATATTTTAC AGCAGCATTT CAGTGCAAAA      4860

GATGTCGTCG GTGATGAACG CTACGAGGCG GTGCGCAACC TGAAAAAACT GGTGATACGT      4920

CAACAGGCTG CGGACAGCCA CAGCATGGAA TTAGGATCTG CCAGTCACAG CACGACCTAC      4980

AATAATCTGT CGAGAATAAA TAATGACGGC ATTGTCGAGC TGCTACACAA ACATTTCGAT      5040

GCGGCATTAC CAGCAAGCAG TGCCAAACGT CTTGGTGAAA TGATGAATAA CGATCCGGCA      5100

CTGAAAGATA TTATTAAGCA GCTGCAAAGT ACGCCGTTCA GCAGCGCCAG CGTGTCGATG      5160

GAGCTGAAAG ATGGTCTGCG TGAGCAGACG GAAAAAGCAA TACTGGACGG TAAGGTCGGT      5220

CGTGAAGAAG TGGGAGTACT TTTCCAGGAT CGTAACAACT TGCGTGTTAA ATCGGTCAGC      5280

GTCAGTCAGT CCGTCAGCAA AAGCGAAGGC TTCAATACCC CAGCGCTGTT ACTGGGGACG      5340

AGCAACAGCG CTGCTATGAG CATGGAGCGC AACATCGGAA CCATTAATTT TAAATACGGC      5400

CAGGATCAGA ACACCCCACG GCGATTTACC CTGGAGGGTG GAATAGCTCA GGCTAATCCG      5460

CAGGTCGCAT CTGCGCTTAC TGATTTGAAG AAGGAAGGGC TGGAAATGAA GAGCTAA        5517
```

This DNA molecule is known as the dspE gene for *Erwinia amylovora*. This isolated DNA molecule of the present invention encodes a protein or polypeptide which elicits a plant pathogen's hypersensitive response having an amino acid sequence of SEQ. ID. No. 8 as follows:

```
Met Glu Leu Lys Ser Leu Gly Thr Glu His Lys Ala Ala Val His Thr
1               10                  15

Ala Ala His Asn Pro Val Gly His Gly Val Ala Leu Gln Gln Gly Ser
            20                  25                  30

Ser Ser Ser Ser Pro Gln Asn Ala Ala Ala Ser Leu Ala Ala Glu Gly
            35                  40                  45

Lys Asn Arg Gly Lys Met Pro Arg Ile His Gln Pro Ser Thr Ala Ala
        50              55                  60

Asp Gly Ile Ser Ala Ala His Gln Gln Lys Lys Ser Phe Ser Leu Arg
65                  70                  75                  80

Gly Cys Leu Gly Thr Lys Lys Phe Ser Arg Ser Ala Pro Gln Gly Gln
                85                  90                  95

Pro Gly Thr Thr His Ser Lys Gly Ala Thr Leu Arg Asp Leu Leu Ala
                100                 105                 110

Arg Asp Asp Gly Glu Thr Gln His Glu Ala Ala Ala Pro Asp Ala Ala
        115                 120                 125

Arg Leu Thr Arg Ser Gly Gly Val Lys Arg Arg Asn Met Asp Asp Met
        130                 135                 140

Ala Gly Arg Pro Met Val Lys Gly Gly Ser Gly Glu Asp Lys Val Pro
145                 150                 155                 160

Thr Gln Gln Lys Arg His Gln Leu Asn Asn Phe Gly Gln Met Arg Gln
                165                 170                 175

Thr Met Leu Ser Lys Met Ala His Pro Ala Ser Ala Asn Ala Gly Asp
                180                 185                 190

Arg Leu Gln His Ser Pro Pro His Ile Pro Gly Ser His His Glu Ile
        195                 200                 205

Lys Glu Glu Pro Val Gly Ser Thr Ser Lys Ala Thr Thr Ala His Ala
        210                 215                 220

Asp Arg Val Glu Ile Ala Gln Glu Asp Asp Asp Ser Glu Phe Gln Gln
225                 230                 235                 240

Leu His Gln Gln Arg Leu Ala Arg Glu Arg Glu Asn Pro Pro Gln Pro
                245                 250                 255

Pro Lys Leu Gly Val Ala Thr Pro Ile Ser Ala Arg Phe Gln Pro Lys
                260                 265                 270

Leu Thr Ala Val Ala Glu Ser Val Leu Glu Gly Thr Asp Thr Thr Gln
        275                 280                 285

Ser Pro Leu Lys Pro Gln Ser Met Leu Lys Gly Ser Gly Ala Gly Val
        290                 295                 300

Thr Pro Leu Ala Val Thr Leu Asp Lys Gly Lys Leu Gln Leu Ala Pro
305                 310                 315                 320

Asp Asn Pro Pro Ala Leu Asn Thr Leu Leu Lys Gln Thr Leu Gly Lys
                325                 330                 335

Asp Thr Gln His Tyr Leu Ala His His Ala Ser Ser Asp Gly Ser Gln
                340                 345                 350

His Leu Leu Leu Asp Asn Lys Gly His Leu Phe Asp Ile Lys Ser Thr
        355                 360                 365

Ala Thr Ser Tyr Ser Val Leu His Asn Ser His Pro Gly Glu Ile Lys
        370                 375                 380
```

```
Gly Lys Leu Ala Gln Ala Gly Thr Gly Ser Val Ser Val Asp Gly Lys
385                 390                 395                 400

Ser Gly Lys Ile Ser Leu Gly Ser Gly Thr Gln Ser His Asn Lys Thr
            405                 410                 415

Met Leu Ser Gln Pro Gly Glu Ala His Arg Ser Leu Leu Thr Gly Ile
                420                 425                 430

Trp Gln His Pro Ala Gly Ala Ala Arg Pro Gln Gly Glu Ser Ile Arg
        435                 440                 445

Leu His Asp Asp Lys Ile His Ile Leu His Pro Glu Leu Gly Val Trp
    450                 455                 460

Gln Ser Ala Asp Lys Asp Thr His Ser Gln Leu Ser Arg Gln Ala Asp
465                 470                 475                 480

Gly Lys Leu Tyr Ala Leu Lys Asp Asn Arg Thr Leu Gln Asn Leu Ser
                485                 490                 495

Asp Asn Lys Ser Ser Glu Lys Leu Val Asp Lys Ile Lys Ser Tyr Ser
            500                 505                 510

Val Asp Gln Arg Gly Gln Val Ala Ile Leu Thr Asp Thr Pro Gly Arg
                515                 520                 525

His Lys Met Ser Ile Met Pro Ser Leu Asp Ala Ser Pro Glu Ser His
    530                 535                 540

Ile Ser Leu Ser Leu His Phe Ala Asp Ala His Gln Gly Leu Leu His
545                 550                 555                 560

Gly Lys Ser Glu Leu Glu Ala Gln Ser Val Ala Ile Ser His Gly Arg
                565                 570                 575

Leu Val Val Ala Asp Ser Glu Gly Lys Leu Phe Ser Ala Ala Ile Pro
            580                 585                 590

Lys Gln Gly Asp Gly Asn Glu Leu Lys Met Lys Ala Met Pro Gln His
                595                 600                 605

Ala Leu Asp Glu His Phe Gly His Asp His Gln Ile Ser Gly Phe Phe
    610                 615                 620

His Asp Asp His Gly Gln Leu Asn Ala Leu Val Lys Asn Asn Phe Arg
625                 630                 635                 640

Gln Gln His Ala Cys Pro Leu Gly Asn Asp His Gln Phe His Pro Gly
                645                 650                 655

Trp Asn Leu Thr Asp Ala Leu Val Ile Asp Asn Gln Leu Gly Leu His
            660                 665                 670

His Thr Asn Pro Glu Pro His Glu Ile Leu Asp Met Gly His Leu Gly
                675                 680                 685

Ser Leu Ala Leu Gln Glu Gly Lys Leu His Tyr Phe Asp Gln Leu Thr
    690                 695                 700

Lys Gly Trp Thr Gly Ala Glu Ser Asp Cys Lys Gln Leu Lys Lys Gly
705                 710                 715                 720

Leu Asp Gly Ala Ala Tyr Leu Leu Lys Asp Gly Glu Val Lys Arg Leu
                725                 730                 735

Asn Ile Asn Gln Ser Thr Ser Ser Ile Lys His Gly Thr Glu Asn Val
            740                 745                 750

Phe Ser Leu Pro His Val Arg Asn Lys Pro Glu Pro Gly Asp Ala Leu
                755                 760                 765

Gln Gly Leu Asn Lys Asp Asp Lys Ala Gln Ala Met Ala Val Ile Gly
    770                 775                 780

Val Asn Lys Tyr Leu Ala Leu Thr Glu Lys Gly Asp Ile Arg Ser Phe
785                 790                 795                 800
```

```
                        -continued

Gln Ile Lys Pro Gly Thr Gln Gln Leu Glu Arg Pro Ala Gln Thr Leu
                805                 810                 815

Ser Arg Glu Gly Ile Ser Gly Glu Leu Lys Asp Ile His Val Asp His
            820                 825                 830

Lys Gln Asn Leu Tyr Ala Leu Thr His Glu Gly Glu Val Phe His Gln
            835                 840                 845

Pro Arg Glu Ala Trp Gln Asn Gly Ala Glu Ser Ser Trp His Lys
            850                 855                 860

Leu Ala Leu Pro Gln Ser Glu Ser Lys Leu Lys Ser Leu Asp Met Ser
865                 870                 875                 880

His Glu His Lys Pro Ile Ala Thr Phe Glu Asp Gly Ser Gln His Gln
                885                 890                 895

Leu Lys Ala Gly Gly Trp His Ala Tyr Ala Ala Pro Glu Arg Gly Pro
                900                 905                 910

Leu Ala Val Gly Thr Ser Gly Ser Gln Thr Val Phe Asn Arg Leu Met
                915                 920                 925

Gln Gly Val Lys Gly Lys Val Ile Pro Gly Ser Gly Leu Thr Val Lys
                930                 935                 940

Leu Ser Ala Gln Thr Gly Gly Met Thr Gly Ala Glu Gly Arg Lys Val
945                 950                 955                 960

Ser Ser Lys Phe Ser Glu Arg Ile Arg Ala Tyr Ala Phe Asn Pro Thr
                965                 970                 975

Met Ser Thr Pro Arg Pro Ile Lys Asn Ala Ala Tyr Ala Thr Gln His
                980                 985                 990

Gly Trp Gln Gly Arg Glu Gly Leu Lys Pro Leu Tyr Glu Met Gln Gly
                995                 1000                1005

Ala Leu Ile Lys Gln Leu Asp Ala His Asn Val Arg His Asn Ala Pro
                1010                1015                1020

Gln Pro Asp Leu Gln Ser Lys Leu Glu Thr Leu Asp Leu Gly Glu His
1025                1030                1035                1040

Gly Ala Glu Leu Leu Asn Asp Met Lys Arg Phe Arg Asp Glu Leu Glu
                1045                1050                1055

Gln Ser Ala Thr Arg Ser Val Thr Val Leu Gly Gln His Gln Gly Val
                1060                1065                1070

Leu Lys Ser Asn Gly Glu Ile Asn Ser Glu Phe Lys Pro Ser Pro Gly
                1075                1080                1085

Lys Ala Leu Val Gln Ser Phe Asn Val Asn Arg Ser Gly Gln Asp Leu
                1090                1095                1100

Ser Lys Ser Leu Gln Gln Ala Val His Ala Thr Pro Pro Ser Ala Glu
1105                1110                1115                1120

Ser Lys Leu Gln Ser Met Leu Gly His Phe Val Ser Ala Gly Val Asp
                1125                1130                1135

Met Ser His Gln Lys Gly Glu Ile Pro Leu Gly Arg Gln Arg Asp Pro
                1140                1145                1150

Asn Asp Lys Thr Ala Leu Thr Lys Ser Arg Leu Ile Leu Asp Thr Val
                1155                1160                1165

Thr Ile Gly Glu Leu His Glu Leu Ala Asp Lys Ala Lys Leu Val Ser
                1170                1175                1180

Asp His Lys Pro Asp Ala Asp Gln Ile Lys Gln Leu Arg Gln Gln Phe
1185                1190                1195                1200

Asp Thr Leu Arg Glu Lys Arg Tyr Glu Ser Asn Pro Val Lys His Tyr
                1205                1210                1215
```

-continued

```
Thr Asp Met Gly Phe Thr His Asn Lys Ala Leu Glu Ala Asn Tyr Asp
        1220                1225                1230

Ala Val Lys Ala Phe Ile Asn Ala Phe Lys Lys Glu His His Gly Val
            1235                1240                1245

Asn Leu Thr Thr Arg Thr Val Leu Glu Ser Gln Gly Ser Ala Glu Leu
        1250                1255                1260

Ala Lys Lys Leu Lys Asn Thr Leu Leu Ser Leu Asp Ser Gly Glu Ser
1265                1270                1275                1280

Met Ser Phe Ser Arg Ser Tyr Gly Gly Val Ser Thr Val Phe Val
                1285                1290                1295

Pro Thr Leu Ser Lys Lys Val Pro Val Pro Val Ile Pro Gly Ala Gly
            1300                1305                1310

Ile Thr Leu Asp Arg Ala Tyr Asn Leu Ser Phe Ser Arg Thr Ser Gly
        1315                1320                1325

Gly Leu Asn Val Ser Phe Gly Arg Asp Gly Val Ser Gly Asn Ile
        1330                1335                1340

Met Val Ala Thr Gly His Asp Val Met Pro Tyr Met Thr Gly Lys Lys
1345                1350                1355                1360

Thr Ser Ala Gly Asn Ala Ser Asp Trp Leu Ser Ala Lys His Lys Ile
            1365                1370                1375

Ser Pro Asp Leu Arg Ile Gly Ala Ala Val Ser Gly Thr Leu Gln Gly
            1380                1385                1390

Thr Leu Gln Asn Ser Leu Lys Phe Lys Leu Thr Glu Asp Glu Leu Pro
        1395                1400                1405

Gly Phe Ile His Gly Leu Thr His Gly Thr Leu Thr Pro Ala Glu Leu
        1410                1415                1420

Leu Gln Lys Gly Ile Glu His Gln Met Lys Gln Gly Ser Lys Leu Thr
1425                1430                1435                1440

Phe Ser Val Asp Thr Ser Ala Asn Leu Asp Leu Arg Ala Gly Ile Asn
            1445                1450                1455

Leu Asn Glu Asp Gly Ser Lys Pro Asn Gly Val Thr Ala Arg Val Ser
            1460                1465                1470

Ala Gly Leu Ser Ala Ser Ala Asn Leu Ala Ala Gly Ser Arg Glu Arg
            1475                1480                1485

Ser Thr Thr Ser Gly Gln Phe Gly Ser Thr Thr Ser Ala Ser Asn Asn
        1490                1495                1500

Arg Pro Thr Phe Leu Asn Gly Val Gly Ala Gly Ala Asn Leu Thr Ala
1505                1510                1515                1520

Ala Leu Gly Val Ala His Ser Ser Thr His Glu Gly Lys Pro Val Gly
            1525                1530                1535

Ile Phe Pro Ala Phe Thr Ser Thr Asn Val Ser Ala Ala Leu Ala Leu
            1540                1545                1550

Asp Asn Arg Thr Ser Gln Ser Ile Ser Leu Glu Leu Lys Arg Ala Glu
        1555                1560                1565

Pro Val Thr Ser Asn Asp Ile Ser Glu Leu Thr Ser Thr Leu Gly Lys
        1570                1575                1595

His Phe Lys Asp Ser Ala Thr Thr Lys Met Leu Ala Ala Leu Lys Glu
1585                1590                1595                1600

Leu Asp Asp Ala Lys Pro Ala Glu Gln Leu His Ile Leu Gln Gln His
                1605                1610                1615

Phe Ser Ala Lys Asp Val Val Gly Asp Glu Arg Tyr Glu Ala Val Arg
            1620                1625                1630
```

-continued

```
Asn Leu Lys Lys Leu Val Ile Arg Gln Gln Ala Ala Asp Ser His Ser
        1635                1640                1645

Met Glu Leu Gly Ser Ala Ser His Ser Thr Thr Tyr Asn Asn Leu Ser
        1650                1655                1660

Arg Ile Asn Asn Asp Gly Ile Val Glu Leu Leu His Lys His Phe Asp
1665                1670                1675                1680

Ala Ala Leu Pro Ala Ser Ser Ala Lys Arg Leu Gly Glu Met Met Asn
                1685                1690                1695

Asn Asp Pro Ala Leu Lys Asp Ile Ile Lys Gln Leu Gln Ser Thr Pro
            1700                1705                1710

Phe Ser Ser Ala Ser Val Ser Met Glu Leu Lys Asp Gly Leu Arg Glu
        1715                1720                1725

Gln Thr Glu Lys Ala Ile Leu Asp Gly Lys Val Gly Arg Glu Glu Val
        1730                1735                1740

Gly Val Leu Phe Gln Asp Arg Asn Asn Leu Arg Val Lys Ser Val Ser
1745                1750                1755                1760

Val Ser Gln Ser Val Ser Lys Ser Glu Gly Phe Asn Thr Pro Ala Leu
                1765                1770                1775

Leu Leu Gly Thr Ser Asn Ser Ala Ala Met Ser Met Glu Arg Asn Ile
            1780                1785                1790

Gly Thr Ile Asn Phe Lys Tyr Gly Gln Asp Gln Asn Thr Pro Arg Arg
        1795                1800                1805

Phe Thr Leu Glu Gly Gly Ile Ala Gln Ala Asn Pro Gln Val Ala Ser
        1810                1815                1820

Ala Leu Thr Asp Leu Lys Lys Glu Gly Leu Glu Met Lys Ser
1825                1830                1835
```

This protein or polypeptide is about 198 kDa and has a pI of 8.98.

The present invention relates to an isolated DNA molecule having a nucleotide sequence of SEQ. ID. No. 9 as follows:

```
ATGACATCGT CACAGCAGCG GGTTGAAAGG TTTTTACAGT ATTTCTCCGC CGGGTGTAAA    60

ACGCCCATAC ATCTGAAAGA CGGGGTGTGC GCCCTGTATA ACGAACAAGA TGAGGAGGCG   120

GCGGTGCTGG AAGTACCGCA ACACAGCGAC AGCCTGTTAC TACACTGCCG AATCATTGAG   180

GCTGACCCAC AAACTTCAAT AACCCTGTAT TCGATGCTAT TACAGCTGAA TTTTGAAATG   240

GCGGCCATGC GCGGCTGTTG GCTGGCGCTG GATGAACTGC ACAACGTGCG TTTATGTTTT   300

CAGCAGTCGC TGGAGCATCT GGATGAAGCA AGTTTTAGCG ATATCGTTAG CGGCTTCATC   360

GAACATGCGG CAGAAGTGCG TGAGTATATA GCGCAATTAG ACGAGAGTAG CGCGGCATAA   420
```

This is known as the dspF gene. This isolated DNA molecule of the present invention encodes a hypersensitive response elicitor protein or polypeptide having an amino acid sequence of SEQ. ID. No. 10 as follows:

```
Met Thr Ser Ser Gln Gln Arg Val Glu Arg Phe Leu Gln Tyr Phe Ser
1               5                   10                  15

Ala Gly Cys Lys Thr Pro Ile His Leu Lys Asp Gly Val Cys Ala Leu
                20                  25                  30
```

-continued

```
Tyr Asn Glu Gln Asp Glu Glu Ala Ala Val Leu Glu Val Pro Gln His
        35              40                  45

Ser Asp Ser Leu Leu Leu His Cys Arg Ile Ile Glu Ala Asp Pro Gln
        50              55                  60

Thr Ser Ile Thr Leu Tyr Ser Met Leu Leu Gln Leu Asn Phe Glu Met
65              70                  75                      80

Ala Ala Met Arg Gly Cys Trp Leu Ala Leu Asp Glu Leu His Asn Val
            85                  90                  95

Arg Leu Cys Phe Gln Gln Ser Leu Glu His Leu Asp Glu Ala Ser Phe
            100                 105                 110

Ser Asp Ile Val Ser Gly Phe Ile Glu His Ala Ala Glu Val Arg Glu
            115                 120                 125

Tyr Ile Ala Gln Leu Asp Glu Ser Ser Ala Ala
            130                 135
                                                        20
```

This protein or polypeptide is about 16 kDa and has a pI of 4.45.

The hypersensitive response elicitor polypeptide or protein derived from *Pseudomonas syringae* has an amino acid sequence corresponding to SEQ. ID. No. 11 as follows:

```
Met Gln Ser Leu Ser Leu Asn Ser Ser Ser Leu Gln Thr Pro Ala Met
1               5                   10                  15

Ala Leu Val Leu Val Arg Pro Glu Ala Glu Thr Thr Gly Ser Thr Ser
            20                  25                  30

Ser Lys Ala Leu Gln Glu Val Val Lys Leu Ala Glu Glu Leu Met
        35                  40                  45

Arg Asn Gly Gln Leu Asp Asp Ser Ser Pro Leu Gly Lys Leu Leu Ala
        50                  55                  60

Lys Ser Met Ala Ala Asp Gly Lys Ala Gly Gly Ile Glu Asp Val
65                  70                  75                  80

Ile Ala Ala Leu Asp Lys Leu Ile His Glu Lys Leu Gly Asp Asn Phe
            85                  90                  95

Gly Ala Ser Ala Asp Ser Ala Ser Gly Thr Gly Gln Gln Asp Leu Met
            100                 105                 110

Thr Gln Val Leu Asn Gly Leu Ala Lys Ser Met Leu Asp Asp Leu Leu
            115                 120                 125

Thr Lys Gln Asp Gly Gly Thr Ser Phe Ser Glu Asp Asp Met Pro Met
        130                 135                 140

Leu Asn Lys Ile Ala Gln Phe Met Asp Asp Asn Pro Ala Gln Phe Pro
145                 150                 155                 160

Lys Pro Asp Ser Gly Ser Trp Val Asn Glu Leu Lys Glu Asp Asn Phe
            165                 170                 175

Leu Asp Gly Asp Glu Thr Ala Ala Phe Arg Ser Ala Leu Asp Ile Ile
            180                 185                 190

Gly Gln Gln Leu Gly Asn Gln Gln Ser Asp Ala Gly Ser Leu Ala Gly
            195                 200                 205

Thr Gly Gly Gly Leu Gly Thr Pro Ser Ser Phe Ser Asn Asn Ser Ser
            210                 215                 220

Val Met Gly Asp Pro Leu Ile Asp Ala Asn Thr Gly Pro Gly Asp Ser
225                 230                 235                 240

Gly Asn Thr Arg Gly Glu Ala Gly Gln Leu Ile Gly Glu Leu Ile Asp
            245                 250                 255
```

```
Arg Gly Leu Gln Ser Val Leu Ala Gly Gly Gly Leu Gly Thr Pro Val
            260                 265                 270

Asn Thr Pro Gln Thr Gly Thr Ser Ala Asn Gly Gly Gln Ser Ala Gln
            275                 280                 285

Asp Leu Asp Gln Leu Leu Gly Gly Leu Leu Leu Lys Gly Leu Glu Ala
    290                 295                 300

Thr Leu Lys Asp Ala Gly Gln Thr Gly Thr Asp Val Gln Ser Ser Ala
305                 310                 315                 320

Ala Gln Ile Ala Thr Leu Leu Val Ser Thr Leu Leu Gln Gly Thr Arg
            325                 330                 335

Asn Gln Ala Ala Ala
            340
```

This hypersensitive response elicitor polypeptide or protein has a molecular weight of 34–35 kDa. It is rich in glycine (about 13.5%) and lacks cysteine and tyrosine. Further information about the hypersensitive response elicitor derived from *Pseudomonas syringae* is found in He, S. Y., H. C. Huang, and A. Collmer, "*Pseudomonas syringae* pv. syringae Harpin$_{Pss}$: a Protein that is Secreted via the Hrp Pathway and Elicits the Hypersensitive Response in Plants," *Cell* 73:1255–1266 (1993), which is hereby incorporated by reference. The DNA molecule encoding the hypersensitive response elicitor from *Pseudomonas syringae* has a nucleotide sequence corresponding to SEQ. ID. No. 12 as follows:

```
ATGCAGAGTC TCAGTCTTAA CAGCAGCTCG CTGCAAACCC CGGCAATGGC CCTTGTCCTG    60

GTACGTCCTG AAGCCGAGAC GACTGGCAGT ACGTCGAGCA AGGCGCTTCA GGAAGTTGTC   120

GTGAAGCTGG CCGAGGAACT GATGCGCAAT GGTCAACTCG ACGACAGCTC GCCATTGGGA   180

AAACTGTTGG CCAAGTCGAT GGCCGCAGAT GGCAAGGCGG GCGGCGGTAT TGAGGATGTC   240

ATCGCTGCGC TGGACAAGCT GATCCATGAA AAGCTCGGTG ACAACTTCGG CGCGTCTGCG   300

GACAGCGCCT CGGGTACCGG ACAGCAGGAC CTGATGACTC AGGTGCTCAA TGGCCTGGCC   360

AAGTCGATGC TCGATGATCT TCTGACCAAG CAGGATGGCG GGACAAGCTT CTCCGAAGAC   420

GATATGCCGA TGCTGAACAA GATCGCGCAG TTCATGGATG ACAATCCCGC ACAGTTTCCC   480

AAGCCGGACT CGGGCTCCTG GGTGAACGAA CTCAAGGAAG ACAACTTCCT TGATGGCGAC   540

GAAACGGCTG CGTTCCGTTC GGCACTCGAC ATCATTGGCC AGCAACTGGG TAATCAGCAG   600

AGTGACGCTG GCAGTCTGGC AGGGACGGGT GGAGGTCTGG GCACTCCGAG CAGTTTTTCC   660

AACAACTCGT CCGTGATGGG TGATCCGCTG ATCGACGCCA ATACCGGTCC CGGTGACAGC   720

GGCAATACCC GTGGTGAAGC GGGGCAACTG ATCGGCGAGC TTATCGACCG TGGCCTGCAA   780

TCGGTATTGG CCGGTGGTGG ACTGGGCACA CCCGTAAACA CCCCGCAGAC CGGTACGTCG   840

GCGAATGGCG GACAGTCCGC TCAGGATCTT GATCAGTTGC TGGGCGGCTT GCTGCTCAAG   900

GGCCTGGAGG CAACGCTCAA GGATGCCGGG CAAACAGGCA CCGACGTGCA GTCGAGCGCT   960

GCGCAAATCG CCACCTTGCT GGTCAGTACG CTGCTGCAAG GCACCCGCAA TCAGGCTGCA  1020

GCCTGA                                                            1026
```

Another potentially suitable hypersensitive response elicitor from *Pseudomonas syringae* is disclosed in U.S. patent application Ser. No. 09/120,817, which is hereby incorporated by reference. The protein has a nucleotide sequence of SEQ. ID. No. 13 as follows:

```
TCCACTTCGC TGATTTTGAA ATTGGCAGAT TCATAGAAAC GTTCAGGTGT GGAAATCAGG    60
CTGAGTGCGC AGATTTCGTT GATAAGGGTG TGGTACTGGT CATTGTTGGT CATTTCAAGG   120
CCTCTGAGTG CGGTGCGGAG CAATACCAGT CTTCCTGCTG GCGTGTGCAC ACTGAGTCGC   180
AGGCATAGGC ATTTCAGTTC CTTGCGTTGG TTGGGCATAT AAAAAAAGGA ACTTTTAAAA   240
ACAGTGCAAT GAGATGCCGG CAAAACGGGA ACCGGTCGCT GCGCTTTGCC ACTCACTTCG   300
AGCAAGCTCA ACCCCAAACA TCCACATCCC TATCGAACGG ACAGCGATAC GGCCACTTGC   360
TCTGGTAAAC CCTGGAGCTG GCGTCGGTCC AATTGCCCAC TTAGCGAGGT AACGCAGCAT   420
GAGCATCGGC ATCACACCCC GGCCGCAACA GACCACCACG CCACTCGATT TTTCGGCGCT   480
AAGCGGCAAG AGTCCTCAAC CAAACACGTT CGGCGAGCAG AACACTCAGC AAGCGATCGA   540
CCCGAGTGCA CTGTTGTTCG GCAGCGACAC ACAGAAAGAC GTCAACTTCG GCACGCCCGA   600
CAGCACCGTC CAGAATCCGC AGGACGCCAG CAAGCCCAAC GACAGCCAGT CCAACATCGC   660
TAAATTGATC AGTGCATTGA TCATGTCGTT GCTGCAGATG CTCACCAACT CCAATAAAAA   720
GCAGGACACC AATCAGGAAC AGCCTGATAG CCAGGCTCCT TTCCAGAACA ACGGCGGGCT   780
CGGTACACCG TCGGCCGATA GCGGGGGCGG CGGTACACCG GATGCGACAG GTGGCGGCGG   840
CGGTGATACG CCAAGCGCAA CAGGCGGTGG CGGCGGTGAT ACTCCGACCG CAACAGGCGG   900
TGGCGGCAGC GGTGGCGGCG GCACACCCAC TGCAACAGGT GGCGGCAGCG GTGGCACACC   960
CACTGCAACA GGCGGTGGCG AGGGTGGCGT AACACCGCAA ATCACTCCGC AGTTGGCCAA  1020
CCCTAACCGT ACCTCAGGTA CTGGCTCGGT GTCGGACACC GCAGGTTCTA CCGAGCAAGC  1080
CGGCAAGATC AATGTGGTGA AAGACACCAT CAAGGTCGGC GCTGGCGAAG TCTTTGACGG  1140
CCACGGCGCA ACCTTCACTG CCGACAAATC TATGGGTAAC GGAGACCAGG GCGAAAATCA  1200
GAAGCCCATG TTCGAGCTGG CTGAAGGCGC TACGTTGAAG AATGTGAACC TGGGTGAGAA  1260
CGAGGTCGAT GGCATCCACG TGAAAGCCAA AAACGCTCAG GAAGTCACCA TTGACAACGT  1320
GCATGCCCAG AACGTCGGTG AAGACCTGAT TACGGTCAAA GGCGAGGGAG CGCAGCGGT   1380
CACTAATCTG AACATCAAGA ACAGCAGTGC CAAAGGTGCA GACGACAAGG TTGTCCAGCT  1440
CAACGCCAAC ACTCACTTGA AAATCGACAA CTTCAAGGCC GACGATTTCG GCACGATGGT  1500
TCGCACCAAC GGTGGCAAGC AGTTTGATGA CATGAGCATC GAGCTGAACG GCATCGAAGC  1560
TAACCACGGC AAGTTCGCCC TGGTGAAAAG CGACAGTGAC GATCTGAAGC TGGCAACGGG  1620
CAACATCGCC ATGACCGACG TCAAACACGC CTACGATAAA ACCCAGGCAT CGACCCAACA  1680
CACCGAGCTT TGAATCCAGA CAAGTAGCTT GAAAAAAGGG GGTGGACTC              1729
```

This DNA molecule is known as the dspE gene for *Pseudomonas syringae*. This isolated DNA molecule of the present invention encodes a protein or polypeptide which elicits a plant pathogen's hypersensitive response having an amino acid sequence of SEQ. ID. No. 14 as follows:

```
Met Ser Ile Gly Ile Thr Pro Arg Pro Gln Gln Thr Thr Thr Pro Leu
1               5                   10                  15

Asp Phe Ser Ala Leu Ser Gly Lys Ser Pro Gln Pro Asn Thr Phe Gly
            20                  25                  30
```

```
Glu Gln Asn Thr Gln Gln Ala Ile Asp Pro Ser Ala Leu Leu Phe Gly
         35                  40                  45

Ser Asp Thr Gln Lys Asp Val Asn Phe Gly Thr Pro Asp Ser Thr Val
     50                  55                  60

Gln Asn Pro Gln Asp Ala Ser Lys Pro Asn Asp Ser Gln Ser Asn Ile
65                   70                  75                  80

Ala Lys Leu Ile Ser Ala Leu Ile Met Ser Leu Leu Gln Met Leu Thr
                 85                  90                  95

Asn Ser Asn Lys Lys Gln Asp Thr Asn Gln Glu Gln Pro Asp Ser Gln
             100                 105                 111

Ala Pro Phe Gln Asn Asn Gly Gly Leu Gly Thr Pro Ser Ala Asp Ser
             115                 120                 125

Gly Gly Gly Gly Thr Pro Asp Ala Thr Gly Gly Gly Gly Asp Thr
             130                 135                 140

Pro Ser Ala Thr Gly Gly Gly Gly Asp Thr Pro Thr Ala Thr Gly
145                 150                 155                 160

Gly Gly Gly Ser Gly Gly Gly Thr Pro Thr Ala Thr Gly Gly Gly
                 165                 170                 175

Ser Gly Gly Thr Pro Thr Ala Thr Gly Gly Glu Gly Gly Val Thr
             180                 185                 190

Pro Gln Ile Thr Pro Gln Leu Ala Asn Pro Asn Arg Thr Ser Gly Thr
             195                 200                 205

Gly Ser Val Ser Asp Thr Ala Gly Ser Thr Glu Gln Ala Gly Lys Ile
     210                 215                 220

Asn Val Val Lys Asp Thr Ile Lys Val Gly Ala Gly Glu Val Phe Asp
225                 230                 235                 240

Gly His Gly Ala Thr Phe Thr Ala Asp Lys Ser Met Gly Asn Gly Asp
                 245                 250                 255

Gln Gly Glu Asn Gln Lys Pro Met Phe Glu Leu Ala Glu Gly Ala Thr
             260                 265                 270

Leu Lys Asn Val Asn Leu Gly Glu Asn Glu Val Asp Gly Ile His Val
             275                 280                 285

Lys Ala Lys Asn Ala Gln Glu Val Thr Ile Asp Asn Val His Ala Gln
     290                 295                 300

Asn Val Gly Glu Asp Leu Ile Thr Val Lys Gly Glu Gly Gly Ala Ala
305                 310                 315                 320

Val Thr Asn Leu Asn Ile Lys Asn Ser Ser Ala Lys Gly Ala Asp Asp
             325                 330                 335

Lys Val Gln Leu Asn Ala Asn Thr His Leu Lys Ile Asp Asn Phe
             340                 345                 350

Lys Ala Asp Asp Phe Gly Thr Met Val Arg Thr Asn Gly Gly Lys Gln
     355                 360                 365

Phe Asp Asp Met Ser Ile Glu Leu Asn Gly Ile Glu Ala Asn His Gly
     370                 375                 380

Lys Phe Ala Leu Val Lys Ser Asp Ser Asp Leu Lys Leu Ala Thr
385                 390                 395                 400

Gly Asn Ile Ala Met Thr Asp Val Lys His Ala Tyr Asp Lys Thr Gln
             405                 410                 415

Ala Ser Thr Gln His Thr Glu Leu
             420
```

This protein or polypeptide is about 42.9 kDa.

The hypersensitive response elicitor polypeptide or protein derived from *Pseudomonas solanacearum* has an amino acid sequence corresponding to SEQ. ID. No. 15 as follows:

```
Met Ser Val Gly Asn Ile Gln Ser Pro Ser Asn Leu Pro Gly Leu Gln
1               5                   10                  15

Asn Leu Asn Leu Asn Thr Asn Thr Asn Ser Gln Gln Ser Gly Gln Ser
            20                  25                  30

Val Gln Asp Leu Ile Lys Gln Val Glu Lys Asp Ile Leu Asn Ile Ile
        35                  40                  45

Ala Ala Leu Val Gln Lys Ala Ala Gln Ser Ala Gly Gly Asn Thr Gly
    50                  55                  60

Asn Thr Gly Asn Ala Pro Ala Lys Asp Gly Asn Ala Asn Ala Gly Ala
65                  70                  75                  80

Asn Asp Pro Ser Lys Asn Asp Pro Ser Lys Ser Gln Ala Pro Gln Ser
                85                  90                  95

Ala Asn Lys Thr Gly Asn Val Asp Asp Ala Asn Asn Gln Asp Pro Met
            100                 105                 110

Gln Ala Leu Met Gln Leu Leu Glu Asp Leu Val Lys Leu Leu Lys Ala
        115                 120                 125

Ala Leu His Met Gln Gln Pro Gly Gly Asn Asp Lys Gly Asn Gly Val
    130                 135                 140

Gly Gly Ala Asn Gly Ala Lys Gly Ala Gly Gly Gln Gly Gly Leu Ala
145                 150                 155                 160

Glu Ala Leu Gln Glu Ile Glu Gln Ile Leu Ala Gln Leu Gly Gly Gly
                165                 170                 175

Gly Ala Gly Ala Gly Gly Ala Gly Gly Gly Val Gly Gly Ala Gly Gly
            180                 185                 190

Ala Asp Gly Gly Ser Gly Ala Gly Gly Ala Gly Gly Ala Asn Gly Ala
        195                 200                 205

Asp Gly Gly Asn Gly Val Asn Gly Asn Gln Ala Asn Gly Pro Gln Asn
    210                 215                 220

Ala Gly Asp Val Asn Gly Ala Asn Gly Ala Asp Asp Gly Ser Glu Asp
225                 230                 235                 240

Gln Gly Gly Leu Thr Gly Val Leu Gln Lys Leu Met Lys Ile Leu Asn
                245                 250                 255

Ala Leu Val Gln Met Met Gln Gln Gly Gly Leu Gly Gly Gly Asn Gln
            260                 265                 270

Ala Gln Gly Gly Ser Lys Gly Ala Gly Asn Ala Ser Pro Ala Ser Gly
        275                 280                 285

Ala Asn Pro Gly Ala Asn Gln Pro Gly Ser Ala Asp Asp Gln Ser Ser
    290                 295                 300

Gly Gln Asn Asn Leu Gln Ser Gln Ile Met Asp Val Val Lys Glu Val
305                 310                 315                 320

Val Gln Ile Leu Gln Gln Met Leu Ala Ala Gln Asn Gly Gly Ser Gln
                325                 330                 335

Gln Ser Thr Ser Thr Gln Pro Met
            340
```

It is encoded by a DNA molecule having a nucleotide sequence corresponding SEQ. ID. No. 16 as follows:

```
ATGTCAGTCG GAAACATCCA GAGCCCGTCG AACCTCCCGG GTCTGCAGAA CCTGAACCTC    60

AACACCAACA CCAACAGCCA GCAATCGGGC CAGTCCGTGC AAGACCTGAT CAAGCAGGTC   120

GAGAAGGACA TCCTCAACAT CATCGCAGCC CTCGTGCAGA AGGCCGCACA GTCGGCGGGC   180

GGCAACACCG GTAACACCGG CAACGCGCCG GCGAAGGACG GCAATGCCAA CGCGGGCGCC   240

AACGACCCGA GCAAGAACGA CCCGAGCAAG AGCCAGGCTC CGCAGTCGGC CAACAAGACC   300

GGCAACGTCG ACGACGCCAA CAACCAGGAT CCGATGCAAG CGCTGATGCA GCTGCTGGAA   360

GACCTGGTGA AGCTGCTGAA GGCGGCCCTG CACATGCAGC AGCCCGGCGG CAATGACAAG   420

GGCAACGGCG TGGGCGGTGC CAACGGCGCC AAGGGTGCCG GCGGCCAGGG CGGCCTGGCC   480

GAAGCGCTGC AGGAGATCGA GCAGATCCTC GCCCAGCTCG GCGGCGGCGG TGCTGGCGCC   540

GGCGGCGCGG GTGGCGGTGT CGGCGGTGCT GGTGGCGCGG ATGGCGGCTC CGGTGCGGGT   600

GGCGCAGGCG GTGCGAACGG CGCCGACGGC GGCAATGGCG TGAACGGCAA CCAGGCGAAC   660

GGCCCGCAGA ACGCAGGCGA TGTCAACGGT GCCAACGGCG CGGATGACGG CAGCGAAGAC   720

CAGGGCGGCC TCACCGGCGT GCTGCAAAAG CTGATGAAGA TCCTGAACGC GCTGGTGCAG   780

ATGATGCAGC AAGGCGGCCT CGGCGGCGGC AACCAGGCGC AGGGCGGCTC GAAGGGTGCC   840

GGCAACGCCT CGCCGGCTTC CGGCGCGAAC CCGGGCGCGA ACCAGCCCGG TTCGGCGGAT   900

GATCAATCGT CCGGCCAGAA CAATCTGCAA TCCCAGATCA TGGATGTGGT GAAGGAGGTC   960

GTCCAGATCC TGCAGCAGAT GCTGGCGGCG CAGAACGGCG GCAGCCAGCA GTCCACCTCG  1020

ACGCAGCCGA TGTAA                                                   1035
```

Further information regarding the hypersensitive response elicitor polypeptide or protein derived from *Pseudomonas solanacearum* is set forth in Arlat, M., F. Van Gijsegem, J. C. Huet, J. C. Pemollet, and C. A. Boucher, "PopA1, a Protein which Induces a Hypersensitive-like Response in Specific Petunia Genotypes, is Secreted via the Hrp Pathway of *Pseudomonas solanacearum*," *EMBO J.* 13:543–533 (1994), which is hereby incorporated by reference.

The hypersensitive response elicitor polypeptide or protein from *Xanthomonas campestris* pv. glycines has an amino acid sequence corresponding to SEQ. ID. No. 17 as follows:

```
Thr Leu Ile Glu Leu Met Ile Val Val Ala Ile Ile Ala Ile Leu Ala
1               5                  10                  15

Ala Ile Ala Leu Pro Ala Tyr Gln Asp Tyr
                20              25
```

This sequence is an amino terminal sequence having only 26 residues from the hypersensitive response elicitor polypeptide or protein of *Xanthomonas campestris* pv. glycines. It matches with fimbrial subunit proteins determined in other *Xanthomonas campestris* pathovars.

The hypersensitive response elicitor polypeptide or protein from *Xanthomonas campestris* pv. pelargonii is heat stable, protease sensitive, and has a molecular weight of 20 kDa. It includes an amino acid sequence corresponding to SEQ. ID. No. 18 as follows:

```
Ser Ser Gln Gln Ser Pro Ser Ala Gly Ser Glu Gln Gln Leu Asp Gln
1               5                  10                  15

Leu Leu Ala Met
            20
```

Isolation of *Erwinia carotovora* hypersensitive response elictor protein or polypeptide is described in Cui et al., "The RsmA Mutants of *Erwinia carotovora* subsp. carotovora Strain Ecc71 Overexpress hrp $N_{Ecc}$ and Elicit a Hypersensitive Reaction-like Response in Tobacco Leaves," *MPMI*, 9(7):565–73 (1996), which is hereby incorporated by reference. The hypersensitive response elicitor protein or polypeptide of *Erwinia stewartii* is set forth in Ahmad et al., "Harpin is Not Necessary for the Pathogenicity of *Erwinia stewartii* on Maize," 8*th Int'l. Cong. Molec. Plant-Microbe Interact.*, Jul. 14–19, 1996 and Ahmad, et al., "Harpin is Not Necessary for the Pathogenicity of *Erwinia stewartii* on Maize," *Ann. Mtg. Am. Phytopath. Soc.*, Jul. 27–31, 1996, which are hereby incorporated by reference.

Hypersensitive response elicitor proteins or polypeptides from *Phytophthora parasitica, Phytophthora cryptogea, Phytophthora cinnamoni, Phytophthora capsici, Phytophthora megasperma,* and *Phytophora citrophthora* are described in Kaman, et al., "Extracellular Protein Elicitors from Phytophthora: Most Specificity and Induction of Resistance to Bacterial and Fungal Phytopathogens," *Molec. Plant-Microbe Interact.*, 6(1):15–25 (1993), Ricci et al., "Structure and Activity of Proteins from Pathogenic Fungi Phytophthora Eliciting Necrosis and Acquired Resistance in Tobacco," *Eur. J. Biochem.*, 183:555–63 (1989), Ricci et al., "Differential Production of Parasiticein, and Elicitor of Necrosis and Resistance in Tobacco, by Isolates of Phytophthora parasitica," *Plant Path.* 41:298–307 (1992), Baillreul et al, "A New Elicitor of the Hypersensitive Response in Tobacco: A Fungal Glycoprotein Elicits Cell Death, Expression of Defence Genes, Production of Salicylic Acid, and Induction of Systemic Acquired Resistance," *Plant J.*, 8(4) :551–60 (1995), and Bonnet et al., "Acquired Resistance Triggered by Elicitors in Tobacco and Other Plants," *Eur. J. Plant Path.*, 102:181–92 (1996), which are hereby incorporated by reference.

Another hypersensitive response elicitor in accordance with the present invention is from *Clavibacter michiganensis* subsp. sepedonicus which is fully described in U.S. patent application Ser. No. 09/136,625, which is hereby incorporated by reference.

The above elicitors are exemplary. Other elicitors can be identified by growing fungi or bacteria that elicit a hypersensitive response under conditions which genes encoding an elicitor are expressed. Cell-free preparations from culture supernatants can be tested for elicitor activity (i.e. local necrosis) by using them to infiltrate appropriate plant tissues.

Fragments of the above hypersensitive response elicitor polypeptides or proteins as well as fragments of full length elicitors from other pathogens are encompassed by the method of the present invention.

Suitable fragments can be produced by several means. In the first, subclones of the gene encoding a known elicitor protein are produced by conventional molecular genetic manipulation by subcloning gene fragments. The subclones then are expressed in vitro or in vivo in bacterial cells to yield a smaller protein or peptide that can be tested for elicitor activity according to the procedure described below.

As an alternative, fragments of an elicitor protein can be produced by digestion of a full-length elicitor protein with proteolytic enzymes like chymotrypsin or Staphylococcus proteinase A, or trypsin. Different proteolytic enzymes are likely to cleave elicitor proteins at different sites based on the amino acid sequence of the elicitor protein. Some of the fragments that result from proteolysis may be active elicitors of resistance.

In another approach, based on knowledge of the primary structure of the protein, fragments of the elicitor protein gene may be synthesized by using the PCR technique together with specific sets of primers chosen to represent particular portions of the protein. These then would be cloned into an appropriate vector for expression of a truncated peptide or protein.

Chemical synthesis can also be used to make suitable fragments. Such a synthesis is carried out using known amino acid sequences for the elicitor being produced. Alternatively, subjecting a full length elicitor to high temperatures and pressures will produce fragments. These fragments can then be separated by conventional procedures (e.g., chromatography, SDS-PAGE).

An example of suitable fragments of a hypersensitive response elicitor which do not elicit a hypersensitive response include fragments of the Erwinia. Suitable fragments include a C-terminal fragment of the amino acid sequence of SEQ. ID. No. 3, an N-terminal fragment of the amino acid sequence of SEQ. ID. No. 3, or an internal fragment of the amino acid sequence of SEQ. ID. No. 3. The C-terminal fragment of the amino acid sequence of SEQ. ID. No.3 can span the following amino acids of SEQ. ID. No. 3: 169 and 403,210 and 403,267 and 403, or 343 and 403. The internal fragment of the amino acid sequence of SEQ. ID. No. 3 can span the following amino acids of SEQ. ID. No. 3: 105 and 179, 137 and 166, 121 and 150, or 137 and 156. Other suitable fragments can be identified in accordance with the present invention.

Another example of suitable fragments of a hypersensitive response elicitor which do elicit a hypersensitive response are *Erwinia amylovora* fragments including a C-terminal fragment of the amino acid sequence of SEQ. ID. No. 3, an N-terminal fragment of the amino acid sequence of SEQ. ID. No. 3, or an internal fragment of the amino acid sequence of SEQ. ID. No. 3. The C-terminal fragment of the amino acid sequence of SEQ. ID. No. 3 can span amino acids 105 and 403 of SEQ. ID. No. 3. The N-terminal fragment of the amino acid sequence of SEQ. ID. No. 3 can span the following amino acids of SEQ. ID. No. 3: 1 and 98, 1 and 104, 1 and 122, 1 and 168, 1 and 218, 1 and 266, 1 and 342,1 and 321, and 1 and 372. The internal fragment of the amino acid sequence of SEQ. ID. No. 3 can span the following amino acids of SEQ. ID. No. 3: 76 and 209, 105 and 209, 99 and 209, 137 and 204, 137 and 200, 109 and 204, 109 and 200, 137 and 180, and 105 and 180.

Suitable DNA molecules are those that hybridize to the DNA molecule comprising a nucleotide sequence of SEQ. ID. Nos. 2, 4, 5, 7, 9, 12, 13, and 16 under stringent conditions. An example of suitable high stringency conditions is when hybridization is carried out at 65° C. for 20 hours in a medium containing 1M NaCl, 50 mM Tris-HCl, pH 7.4, 10 mM EDTA, 0.1% sodium dodecyl sulfate, 0.2% ficoll, 0.2% polyvinylpyrrolidone, 0.2% bovine serum albumin, 50 μm g/ml *E. coli* DNA.

Variants may be made by, for example, the deletion or addition of amino acids that have minimal influence on the properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

The hypersensitive response elicitor of the present invention is preferably in isolated form (i.e. separated from its host organism) and more preferably produced in purified form (preferably at least about 60%, more preferably 80%, pure) by conventional techniques. Typically, the hypersensitive response elicitor of the present invention is produced but not secreted into the growth medium of recombinant host cells. Alternatively, the protein or polypeptide of the present invention is secreted into growth medium. In the case of unsecreted protein, to isolate the protein, the host cell (e.g., *E. coli*) carrying a recombinant plasmid is propagated, lysed by sonication, heat, or chemical treatment, and the homogenate is centrifuged to remove bacterial debris. The supernatant is then subjected to heat treatment and the hypersensitive response elicitor is separated by centrifugation. The supernatant fraction containing the hypersensitive response elicitor is subjected to gel filtration in an appropriately sized dextran or polyacrylamide column to separate the fragment. If necessary, the protein fraction may be further purified by ion exchange or HPLC.

The DNA molecule encoding the hypersensitive response elicitor polypeptide or protein can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eucaryotic promotors differ from those of procaryotic promotors. Furthermore, eucaryotic promoters and accompanying genetic signals may not be recognized in or may not function in a procaryotic system, and, further, procaryotic promoters are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference.

Promotors vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promotors may be used. For instance, when cloning in *E. Coli*, its bacteriophages, or plasmids, promoters such as the T7 phage promotor, lac promotor, trp promotor, recA promotor, ribosomal RNA promotor, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promotors produced by recombinant DNA or other synthetic DNA techniques may be used to provide for transcription of the inserted gene.

Bacterial host cell strains and expression vectors may be chosen which inhibit the action of the promotor unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires an SD sequence about 7–9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule encoding the hypersensitive response elicitor polypeptide or protein has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

The present invention's method of imparting stress resistance to plants can involve applying the hypersensitive response elicitor polypeptide or protein in a non-infectious form to all or part of a plant or a plant seed under conditions effective for the elicitor to impart stress resistance. Alternatively, the hypersensitive response elicitor protein or polypeptide can be applied to plants such that seeds recovered from such plants themselves are able to impart stress resistance in plants.

As an alternative to applying a hypersensitive response elicitor polypeptide or protein to plants or plant seeds in order to impart stress resistance in plants or plants grown from the seeds, transgenic plants or plant seeds can be utilized. When utilizing transgenic plants, this involves providing a transgenic plant transformed with a DNA molecule encoding a hypersensitive response elicitor polypeptide or protein and growing the plant under conditions effective to permit that DNA molecule to impart stress resistance to plants. Alternatively, a transgenic plant seed transformed with a DNA molecule encoding a hypersensitive response elicitor polypeptide or protein can be provided and planted in soil. A plant is then propagated from the planted seed under conditions effective to permit that DNA molecule to impart stress resistance to plants.

The embodiment of the present invention where the hypersensitive response elicitor polypeptide or protein is applied to the plant or plant seed can be carried out in a number of ways, including: 1) application of an isolated hypersensitive response elicitor or 2) application of bacteria which do not cause disease and are transformed with a genes encoding the elicitor. In the latter embodiment, the elicitor can be applied to plants or plant seeds by applying bacteria containing the DNA molecule encoding a hypersensitive response elicitor polypeptide or protein. Such bacteria must be capable of secreting or exporting the elicitor so that the elicitor can contact plant or plant seed cells. In these embodiments, the elicitor is produced by the bacteria in planta or on seeds or just prior to introduction of the bacteria to the plants or plant seeds.

The methods of the present invention can be utilized to treat a wide variety of plants or their seeds to impart stress resistance. Suitable plants include dicots and monocots. More particularly, useful crop plants can include: alfalfa, rice, wheat, barley, rye, cotton, sunflower, peanut, corn, potato, sweet potato, bean, pea, chicory, lettuce, endive, cabbage, brussel sprout, beet, parsnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane. Examples of suitable ornamental plants are: *Arabidopsis thaliana*, Saintpaulia, petunia, pelargonium, poinsettia, chrysanthemum, carnation, and zinnia.

In accordance with the present invention, the term "stress" refers to drought, salt, cold temperatures (e.g., frost), chemical treatment (e.g., insecticides, fungicides, herbicides, fertilizers), water, excessive light, and insufficient light.

The method of the present invention involving application of the hypersensitive response elicitor polypeptide or protein can be carried out through a variety of procedures when all or part of the plant is treated, including leaves, stems, roots, propagules (e.g., cuttings), etc. This may (but need not) involve infiltration of the hypersensitive response elicitor polypeptide or protein into the plant. Suitable application methods include high or low pressure spraying, injection, and leaf abrasion proximate to when elicitor application takes place. When treating plant seeds or propagules (e.g., cuttings), in accordance with the application embodiment of the present invention, the hypersensitive response elicitor protein or polypeptide, in accordance with present invention, can be applied by low or high pressure spraying, coating, immersion, or injection. Other suitable application procedures can be envisioned by those skilled in the art provided they are able to effect contact of the elicitor with cells of the plant or plant seed. Once treated with the hypersensitive response elicitor of the present invention, the seeds can be planted in natural or artificial soil and cultivated using conventional procedures to produce plants. After plants have been propagated from seeds treated in accordance with the present invention, the plants may be treated with one or more applications of the hypersensitive response elicitor protein or polypeptide to impart stress resistance to plants.

The hypersensitive response elicitor polypeptide or protein, in accordance with the present invention, can be applied to plants or plant seeds alone or in a mixture with other materials. Alternatively, the hypersensitive response elicitor polypeptide or protein can be applied separately to plants with other materials being applied at different times.

A composition suitable for treating plants or plant seeds in accordance with the application embodiment of the present invention contains a hypersensitive response elicitor polypeptide or protein in a carrier. Suitable carriers include water, aqueous solutions, slurries, or dry powders. In this embodiment, the composition contains greater than 500 nM of the elicitor.

Although not required, this composition may contain additional additives including fertilizer, insecticide, fungicide, nematacide, and mixtures thereof. Suitable fertilizers include $(NH_4)_2NO_3$. An example of a suitable insecticide is Malathion. Useful fungicides include Captan.

Other suitable additives include buffering agents, wetting agents, coating agents, and abrading agents. These materials can be used to facilitate the process of the present invention. In addition, the hypersensitive response elicitor can be applied to plant seeds with other conventional seed formulation and treatment materials, including clays and polysaccharides.

In the alternative embodiment of the present invention involving the use of transgenic plants and transgenic seeds, a hypersensitive response elicitor need not be applied topically to the plants or seeds. Instead, transgenic plants transformed with a DNA molecule encoding such an elicitor are produced according to procedures well known in the art The vector described above can be microinjected directly into plant cells by use of micropipettes to transfer mechanically the recombinant DNA. Crossway, *Mol. Gen. Genetics*, 202:179–85 (1985), which is hereby incorporated by reference. The genetic material may also be transferred into the plant cell using polyethylene glycol. Krens, et al., *Nature*, 296:72–74 (1982), which is hereby incorporated by reference.

Another approach to transforming plant cells with a gene is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells.

Yet another method of introduction is fusion of protoplasts with other entities, either minicells, cells, lysosomes, or other fusible lipid-surfaced bodies. Fraley, et al., *Proc. Natl. Acad. Sci. USA*, 79:1859–63 (1982), which is hereby incorporated by reference.

The DNA molecule may also be introduced into the plant cells by electroporation. Fromm et al., *Proc. Natl. Acad. Sci. USA*, 82:5824 (1985), which is hereby incorporated by reference. In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

Another method of introducing the DNA molecule into plant cells is to infect a plant cell with *Agrobacterium tumefaciens* or *A. rhizogenes* previously transformed with the gene. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25–28° C.

Agrobacterium is a representative genus of the Gram-negative family Rhizobiaceae. Its species are responsible for crown gall (*A. tumefaciens*) and hairy root disease (*A. rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the Ri plasmid of *A. rhizogenes*. The Ti or Ri plasmid is transmitted to plant cells on infection by Agrobacterium and is stably integrated into the plant genome. J. Schell, *Science*, 237:1176–83 (1987), which is hereby incorporated by reference.

After transformation, the transformed plant cells must be regenerated.

Plant rege neration from cultured protoplasts is described in Evans et al., *Handbook of Plant Cell Cultures. Vol. 1:* (MacMillan Publishing Co., New York, 1983); and Vasil I. R. (ed.), *Cell Culture and Somatic Cell Genetics of Plants*, Acad. Press, Orlando, Vol. I, 1984, and Vol. III (1986), which are hereby incorporated by reference.

It is known that practically all plants can be regenerated from cultured cells or tissues, including but not limited to, all major species of sugarcane, sugar beets, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the expression cassette is stably incorporated in transgenic plants, it can be transferred to other plants by sexual crossing. Any of a number of standard breeding techniques can be used, depending upon the species to be crossed.

Once transgenic plants of this type are produced, the plants themselves can be cultivated in accordance with conventional procedure with the presence of the gene encoding the hypersensitive response elicitor resulting in stress resistance to the plant. Alternatively, transgenic seeds or propagules (e.g., cuttings) are recovered from the transgenic plants. The seeds can then be planted in the soil and cultivated using conventional procedures to produce transgenic plants. The transgenic plants are propagated from the planted transgenic seeds under conditions effective to impart stress resistance to plants. While not wishing to be bound by theory, such stress resistance may be RNA mediated or may result from expression of the elicitor polypeptide or protein.

When transgenic plants and plant seeds are used in accordance with the present invention, they additionally can be treated with the same materials as are used to treat the plants and seeds to which a hypersensitive response elicitor in accordance with the present invention is applied. These other materials, including a hypersensitive response elicitor in accordance with the present invention, can be applied to the transgenic plants and plant seeds by the above-noted procedures, including high or low pressure spraying, injection, coating, and immersion. Similarly, after plants have been propagated from the transgenic plant seeds, the plants may be treated with one or more applications of the hypersensitive response elicitor in accordance with the present invention to impart stress resistance. Such plants may also be treated with conventional plant treatment agents (e.g., insecticides, fertilizers, etc.).

EXAMPLES

Example 1

Hypersensitive Response Elicitor-treated Cotton is More Resistant to the Damage Caused by Insecticide Stress Aphids (*Aphids gossypii*) infect cotton during the entire growth season. The damage of aphid infection ranges from honeydew deposit that contaminates the lint and reduces crop value to defoliation that reduces or destroys crops. To protect plants from aphid infection, cotton is usually sprayed with insecticides, for example Asana XL when the infection pressure is not very high, and Admire when the infestation pressure is high. The effect of a hypersensitive response elicitor on aphids in cotton was studied by a trial involving a randomized complete block design. This involved treatment with *Erwinia amylovora* hypersensitive response elicitor (i.e. HP-100™) at 20, 60, and 80 ppm and a chemical insecticide, Asana XL, at 8 oz./ac. Each treatment involved foliar application beginning at cotyledon to three true leaves and thereafter at 14 day intervals using a backpack sprayer. Aphid counts and overall growth of the cotton were made immediately prior to spray application at 14, 28, 35, and 42 days after the first treatment ("DAT 1"). Twenty-five randomly selected leaves per plot were collected at the first three sampling dates and the leaves per plot at the final sampling date.

Results

1. Aphid control: The number of aphids in the hypersensitive response elicitor-treated cotton were significantly reduced in comparison to the chemical treated cotton (see Table 1).

TABLE 1

Aphid count per leaf on cotton after treatment with Asana XL ® or HP-1000 ™

| Treatment | Rate[2] | Number of aphids per leaf[1] No. sprays applied/days after treatment | | | |
|---|---|---|---|---|---|
| | | 1/14 DAT 1 | 2/28 DAT 1 | 3/35 DAT 1 | 4/42 DAT 1 |
| Asana XL ® | 8 oz/ac | 0.2 a | 32.2 a | 110.0 a | 546.9 a |
| HP-1000 ™ | 20 μg/ml | 0.2 a | 7.8 b | 22.9 b | 322.1 a |
| HP-1000 ™ | 60 μg/ml | 0.1 a | 4.9 b | 34.6 b | 168.3 a |
| HP-1000 ™ | 80 μg/ml | 0.0 a | 2.7 b | 25.8 b | 510.2 a |

[1]Means followed by different letters are significantly different according to Duncan's MRT, P = 0.05.
[2]Rate for Asana XL ® is for formulated product, rate for HP-1000 ™ is for active ingredient (a.i.).

At 14 days after DAT 1, aphid counts were relatively low across all of the treatments, but by 28 days after DAT 1 (by which time two sprayings had been applied), the number of aphids per leaf were significantly greater in Asana XL-treated plants compared to the hypersensitive response elicitor-treated cottons. By 35 days after DAT 1 (by which time three sprayings had been applied), aphid counts had risen for all treatments, yet aphid counts per leaf were still significantly lower for hypersensitive response elicitor-treated cotton compared to the Asana XL treatment. Finally, at 42 days after DAT 1 (by which time four sprayings had been applied), the number of aphids per leaf had increased to a level that threatened to overwhelm the plants even when treated with the standard chemical insecticide. To save the trial, another chemical, Pravado (Admire), was applied to all plots to eradicate aphids from the field.

2. Hypersensitive response elicitor-treated cotton was more resistant to the damage caused by Pravado (Admire) and Asana. After the second chemical spraying, it was observed that cotton plants were stress shocked by the insecticides. The cotton plants previously treated with Asana and untreated control were defoliated. On most of the chemical-treated cotton, there were no leaves, or very few leaves, in the lower portion of plants. However, the hypersensitive response elicitor-treated plants, especially the plot where hypersensitive response elicitor was applied at 80 ppm, had no defoliation and the cotton plants were vigorous and healthy. By counting the number of mature balls, it clearly showed that hypersensitive response elicitor-treated plants (at 80 ppm) had more ball setting than chemical and untreated control (Table 2), indicating that hypersensitive response elicitor-treated plants were more tolerant to the stress caused by insecticide.

TABLE 2

Number of Formed Cotton Balls Counted on Ten Plants in Each of Four Replicates Per Treatment.

| Treatment | No. balls/10 plants/replicate |
|---|---|
| UTC | 28 |
| Chemical standard | 6 |
| Hypersensitive Response Elicitor | 35 |

Example 2

Hypersensitive Response Elicitor-treated Cucumbers are More Resistant to Drought A cucumber field trial was set up to test the effect of *Erwinia amylovora* hypersensitive response elicitor on disease control, tolerance to drought stress, and yield. Three different rates were tested, there at 15, 30, and 60 μg/ml. In addition to hypersensitive response elicitor treatment, there was an untreated control. Each treatment contained three replicate plots. When the first true leaf emerges, hypersensitive response elicitor was sprayed with a back bag sprayer. The second spray was applied ten days after the first spray. The third application was right after the recovery of cucumber seedlings after the transplanting to the field. Individual treatment was randomly assigned in the field.

When the first true leaf emerged (Day 0), a first application was sprayed. Usually cucumber seedlings are transplanted when seedlings show two true leaves. It has been known that the recovery rate after the transplanting is closely related to the size of the seedlings. Because of the drought, the seedlings were maintained in the nursery for an extra ten days and the second spray was applied on Day 10. Two days after the second spray, the plants were transplanted into fields and covered with plastic sheets. The plants had 4–5 true leaves.

Result

The recovery rate of the transplanted cucumber seedlings was higher for the hypersensitive response elicitor-treated plants than for the untreated control. More than 80% of the hypersensitive response elicitor-treated cucumber seedlings survived, while only 57% untreated plants survived.

Throughout the growth season, there was a serious drought problem. Early field visits indicated that hypersensitive response elicitor-treated plants had more root mass and better over-all growth. Hypersensitive response elicitor-treated cucumber started to flower 14 days earlier than untreated control cucumber. The early flowering resulted in an earlier harvest. In the first harvest, more than 0.4 kilograms of cucumber fruits per plant were harvested from the hypersensitive response elicitor-treated cucumbers; however, virtually no fruit was harvested from untreated control. By the end of the season, untreated plants died due to severe drought, but hypersensitive response elicitor-treated plants were still alive and had one more harvest.

The final yield was significantly different between hypersensitive response elicitor-treated and untreated plants. Hypersensitive response elicitor administered at the rate of 30 ppm produced three times greater yield than the control plants (Table 3).

TABLE 3

Yield Increase of Cucumber Fruit from Hypersensitive Response Elicitor Treated Plants

| Treatment | Replicate | kg/plant | Yield/ Replicate | | % of the Yield Increase |
|---|---|---|---|---|---|
| HP 15 | I | 1.25 | 37.5 | | |
| | II | 1.00 | 30.0 | 103.8 | 241 |
| | III | 1.21 | 36.3 | | |
| HP 30 | I | 1.54 | 46.2 | | |
| | II | 1.43 | 42.9 | 133.2 | 339 |
| | III | 1.47 | 44.1 | | |
| Control | I | 0.43 | 12.9 | | |
| | II | 0.41 | 12.3 | 39.3 | |
| | III | 0.47 | 14.1 | | |

The increased yield was partially attributed to hypersensitive response elicitor-induced growth enhancement and partially resulted from more tolerance of hypersensitive response elicitor-treated cucumber to drought, because usually the yield increase from hypersensitive response elicitor-induced growth enhancement is between 10–40%.

Example 3

Hypersensitive Response Elicitor-treated Pepper is More Tolerant to Herbicide Stress Pepper seedlings were drenched with hypersensitive response elicitor at 20 ppm seven days before transplanting, sprayed seven days after the transplanting, and then, sprayed every fourteen days. Standard chemicals, Brave, Maneb, Kocide, and Admire, were used for the rest of the treatment. In addition to early growth enhancement, which resulted in a higher yield, larger fruit, and resistance to several diseases, hypersensitive response elicitor-treated pepper was more tolerant to herbicide damage. The pepper field was applied with the herbicide SENCOR which is not labeled for pepper. This herbicide is known to cause severe foliar damage to pepper in chemically-treated plants but not with hypersensitive response elicitor-treated plants.

The difference between the adverse effect of the herbicide on the hypersensitive response elicitor and non-hypersensitive response elicitor treated plants is dramatic. See Table 4 below. Thirty-nine of the 60 elicitor-treated plants showed only minor damage by the herbicide, the damaged leaves were less than 20%. In contrast, 53 out of the 60 chemically-treated pepper plants had severe damage, 40–57% of the leaves were damaged, and 20 plants were dead. The ability of hypersensitive response elicitors to help crops withstand the phytotoxic effects of a herbicide is very important benefit to in agricultural industry.

TABLE 4

Hypersensitive Response Elicitor-Treated Peppers are More Tolerant to Herbicide Damage.

| | Damage Rating | | | | | | |
|---|---|---|---|---|---|---|---|
| Treatment | 1 | 2 | 3 | 4 | 5 | 6 | Damage Index % |
| Hypersensitive Response Elicitor | 1 | 38 | 17 | 3 | 1 | 0 | 41 |
| Chemicals | 0 | 1 | 6 | 16 | 19 | 18 | 87 |

Damage Rating: 1. No damage; 2. 0–20% leaves damaged; 3. 20–40% leaves damaged; 4. 40–50% leaves damaged; 6. More than 75% leaves damaged or entire plant dead.
Damage index = sum of each rating times the number of plants under the rating scale, divided by total number of plants times 6.
Damage index for hypersensitive response elicitor-treated plants = $1 \times 1 + 2 \times 38 + 3 \times 17 + 4 \times 3 + 5 \times 1 + 6 \times 0 \times 100\% = 41\%$ Example 4

Hypersensitive Response Elicitor-treated Pepper is More Tolerant to Herbicide Stress under Controlled Experimental Conditions A field trial was conducted to test if hypersensitive elicitor treated pepper would be more tolerant to herbicide stress. The trial contains 6 treatments and 4 replicates for each treatment. The treatments are described as follows:

1. Control, the peppers were neither treated by a hypersensitive response ("HR") elicitor nor by LEXONE™ herbicide (DuPont Agricultural Products, Wilmington, Del.).

2. Control pepper with application of 0.15 pound LEXONE™ herbicide/acre.

3. Control pepper with application of 0.3 pound LEXONE™ herbicide/acre.

4. HR elicitor treatment with no application of LEXONE™ herbicide using a formulated product known as MESSENGER™ biopesticide (Eden Bioscience Corporation, Bothell, Wash.) containing 3% HR elicitor protein was used.

5. HR elicitor treatment with application of 0.15 pound LEXONE™ herbicide/acre.

6. HR elicitor treatment with application of 0.3 pound LEXONE™ herbicide/acre.

LEXONE™ contains the same active ingredient as SENCOR™ herbicide (Bayer, Kansas City, Mo.) used in Example 3. Pepper seedlings were drenched with MESSENGER™ solution at the concentration of HR elicitor protein of about 20 ppm seven days before transplanting into the field and then sprayed every 14 days after the transplanting. LEXONE was applied at high (0.3 pound/acre) and low levels (0.15 pound/acre). 50 gallon water and 100 mL of the herbicide solution was introduced into the root zone of each plant in the respective treatment five weeks after transplant into the field.

The treatments were evaluated for the percent of chlorosis caused by the LEXONE™ herbicide application and for the pepper yield. HR elicitor-treated plants exposed to the high rate of herbicide had significantly less chlorosis and produced 108 % more fruit in comparison to the non-hypersensitive response elicitor treated plants exposed to the same amount of herbicide. See Tables 5 and 6 below. There was no significant difference in the reduction of chlorosis at the low rate of herbicide between the HR elicitor treated and non-HR elicitor treated peppers. However, the HR elicitor treated plants produced 15% more fruit than the corresponding control plants exposed to the same amount of herbicide. There was no chlorosis in either the check or HR elicitor-treated plants that did not receive LEXONE™ herbicide treatment.

The HR elicitor treated plants were much less severely affected by the herbicide application than the respective control plants at the high rate of herbicide. However, the amount of visual chlorosis was similar at the low rate for both the check and HR elicitor-treated plants. More importantly, the yields from both the high and low rate herbicide treatments of HR elicitor treated plants were less severely effected by the herbicide than the checks. These findings firther confirrn that HR elicitors can help crops withstand the phytotoxic effects of herbicides and are very beneficial to the agricultural industry.

Example 5

Hypersensitive Response Elicitor-treated Cotton is More Tolerant to Drought Stress A non-irrigated cotton trial experienced 26 consecutive days of drought. The average daily heat index was near or over 100 degrees F., adding to the stress placed on the plants in the field.

Observations in the field indicated that plants treated with HR elicitor at the concentration of 15 ppm (2.2 oz formulated product, MESSENGER™ containing 3 % active ingredient HR elicitor protein) were more vigorous and had less defoliation than the check plants as a result of the heat and drought stress. Equal numbers of plants from the MESSENGER™-treated and the non-MESSENGER™ treated plots were carefully removed from the field and mapped for the number of nodes and bolls by position. The plants were also weighed on a Metler analytical scale to determine whole plant, root and shoot weights.

MESSENGER™ treated plants survived the heat and drought stresses much better than the untreated plants did. Plants treated with MESSENGER™ had 37.6% more root and shoot mass than the check plants (Table 7). The MES-

TABLE 5

Reduction of Foliar Chlorosis and Increase in Yield in Hypersensitive Response Elicitor Treated Plants after Exposure to LEXONE ™ Herbicide

| Treatment | Percent foliar chlorosis and yield of pepper | | | | | | |
|---|---|---|---|---|---|---|---|
| | A | B | C | D | E | Yield (pound) | % difference from the respective control |
| 6 (MESSENGER ™ + High rate LEXONE ™ ) | 13.75 | 30.00 | 37.50 | 36.25 | 40.00 | 8.31 | 108% |
| 3 (High rate LEXONE ™ ) | 26.25 | 43.75 | 51.25 | 50.00 | 51.25 | 4.00 | — |
| 5 (MESSENGER ™ + low rate LENOXE ™ ) | 16.25 | 22.50 | 28.75 | 23.75 | 27.50 | 8.00 | 15% |
| 2 (LENOXE ™ ) | 12.50 | 20.00 | 25.00 | 25.00 | 23.75 | 6.81 | — |

TABLE 6

Weight of Harvested Peppers Increased in Hypersensitive Response Elicitor Treated Plants after Exposure to LEXONE ™ Herbicide Compared to Check Plants.

| Treatment | Weight of peppers harvested Dec. 1, 1998 in pounds |
|---|---|
| HP20 + high rate LEXONE ™ | 8.31 |
| Check + high rate LEXONE ™ | 4.00 |
| HP20 + low rate LEXONE ™ | 8.00 |
| Check + low rate LEXONE ™ | 6.81 |

SENGER™ treated plants also had significantly more cotton bolls than the check plants (Table 8). The number of cotton bolls from positions 1 and 2 have a significant contribution to the overall yield. Table 8 showed that MESSENGER™ treated plants had 47% more bolls in positions 1 and 2 and 57% more boll from a whole plant in comparison to the yield achieved using a grower standard treatment (i.e. with no MESSENGER™ treatment). A common reaction to stress in cotton is for the plant to abort bolls. The results indicate that MESSENGER™-treated plants are more tolerant to the drought stress.

TABLE 7

Weight per Plant of Non-Irrigated Cotton Following 26 Days of Drought.

| Treatment | Root weight (pond/plant) | % Difference | Shoot weight (pond/plant) | % difference | Whole plant weight (pond/plant) | % difference |
|---|---|---|---|---|---|---|
| MESSENGER ™ 2.2 oz/acre | 0.041 a* | 37.6% | 0.505 a | 37.5% | 0.546 | 37.5% |
| Control (Grower standard) | 0.0298 b | | 0.367 b | | 0.397 | |
| Level of statistically significant | P = 0.119 | | P = 0.034 | | P = 0.033 | |

*Same letter indicates no statistical difference between the two treatments at the defined level; different letter indicates a statistical difference between the two treatments at the defined level.

TABLE 8

Number of Bolls per 5 Plants at the Number 1 & 2 positions, and Total Number of Bolls from Whole Plants in Non-irrigated Cotton Following 26 days of drought.

| Treatment | Avg. # bolls in the #1 & 2 position | Percent difference | Avg. # of total bolls per 5 plant | Percent difference |
|---|---|---|---|---|
| MESSENGER ™ 2.2 OZ. | 18.4 a | +46.0% | 21.4 a | +57.0% |
| Check | 12.6 b | | 13.6 b | — |
| Statistically significant level | P = 0.032 | | P = 0.01 | |

*Same letter indicates no statistical difference between the two treatments at the defined level; different letter indicates a statistical difference between the two treatments at the defined level.

Example 6

Hypersensitive Response Elicitor-treated Tomato is More Tolerant to Calcium Deficiency Calcium is an important element for plant physiology and development. A deficiency in calcium can cause several plant diseases. For example, blossom-end rot is caused by a localized calcium deficiency in the distal end of the tomato fruit. Because calcium is not a highly mobile element, a deficiency can occur with a fluctuation in water supply. In the past, tomato growers experienced higher level of blossom-end rot during dry weather conditions when infrequent rains storms dumped a lot of water and then return to a hot and dry condition quickly. Lowering or raising the irrigation water table erratically during a dry and hot growing season can also increase the disease.

A field trial was designed to test if HR elicitor protein-treated tomato can be more tolerant to the calcium deficiency under a dry hot growing season. MESSENGER™, the formulated product containing 3% HR elicitor, was used for the trial. The application rate of the MESSENGER™ was 2.27 oz per care. The first spray of MESSENGER™ was carried out 7 days before the transplanting and then every 14-days after transplanting. MESSENGER™-treated tomatoes were compared with a standard grower treatment not utilizing MESSENGER™. Each treatment had 4 replicates.

The number of infected fruit was counted from a 100 square foot field. The rot typically begins with light tan water soaked lesions, which then enlarge, and then turn black. In a survey, about 20% of the fruits were infected. Severe end-rot symptoms occurred in the standard treatment; however, an average of only 2.5 % of the fruit was infected in the MESSENGER™-treated plants. The harvest data showed that MESSENGER™-treated plants had 8% more marketable fruit (Table 9). The test results demonstrated that MESSENGER™-treatment can reduce the stress resulting from calcium deficiency and increase plant resistance to blossom-end rot.

TABLE 9

Hypersensitive Response Elicitor Treatment Reduced Blossom-End Rot Infection, Increased Yield of Tomato Fruit

| | Blossom-End Infected Fruit* | | | | Tomato Fruit Yield | |
|---|---|---|---|---|---|---|
| Treatment | Rep I | Rep II | Rep III | Rep IV | Bin/Acre | % Difference |
| MESSENGER ™ | 0 | 9 | 0 | 1 | 35 | 8 |
| Standard Treatment) | 24 | 22 | 16 | 17 | 31.5 | — |

*The data were collected from the fruits in 100 square foot plot

Although the invention has been described in detail for the purpose of illustration, it is understood that such detail is solely for that purpose, and variations can be made therein by those skilled in the art without departing from the spirit and scope of the invention which is defined by the following claims.

SEQUENCE LISTING

<160> NUMBER OF SEQ ID NOS: 18

<210> SEQ ID NO 1
<211> LENGTH: 338
<212> TYPE: PRT
<213> ORGANISM: Erwinia chrysanthemi

<400> SEQUENCE: 1

```
Met Gln Ile Thr Ile Lys Ala His Ile Gly Gly Asp Leu Gly Val Ser
  1               5                  10                  15

Gly Leu Gly Ala Gln Gly Leu Lys Gly Leu Asn Ser Ala Ala Ser Ser
             20                  25                  30

Leu Gly Ser Ser Val Asp Lys Leu Ser Ser Thr Ile Asp Lys Leu Thr
         35                  40                  45

Ser Ala Leu Thr Ser Met Met Phe Gly Ala Leu Ala Gln Gly Leu
 50                  55                  60

Gly Ala Ser Ser Lys Gly Leu Gly Met Ser Asn Gln Leu Gly Gln Ser
 65                  70                  75                  80

Phe Gly Asn Gly Ala Gln Gly Ala Ser Asn Leu Leu Ser Val Pro Lys
                 85                  90                  95

Ser Gly Gly Asp Ala Leu Ser Lys Met Phe Asp Lys Ala Leu Asp Asp
            100                 105                 110

Leu Leu Gly His Asp Thr Val Thr Lys Leu Thr Asn Gln Ser Asn Gln
            115                 120                 125

Leu Ala Asn Ser Met Leu Asn Ala Ser Gln Met Thr Gln Gly Asn Met
130                 135                 140

Asn Ala Phe Gly Ser Gly Val Asn Asn Ala Leu Ser Ser Ile Leu Gly
145                 150                 155                 160

Asn Gly Leu Gly Gln Ser Met Ser Gly Phe Ser Gln Pro Ser Leu Gly
                165                 170                 175

Ala Gly Gly Leu Gln Gly Leu Ser Gly Ala Gly Ala Phe Asn Gln Leu
            180                 185                 190

Gly Asn Ala Ile Gly Met Gly Val Gly Gln Asn Ala Ala Leu Ser Ala
            195                 200                 205

Leu Ser Asn Val Ser Thr His Val Asp Gly Asn Asn Arg His Phe Val
210                 215                 220

Asp Lys Glu Asp Arg Gly Met Ala Lys Glu Ile Gly Gln Phe Met Asp
225                 230                 235                 240

Gln Tyr Pro Glu Ile Phe Gly Lys Pro Glu Tyr Gln Lys Asp Gly Trp
                245                 250                 255

Ser Ser Pro Lys Thr Asp Asp Lys Ser Trp Ala Lys Ala Leu Ser Lys
            260                 265                 270

Pro Asp Asp Gly Met Thr Gly Ala Ser Met Asp Lys Phe Arg Gln
            275                 280                 285

Ala Met Gly Met Ile Lys Ser Ala Val Ala Gly Asp Thr Gly Asn Thr
290                 295                 300

Asn Leu Asn Leu Arg Gly Ala Gly Ala Ser Leu Gly Ile Asp Ala
305                 310                 315                 320

Ala Val Val Gly Asp Lys Ile Ala Asn Met Ser Leu Gly Lys Leu Ala
                325                 330                 335

Asn Ala
```

<210> SEQ ID NO 2

<211> LENGTH: 2141
<212> TYPE: DNA
<213> ORGANISM: Erwinia chrysanthemi

<400> SEQUENCE: 2

| | | | | | |
|---|---|---|---|---|---|
| cgattttacc | cgggtgaacg | tgctatgacc | gacagcatca | cggtattcga | caccgttacg | 60 |
| gcgtttatgg | ccgcgatgaa | ccggcatcag | gcggcgcgct | ggtcgccgca | atccggcgtc | 120 |
| gatctggtat | ttcagtttgg | ggacaccggg | cgtgaactca | tgatgcagat | tcagccgggg | 180 |
| cagcaatatc | ccggcatgtt | gcgcacgctg | ctcgctcgtc | gttatcagca | ggcggcagag | 240 |
| tgcgatggct | gccatctgtg | cctgaacggc | agcgatgtat | tgatcctctg | gtggccgctg | 300 |
| ccgtcggatc | ccggcagtta | ccgcaggtg | atcgaacgtt | tgtttgaact | ggcgggaatg | 360 |
| acgttgccgt | cgctatccat | agcaccgacg | gcgcgtccgc | agacagggaa | cggacgcgcc | 420 |
| cgatcattaa | gataaaggcg | ctttttttta | ttgcaaaacg | gtaacggtga | ggaaccgttt | 480 |
| caccgtcggc | gtcactcagt | aacaagtatc | catcatgatg | cctacatcgg | gatcggcgtg | 540 |
| ggcatccgtt | gcagatactt | ttgcgaacac | ctgacatgaa | tgaggaaacg | aaattatgca | 600 |
| aattacgatc | aaagcgcaca | tcggcggtga | tttgggcgtc | tccggtctgg | ggctgggtgc | 660 |
| tcagggactg | aaaggactga | attccgcggc | ttcatcgctg | ggttccagcg | tggataaact | 720 |
| gagcagcacc | atcgataagt | tgacctccgc | gctgacttcg | atgatgtttg | gcggcgcgct | 780 |
| ggcgcagggg | ctgggcgcca | gctcgaaggg | gctggggatg | agcaatcaac | tgggccagtc | 840 |
| tttcggcaat | ggcgcgcagg | gtgcgagcaa | cctgctatcc | gtaccgaaat | ccggcggcga | 900 |
| tgcgttgtca | aaaatgtttg | ataaagcgct | ggacgatctg | ctgggtcatg | acaccgtgac | 960 |
| caagctgact | aaccagagca | accaactggc | taattcaatg | ctgaacgcca | gccagatgac | 1020 |
| ccagggtaat | atgaatgcgt | tcggcagcgg | tgtgaacaac | gcactgtcgt | ccattctcgg | 1080 |
| caacggtctc | ggccagtcga | tgagtggctt | ctctcagcct | tctctggggg | caggcggctt | 1140 |
| gcagggcctg | agcggcgcgg | gtgcattcaa | ccagttgggt | aatgccatcg | gcatgggcgt | 1200 |
| ggggcagaat | gctgcgctga | gtgcgttgag | taacgtcagc | acccacgtag | acggtaacaa | 1260 |
| ccgccacttt | gtagataaag | aagatcgcgg | catggcgaaa | gagatcggcc | agtttatgga | 1320 |
| tcagtatccg | gaaatattcg | gtaaaccgga | ataccagaaa | gatggctgga | gttcgccgaa | 1380 |
| gacggacgac | aaatcctggg | ctaaagcgct | gagtaaaccg | gatgatgacg | gtatgaccgg | 1440 |
| cgccagcatg | gacaaattcc | gtcaggcgat | gggtatgatc | aaaagcgcgg | tggcgggtga | 1500 |
| taccggcaat | accaacctga | acctgcgtgg | cgcgggcggt | gcatcgctgg | gtatcgatgc | 1560 |
| ggctgtcgtc | ggcgataaaa | tagccaacat | gtcgctgggc | aagctggcca | acgcctgata | 1620 |
| atctgtgctg | gcctgataaa | gcggaaacga | aaaagagac | ggggaagcct | gtctcttttc | 1680 |
| ttattatgcg | gttatgcgg | ttacctggac | cggttaatca | tcgtcatcga | tctggtacaa | 1740 |
| acgcacattt | tcccgttcat | tcgcgtcgtt | acgcgccaca | atcgcgatgg | catcttcctc | 1800 |
| gtcgctcaga | ttgcgcggct | gatgggggaac | gccgggtgga | atatagagaa | actcgccggc | 1860 |
| cagatggaga | cacgtctgcg | ataaatctgt | gccgtaacgt | gtttctatcc | gcccctttag | 1920 |
| cagatagatt | gcggtttcgt | aatcaacatg | gtaatgcggt | tccgcctgtg | cgccggccgg | 1980 |
| gatcaccaca | atattcatag | aaagctgtct | tgcacctacc | gtatcgcggg | agataccgac | 2040 |
| aaaatagggc | agtttttgcg | tggtatccgt | ggggtgttcc | ggcctgacaa | tcttgagttg | 2100 |
| gttcgtcatc | atctttctcc | atctgggcga | cctgatcggt | t | | 2141 |

-continued

```
<210> SEQ ID NO 3
<211> LENGTH: 403
<212> TYPE: PRT
<213> ORGANISM: Erwinia amylovora

<400> SEQUENCE: 3

Met Ser Leu Asn Thr Ser Gly Leu Gly Ala Ser Thr Met Gln Ile Ser
  1               5                  10                  15

Ile Gly Gly Ala Gly Gly Asn Asn Gly Leu Leu Gly Thr Ser Arg Gln
             20                  25                  30

Asn Ala Gly Leu Gly Gly Asn Ser Ala Leu Gly Leu Gly Gly Gly Asn
         35                  40                  45

Gln Asn Asp Thr Val Asn Gln Leu Ala Gly Leu Leu Thr Gly Met Met
     50                  55                  60

Met Met Met Ser Met Met Gly Gly Gly Gly Leu Met Gly Gly Gly Leu
 65                  70                  75                  80

Gly Gly Gly Leu Gly Asn Gly Leu Gly Gly Ser Gly Gly Leu Gly Glu
                 85                  90                  95

Gly Leu Ser Asn Ala Leu Asn Asp Met Leu Gly Gly Ser Leu Asn Thr
            100                 105                 110

Leu Gly Ser Lys Gly Gly Asn Asn Thr Thr Ser Thr Thr Asn Ser Pro
        115                 120                 125

Leu Asp Gln Ala Leu Gly Ile Asn Ser Thr Ser Gln Asn Asp Asp Ser
    130                 135                 140

Thr Ser Gly Thr Asp Ser Thr Ser Asp Ser Ser Asp Pro Met Gln Gln
145                 150                 155                 160

Leu Leu Lys Met Phe Ser Glu Ile Met Gln Ser Leu Phe Gly Asp Gly
                165                 170                 175

Gln Asp Gly Thr Gln Gly Ser Ser Ser Gly Gly Lys Gln Pro Thr Glu
            180                 185                 190

Gly Glu Gln Asn Ala Tyr Lys Lys Gly Val Thr Asp Ala Leu Ser Gly
        195                 200                 205

Leu Met Gly Asn Gly Leu Ser Gln Leu Leu Gly Asn Gly Gly Leu Gly
    210                 215                 220

Gly Gly Gln Gly Gly Asn Ala Gly Thr Gly Leu Asp Gly Ser Ser Leu
225                 230                 235                 240

Gly Gly Lys Gly Leu Gln Asn Leu Ser Gly Pro Val Asp Tyr Gln Gln
                245                 250                 255

Leu Gly Asn Ala Val Gly Thr Gly Ile Gly Met Lys Ala Gly Ile Gln
            260                 265                 270

Ala Leu Asn Asp Ile Gly Thr His Arg His Ser Ser Thr Arg Ser Phe
        275                 280                 285

Val Asn Lys Gly Asp Arg Ala Met Ala Lys Glu Ile Gly Gln Phe Met
    290                 295                 300

Asp Gln Tyr Pro Glu Val Phe Gly Lys Pro Gln Tyr Gln Lys Gly Pro
305                 310                 315                 320

Gly Gln Glu Val Lys Thr Asp Asp Lys Ser Trp Ala Lys Ala Leu Ser
                325                 330                 335

Lys Pro Asp Asp Asp Gly Met Thr Pro Ala Ser Met Glu Gln Phe Asn
            340                 345                 350

Lys Ala Lys Gly Met Ile Lys Arg Pro Met Ala Gly Asp Thr Gly Asn
        355                 360                 365

Gly Asn Leu Gln Ala Arg Gly Ala Gly Gly Ser Ser Leu Gly Ile Asp
    370                 375                 380
```

-continued

Ala Met Met Ala Gly Asp Ala Ile Asn Asn Met Ala Leu Gly Lys Leu
385 390 395 400

Gly Ala Ala

<210> SEQ ID NO 4
<211> LENGTH: 1288
<212> TYPE: DNA
<213> ORGANISM: Erwinia amylovora

<400> SEQUENCE: 4
aagcttcggc atggcacgtt tgaccgttgg gtcggcaggg tacgtttgaa ttattcataa 60
gaggaatacg ttatgagtct gaatacaagt gggctgggag cgtcaacgat gcaaatttct 120
atcggcggtg cgggcggaaa taacgggttg ctgggtacca gtcgccagaa tgctgggttg 180
ggtggcaatt ctgcactggg gctgggcggc ggtaatcaaa atgataccgt caatcagctg 240
gctggcttac tcaccggcat gatgatgatg atgagcatga tgggcggtgg tgggctgatg 300
ggcggtggct taggcggtgg cttaggtaat ggcttgggtg gctcaggtgg cctgggcgaa 360
ggactgtcga acgcgctgaa cgatatgtta ggcggttcgc tgaacacgct gggctcgaaa 420
ggcggcaaca ataccacttc aacaacaaat tccccgctgg accaggcgct gggtattaac 480
tcaacgtccc aaaacgacga ttccacctcc ggcacagatt ccacctcaga ctccagcgac 540
ccgatgcagc agctgctgaa gatgttcagc gagataatgc aaagcctgtt tggtgatggg 600
caagatggca cccagggcag ttcctctggg ggcaagcagc cgaccgaagg cgagcagaac 660
gcctataaaa aaggagtcac tgatgcgctg tcgggcctga tgggtaatgg tctgagccag 720
ctccttggca acgggggact gggaggtggt cagggcggta atgctggcac gggtcttgac 780
ggttcgtcgc tgggcggcaa agggctgcaa aacctgagcg ggccggtgga ctaccagcag 840
ttaggtaacg ccgtgggtac cggtatcggt atgaaagcgg gcattcaggc gctgaatgat 900
atcggtacgc acaggcacag ttcaacccgt tctttcgtca ataaaggcga tcgggcgatg 960
gcgaaggaaa tcggtcagtt catggaccag tatcctgagg tgtttggcaa gccgcagtac 1020
cagaaaggcc cgggtcagga ggtgaaaacc gatgacaaat catgggcaaa agcactgagc 1080
aagccagatg acgacggaat gacaccagcc agtatggagc agttcaacaa agccaagggc 1140
atgatcaaaa ggcccatggc gggtgatacc ggcaacggca acctgcaggc acgcggtgcc 1200
ggtggttctt cgctgggtat tgatgccatg atggccggtg atgccattaa caatatggca 1260
cttggcaagc tgggcgcggc ttaagctt 1288

<210> SEQ ID NO 5
<211> LENGTH: 1344
<212> TYPE: DNA
<213> ORGANISM: Erwinia amylovora

<400> SEQUENCE: 5
atgtcaattc ttacgcttaa caacaatacc tcgtcctcgc cgggtctgtt ccagtccggg 60
ggggacaacg ggcttggtgg tcataatgca aattctgcgt tggggcaaca acccatcgat 120
cggcaaacca ttgagcaaat ggctcaatta ttggcggaac tgttaaagtc actgctatcg 180
ccacaatcag gtaatgcggc aaccggagcc ggtggcaatg accagactac aggagttggt 240
aacgctggcg gcctgaacgg acgaaaaggc acagcaggaa ccactccgca gtctgacagt 300
cagaacatgc tgagtgagat gggcaacaac gggctggatc aggccatcac gcccgatggc 360
cagggcggcg ggcagatcgg cgataatcct ttactgaaag ccatgctgaa gcttattgca 420

-continued

```
cgcatgatgg acggccaaag cgatcagttt ggccaacctg gtacgggcaa caacagtgcc    480
tcttccggta cttcttcatc tggcggttcc ccttttaacg atctatcagg ggggaaggcc    540
ccttccggca actccccttc cggcaactac tctcccgtca gtaccttctc acccccatcc    600
acgccaacgt cccctacctc accgcttgat ttcccttctt ctcccaccaa agcagccggg    660
ggcagcacgc cggtaaccga tcatcctgac cctgttggta gcgcgggcat cggggccgga    720
aattcggtgg ccttcaccag cgccggcgct aatcagacgg tgctgcatga caccattacc    780
gtgaaagcgg gtcaggtgtt tgatggcaaa ggacaaacct tcaccgccgg ttcagaatta    840
ggcgatggcg gccagtctga aaaccagaaa ccgctgttta tactggaaga cggtgccagc    900
ctgaaaaacg tcaccatggg cgacgacggg gcggatggta ttcatcttta cggtgatgcc    960
aaaatagaca atctgcacgt caccaacgtg ggtgaggacg cgattaccgt taagccaaac   1020
agcgcgggca aaaaatccca cgttgaaatc actaacagtt ccttcgagca cgcctctgac   1080
aagatcctgc agctgaatgc cgatactaac ctgagcgttg acaacgtgaa ggccaaagac   1140
tttggtactt ttgtacgcac taacggcggt caacagggta actgggatct gaatctgagc   1200
catatcagcg cagaagacgg taagttctcg ttcgttaaaa gcgatagcga ggggctaaac   1260
gtcaatacca gtgatatctc actgggtgat gttgaaaacc actacaaagt gccgatgtcc   1320
gccaacctga aggtggctga atga                                          1344
```

<210> SEQ ID NO 6
<211> LENGTH: 447
<212> TYPE: PRT
<213> ORGANISM: Erwinia amylovora

<400> SEQUENCE: 6

```
Met Ser Ile Leu Thr Leu Asn Asn Asn Thr Ser Ser Ser Pro Gly Leu
  1               5                  10                  15

Phe Gln Ser Gly Gly Asp Asn Gly Leu Gly Gly His Asn Ala Asn Ser
             20                  25                  30

Ala Leu Gly Gln Gln Pro Ile Asp Arg Gln Thr Ile Glu Gln Met Ala
         35                  40                  45

Gln Leu Leu Ala Glu Leu Leu Lys Ser Leu Leu Ser Pro Gln Ser Gly
     50                  55                  60

Asn Ala Ala Thr Gly Ala Gly Gly Asn Asp Gln Thr Thr Gly Val Gly
 65                  70                  75                  80

Asn Ala Gly Gly Leu Asn Gly Arg Lys Gly Thr Ala Gly Thr Thr Pro
                 85                  90                  95

Gln Ser Asp Ser Gln Asn Met Leu Ser Glu Met Gly Asn Asn Gly Leu
            100                 105                 110

Asp Gln Ala Ile Thr Pro Asp Gly Gln Gly Gly Gly Gln Ile Gly Asp
        115                 120                 125

Asn Pro Leu Leu Lys Ala Met Leu Lys Leu Ile Ala Arg Met Met Asp
    130                 135                 140

Gly Gln Ser Asp Gln Phe Gly Gln Pro Gly Thr Gly Asn Asn Ser Ala
145                 150                 155                 160

Ser Ser Gly Thr Ser Ser Ser Gly Gly Ser Pro Phe Asn Asp Leu Ser
                165                 170                 175

Gly Gly Lys Ala Pro Ser Gly Asn Ser Pro Ser Gly Asn Tyr Ser Pro
            180                 185                 190

Val Ser Thr Phe Ser Pro Pro Ser Thr Pro Thr Ser Pro Thr Ser Pro
        195                 200                 205
```

```
Leu Asp Phe Pro Ser Ser Pro Thr Lys Ala Ala Gly Gly Ser Thr Pro
    210                 215                 220

Val Thr Asp His Pro Asp Pro Val Gly Ser Ala Gly Ile Gly Ala Gly
225                 230                 235                 240

Asn Ser Val Ala Phe Thr Ser Ala Gly Ala Asn Gln Thr Val Leu His
                245                 250                 255

Asp Thr Ile Thr Val Lys Ala Gly Gln Val Phe Asp Gly Lys Gly Gln
                260                 265                 270

Thr Phe Thr Ala Gly Ser Glu Leu Gly Asp Gly Gln Ser Glu Asn
            275                 280                 285

Gln Lys Pro Leu Phe Ile Leu Glu Asp Gly Ala Ser Leu Lys Asn Val
    290                 295                 300

Thr Met Gly Asp Asp Gly Ala Asp Gly Ile His Leu Tyr Gly Asp Ala
305                 310                 315                 320

Lys Ile Asp Asn Leu His Val Thr Asn Val Gly Glu Asp Ala Ile Thr
                325                 330                 335

Val Lys Pro Asn Ser Ala Gly Lys Lys Ser His Val Glu Ile Thr Asn
                340                 345                 350

Ser Ser Phe Glu His Ala Ser Asp Lys Ile Leu Gln Leu Asn Ala Asp
            355                 360                 365

Thr Asn Leu Ser Val Asp Asn Val Lys Ala Lys Asp Phe Gly Thr Phe
    370                 375                 380

Val Arg Thr Asn Gly Gly Gln Gln Gly Asn Trp Asp Leu Asn Leu Ser
385                 390                 395                 400

His Ile Ser Ala Glu Asp Gly Lys Phe Ser Phe Val Lys Ser Asp Ser
                405                 410                 415

Glu Gly Leu Asn Val Asn Thr Ser Asp Ile Ser Leu Gly Asp Val Glu
            420                 425                 430

Asn His Tyr Lys Val Pro Met Ser Ala Asn Leu Lys Val Ala Glu
            435                 440                 445

<210> SEQ ID NO 7
<211> LENGTH: 5517
<212> TYPE: DNA
<213> ORGANISM: Erwinia amylovora

<400> SEQUENCE: 7
atggaattaa aatcactggg aactgaacac aaggcggcag tacacacagc ggcgcacaac      60
cctgtggggc atggtgttgc cttacagcag ggcagcagca gcagcagccc gcaaaatgcc     120
gctgcatcat tggcggcaga aggcaaaaat cgtgggaaaa tgccgagaat tcaccagcca     180
tctactgcgg ctgatggtat cagcgctgct caccagcaaa agaaatcctt cagtctcagg     240
ggctgtttgg ggacgaaaaa attttccaga tcggcaccgc agggccagcc aggtaccacc     300
cacagcaaag gggcaacatt gcgcgatctg ctggcgcggg acgacggcga aacgcagcat     360
gaggcggccg cgccagatgc ggcgcgtttg acccgttcgg gcggcgtcaa cgccgcaat     420 atggacgaca tggccgggcg gccaatggtg aaaggtggca gcggcgaaga taaggtacca     480
acgcagcaaa aacggcatca gctgaacaat tttggccaga tgcgccaaac gatgttgagc     540
aaaatggctc acccggcttc agccaacgcc ggcgatcgcc tgcagcattc accgccgcac     600
atcccgggta gccaccacga aatcaaggaa gaaccggttg gctccaccag caaggcaaca     660
acggcccacg cagacagagt ggaaatcgct caggaagatg acgacagcga attccagcaa     720
ctgcatcaac agcggctggc gcgcgaacgg gaaaatccac cgcagccgcc caaactcggc     780
```

```
gttgccacac cgattagcgc caggtttcag cccaaactga ctgcggttgc ggaaagcgtc    840
cttgaggga  cagataccac gcagtcaccc cttaagccgc aatcaatgct gaaaggaagt    900
ggagccgggg taacgccgct ggcggtaacg ctggataaag gcaagttgca gctggcaccg    960
gataatccac ccgcgctcaa tacgttgttg aagcagacat tgggtaaaga cacccagcac   1020
tatctggcgc accatgccag cagcgacggt agccagcatc tgctgctgga caacaaaggc   1080
cacctgtttg atatcaaaag caccgccacc agctatagcg tgctgcacaa cagccacccc   1140
ggtgagataa agggcaagct ggcgcaggcg ggtactggct ccgtcagcgt agacggtaaa   1200
agcggcaaga tctcgctggg gagcggtacg caaagtcaca acaaaacaat gctaagccaa   1260
ccgggggaag cgcaccgttc cttattaacc ggcatttggc agcatcctgc tggcgcagcg   1320
cggccgcagg gcgagtcaat ccgcctgcat gacgacaaaa ttcatatcct gcatccggag   1380
ctgggcgtat ggcaatctgc ggataaagat acccacagcc agctgtctcg ccaggcagac   1440
ggtaagctct atgcgctgaa agacaaccgt accctgcaaa acctctccga taataaatcc   1500
tcagaaaagc tggtcgataa aatcaaatcg tattccgttg atcagcgggg gcaggtggcg   1560
atcctgacgg atactcccgg ccgccataag atgagtatta tgccctcgct ggatgcttcc   1620
ccggagagcc atatttccct cagcctgcat tttgccgatg cccaccaggg gttattgcac   1680
gggaagtcgg agcttgaggc acaatctgtc gcgatcagcc atgggcgact ggttgtggcc   1740
gatagcgaag gcaagctgtt tagcgccgcc attccgaagc aagggatgg  aaacgaactg   1800
aaaatgaaag ccatgcctca gcatgcgctc gatgaacatt ttggtcatga ccaccagatt   1860
tctggatttt tccatgacga ccacggccag cttaatgcgc tggtgaaaaa taacttcagg   1920
cagcagcatg cctgcccgtt gggtaacgat catcagtttc accccggctg gaacctgact   1980
gatgcgctgg ttatcgacaa tcagctgggg ctgcatcata ccaatcctga accgcatgag   2040
attcttgata tggggcattt aggcagcctg gcgttacagg agggcaagct tcactatttt   2100
gaccagctga ccaaagggtg gactggcgcg gagtcagatt gtaagcagct gaaaaaaggc   2160
ctggatggag cagcttatct actgaaagac ggtgaagtga acgcctgaa  tattaatcag   2220
agcacctcct ctatcaagca cggaacggaa aacgtttttt cgctgccgca tgtgcgcaat   2280
aaaccggagc cggagatgc  cctgcaaggg ctgaataaag acgataaggc ccaggccatg   2340
gcggtgattg gggtaaataa atacctggcg ctgacggaaa aagggacat  tcgctccttc   2400
cagataaaac ccggcaccca gcagttggag cggccggcac aaactctcag ccgcgaaggt   2460
atcagcggcg aactgaaaga cattcatgtc gaccacaagc agaacctgta tgccttgacc   2520
cacgagggag aggtgtttca tcagccgcgt gaagcctggc agaatggtgc cgaaagcagc   2580
agctggcaca aactggcgtt gccacagagt gaaagtaagc taaaaagtct ggacatgagc   2640
catgagcaca aaccgattgc caccttttgaa gacggtagcc agcatcagct gaaggctggc   2700
ggctggcacg cctatgcggc acctgaacgc gggccgctgg cggtgggtac cagcggttca   2760
caaaccgtct ttaaccgact aatgcagggg gtgaaaggca aggtgatccc aggcagcggg   2820
ttgacggtta agctctcggc tcagacgggg ggaatgaccg gcgccgaagg gcgcaaggtc   2880
agcagtaaat tttccgaaag gatccgcgcc tatgcgttca acccaacaat gtccacgccg   2940
cgaccgatta aaaatgctgc ttatgccaca cagcacggct ggcaggggcg tgagggttg   3000
aagccgttgt acgagatgca gggagcgctg attaaacaac tggatgcgca taacgttcgt   3060
cataacgcgc cacagccaga tttgcagagc aaactggaaa ctctggattt aggcgaacat   3120
ggcgcagaat tgcttaacga catgaagcgc ttccgcgacg aactggagca gagtgcaacc   3180
```

```
cgttcggtga ccgttttagg tcaacatcag ggagtgctaa aaagcaacgg tgaaatcaat    3240
agcgaattta agccatcgcc cggcaaggcg ttggtccaga gctttaacgt caatcgctct    3300
ggtcaggatc taagcaagtc actgcaacag gcagtacatg ccacgccgcc atccgcagag    3360
agtaaactgc aatccatgct ggggcacttt gtcagtgccg gggtggatat gagtcatcag    3420
aagggcgaga tcccgctggg ccgccagcgc gatccgaatg ataaaaccgc actgaccaaa    3480
tcgcgtttaa ttttagatac cgtgaccatc ggtgaactgc atgaactggc cgataaggcg    3540
aaactggtat ctgaccataa acccgatgcc gatcagataa aacagctgcg ccagcagttc    3600
gatacgctgc gtgaaaagcg gtatgagagc aatccggtga agcattacac cgatatgggc    3660
ttcacccata taaggcgct ggaagcaaac tatgatgcgg tcaaagcctt tatcaatgcc    3720
tttaagaaag agcaccacgg cgtcaatctg accacgcgta ccgtactgga atcacagggc    3780 agtgcgagc tggcgaagaa gctcaagaat acgctgttgt ccctggacag tggtgaaagt    3840
atgagcttca gccggtcata tggcgggggc gtcagcactg tctttgtgcc tacccttagc    3900
aagaaggtgc cagttccggt gatccccgga gccggcatca cgctggatcg cgcctataac    3960
ctgagcttca gtcgtaccag cggcggattg aacgtcagtt ttggccgcga cggcggggtg    4020
agtggtaaca tcatggtcgc taccggccat gatgtgatgc cctatatgac cggtaagaaa    4080
accagtgcag gtaacgccag tgactggttg agcgcaaaac ataaaatcag cccggacttg    4140
cgtatcggcg ctgctgtgag tggcaccctg caaggaacgc tacaaaacag cctgaagttt    4200
aagctgacag aggatgagct gcctggcttt atccatggct tgacgcatgg cacgttgacc    4260
ccggcagaac tgttgcaaaa ggggatcgaa catcagatga gcagggcag caaactgacg    4320 tttagcgtcg ataccctcggc aaatctggat ctgcgtgccg gtatcaatct gaacgaagac    4380
ggcagtaaac caaatggtgt cactgcccgt gtttctgccg ggctaagtgc atcggcaaac    4440
ctggccgccg gctcgcgtga acgcagcacc acctctggcc agtttggcag cacgacttcg    4500
gccagcaata accgcccaac cttcctcaac ggggtcggcg cgggtgctaa cctgacggct    4560
gctttagggg ttgcccattc atctacgcat gaagggaaac cggtcgggat cttcccggca    4620
tttacctcga ccaatgtttc ggcagcgctg gcgctggata accgtacctc acagagtatc    4680
agcctggaat tgaagcgcgc ggagccggtg accagcaacg atatcagcga gttgacctcc    4740
acgctgggaa aacactttaa ggatagcgcc acaacgaaga tgcttgccgc tctcaaagag    4800
ttagatgacg ctaagcccgc tgaacaactg catattttac agcagcattt cagtgcaaaa    4860
gatgtcgtcg gtgatgaacg ctacgaggcg gtgcgcaacc tgaaaaaact ggtgatacgt    4920
caacaggctg cggacagcca cagcatggaa ttaggatctg ccagtcacag cacgacctac    4980
aataatctgt cgagaataaa taatgacggc attgtcgagc tgctacacaa acatttcgat    5040
gcggcattac cagcaagcag tgccaaacgt cttggtgaaa tgatgaataa cgatccggca    5100
ctgaaagata ttattaagca gctgcaaagt acgccgttca gcagcgccag cgtgtcgatg    5160
gagctgaaag atggtctgcg tgagcagacg gaaaaagcaa tactggacgg taaggtcggt    5220
cgtgaagaag tgggagtact tttccaggat cgtaacaact gcgtgttaa atcggtcagc    5280 gtcagtcagt ccgtcagcaa aagcgaaggc ttcaataccc cagcgctgtt actggggacg    5340
agcaacagcg ctgctatgag catggagcgc aacatcggaa ccattaattt taaatacggc    5400
caggatcaga acacccccacg gcgatttacc ctggagggtg aatagctca ggctaatccg    5460 caggtcgcat ctgcgcttac tgatttgaag aaggaagggc tggaaatgaa gagctaa      5517
```

-continued

<210> SEQ ID NO 8
<211> LENGTH: 1838
<212> TYPE: PRT
<213> ORGANISM: Erwinia amylovora

<400> SEQUENCE: 8
```
Met Glu Leu Lys Ser Leu Gly Thr Glu His Lys Ala Ala Val His Thr
  1               5                  10                  15

Ala Ala His Asn Pro Val Gly His Gly Val Ala Leu Gln Gln Gly Ser
             20                  25                  30

Ser Ser Ser Ser Pro Gln Asn Ala Ala Ala Ser Leu Ala Ala Glu Gly
         35                  40                  45

Lys Asn Arg Gly Lys Met Pro Arg Ile His Gln Pro Ser Thr Ala Ala
     50                  55                  60

Asp Gly Ile Ser Ala Ala His Gln Gln Lys Lys Ser Phe Ser Leu Arg
 65                  70                  75                  80

Gly Cys Leu Gly Thr Lys Lys Phe Ser Arg Ser Ala Pro Gln Gly Gln
                 85                  90                  95

Pro Gly Thr Thr His Ser Lys Gly Ala Thr Leu Arg Asp Leu Leu Ala
            100                 105                 110

Arg Asp Asp Gly Glu Thr Gln His Glu Ala Ala Ala Pro Asp Ala Ala
        115                 120                 125

Arg Leu Thr Arg Ser Gly Gly Val Lys Arg Arg Asn Met Asp Asp Met
    130                 135                 140

Ala Gly Arg Pro Met Val Lys Gly Gly Ser Gly Glu Asp Lys Val Pro
145                 150                 155                 160

Thr Gln Gln Lys Arg His Gln Leu Asn Asn Phe Gly Gln Met Arg Gln
                165                 170                 175

Thr Met Leu Ser Lys Met Ala His Pro Ala Ser Ala Asn Ala Gly Asp
            180                 185                 190

Arg Leu Gln His Ser Pro Pro His Ile Pro Gly Ser His His Glu Ile
        195                 200                 205

Lys Glu Glu Pro Val Gly Ser Thr Ser Lys Ala Thr Thr Ala His Ala
    210                 215                 220

Asp Arg Val Glu Ile Ala Gln Glu Asp Asp Asp Ser Glu Phe Gln Gln
225                 230                 235                 240

Leu His Gln Gln Arg Leu Ala Arg Glu Arg Glu Asn Pro Pro Gln Pro
                245                 250                 255

Pro Lys Leu Gly Val Ala Thr Pro Ile Ser Ala Arg Phe Gln Pro Lys
            260                 265                 270

Leu Thr Ala Val Ala Glu Ser Val Leu Glu Gly Thr Asp Thr Thr Gln
        275                 280                 285

Ser Pro Leu Lys Pro Gln Ser Met Leu Lys Gly Ser Gly Ala Gly Val
    290                 295                 300

Thr Pro Leu Ala Val Thr Leu Asp Lys Gly Lys Leu Gln Leu Ala Pro
305                 310                 315                 320

Asp Asn Pro Pro Ala Leu Asn Thr Leu Leu Lys Gln Thr Leu Gly Lys
                325                 330                 335

Asp Thr Gln His Tyr Leu Ala His His Ala Ser Ser Asp Gly Ser Gln
            340                 345                 350

His Leu Leu Leu Asp Asn Lys Gly His Leu Phe Asp Ile Lys Ser Thr
        355                 360                 365

Ala Thr Ser Tyr Ser Val Leu His Asn Ser His Pro Gly Glu Ile Lys
    370                 375                 380
```

-continued

```
Gly Lys Leu Ala Gln Ala Gly Thr Gly Ser Val Ser Val Asp Gly Lys
385                 390                 395                 400

Ser Gly Lys Ile Ser Leu Gly Ser Gly Thr Gln Ser His Asn Lys Thr
            405                 410                 415

Met Leu Ser Gln Pro Gly Glu Ala His Arg Ser Leu Leu Thr Gly Ile
                420                 425                 430

Trp Gln His Pro Ala Gly Ala Ala Arg Pro Gln Gly Glu Ser Ile Arg
            435                 440                 445

Leu His Asp Asp Lys Ile His Ile Leu His Pro Glu Leu Gly Val Trp
450                 455                 460

Gln Ser Ala Asp Lys Asp Thr His Ser Gln Leu Ser Arg Gln Ala Asp
465                 470                 475                 480

Gly Lys Leu Tyr Ala Leu Lys Asp Asn Arg Thr Leu Gln Asn Leu Ser
                485                 490                 495

Asp Asn Lys Ser Ser Glu Lys Leu Val Asp Lys Ile Lys Ser Tyr Ser
            500                 505                 510

Val Asp Gln Arg Gly Gln Val Ala Ile Leu Thr Asp Thr Pro Gly Arg
                515                 520                 525

His Lys Met Ser Ile Met Pro Ser Leu Asp Ala Ser Pro Glu Ser His
            530                 535                 540

Ile Ser Leu Ser Leu His Phe Ala Asp Ala His Gln Gly Leu Leu His
545                 550                 555                 560

Gly Lys Ser Glu Leu Glu Ala Gln Ser Val Ala Ile Ser His Gly Arg
                565                 570                 575

Leu Val Val Ala Asp Ser Glu Gly Lys Leu Phe Ser Ala Ala Ile Pro
            580                 585                 590

Lys Gln Gly Asp Gly Asn Glu Leu Lys Met Lys Ala Met Pro Gln His
        595                 600                 605

Ala Leu Asp Glu His Phe Gly His Asp His Gln Ile Ser Gly Phe Phe
            610                 615                 620

His Asp Asp His Gly Gln Leu Asn Ala Leu Val Lys Asn Asn Phe Arg
625                 630                 635                 640

Gln Gln His Ala Cys Pro Leu Gly Asn Asp His Gln Phe His Pro Gly
                645                 650                 655

Trp Asn Leu Thr Asp Ala Leu Val Ile Asp Asn Gln Leu Gly Leu His
            660                 665                 670

His Thr Asn Pro Glu Pro His Glu Ile Leu Asp Met Gly His Leu Gly
        675                 680                 685

Ser Leu Ala Leu Gln Glu Gly Lys Leu His Tyr Phe Asp Gln Leu Thr
690                 695                 700

Lys Gly Trp Thr Gly Ala Glu Ser Asp Cys Lys Gln Leu Lys Lys Gly
705                 710                 715                 720

Leu Asp Gly Ala Ala Tyr Leu Leu Lys Asp Gly Glu Val Lys Arg Leu
                725                 730                 735

Asn Ile Asn Gln Ser Thr Ser Ser Ile Lys His Gly Thr Glu Asn Val
            740                 745                 750

Phe Ser Leu Pro His Val Arg Asn Lys Pro Glu Pro Gly Asp Ala Leu
                755                 760                 765

Gln Gly Leu Asn Lys Asp Asp Lys Ala Gln Ala Met Ala Val Ile Gly
        770                 775                 780

Val Asn Lys Tyr Leu Ala Leu Thr Glu Lys Gly Asp Ile Arg Ser Phe
785                 790                 795                 800
```

-continued

```
Gln Ile Lys Pro Gly Thr Gln Leu Glu Arg Pro Ala Gln Thr Leu
            805                 810                 815

Ser Arg Glu Gly Ile Ser Gly Glu Leu Lys Asp Ile His Val Asp His
            820                 825                 830

Lys Gln Asn Leu Tyr Ala Leu Thr His Glu Gly Glu Val Phe His Gln
            835                 840                 845

Pro Arg Glu Ala Trp Gln Asn Gly Ala Glu Ser Ser Trp His Lys
            850                 855                 860

Leu Ala Leu Pro Gln Ser Glu Ser Lys Leu Lys Ser Leu Asp Met Ser
865                 870                 875                 880

His Glu His Lys Pro Ile Ala Thr Phe Glu Asp Gly Ser Gln His Gln
            885                 890                 895

Leu Lys Ala Gly Gly Trp His Ala Tyr Ala Ala Pro Glu Arg Gly Pro
            900                 905                 910

Leu Ala Val Gly Thr Ser Gly Ser Gln Thr Val Phe Asn Arg Leu Met
            915                 920                 925

Gln Gly Val Lys Gly Lys Val Ile Pro Gly Ser Gly Leu Thr Val Lys
            930                 935                 940

Leu Ser Ala Gln Thr Gly Gly Met Thr Gly Ala Glu Gly Arg Lys Val
945                 950                 955                 960

Ser Ser Lys Phe Ser Glu Arg Ile Arg Ala Tyr Ala Phe Asn Pro Thr
            965                 970                 975

Met Ser Thr Pro Arg Pro Ile Lys Asn Ala Ala Tyr Ala Thr Gln His
            980                 985                 990

Gly Trp Gln Gly Arg Glu Gly Leu Lys Pro Leu Tyr Glu Met Gln Gly
            995                 1000                1005

Ala Leu Ile Lys Gln Leu Asp Ala His Asn Val Arg His Asn Ala Pro
1010                1015                1020

Gln Pro Asp Leu Gln Ser Lys Leu Glu Thr Leu Asp Leu Gly Glu His
1025                1030                1035                1040

Gly Ala Glu Leu Leu Asn Asp Met Lys Arg Phe Arg Asp Glu Leu Glu
            1045                1050                1055

Gln Ser Ala Thr Arg Ser Val Thr Val Leu Gly Gln His Gln Gly Val
            1060                1065                1070

Leu Lys Ser Asn Gly Glu Ile Asn Ser Glu Phe Lys Pro Ser Pro Gly
            1075                1080                1085

Lys Ala Leu Val Gln Ser Phe Asn Val Asn Arg Ser Gly Gln Asp Leu
1090                1095                1100

Ser Lys Ser Leu Gln Gln Ala Val His Ala Thr Pro Pro Ser Ala Glu
1105                1110                1115                1120

Ser Lys Leu Gln Ser Met Leu Gly His Phe Val Ser Ala Gly Val Asp
            1125                1130                1135

Met Ser His Gln Lys Gly Glu Ile Pro Leu Gly Arg Gln Arg Asp Pro
            1140                1145                1150

Asn Asp Lys Thr Ala Leu Thr Lys Ser Arg Leu Ile Leu Asp Thr Val
            1155                1160                1165

Thr Ile Gly Glu Leu His Glu Leu Ala Asp Lys Ala Lys Leu Val Ser
            1170                1175                1180

Asp His Lys Pro Asp Ala Asp Gln Ile Lys Gln Leu Arg Gln Gln Phe
1185                1190                1195                1200

Asp Thr Leu Arg Glu Lys Arg Tyr Glu Ser Asn Pro Val Lys His Tyr
            1205                1210                1215

Thr Asp Met Gly Phe Thr His Asn Lys Ala Leu Glu Ala Asn Tyr Asp
```

-continued

```
                1220              1225              1230
Ala Val Lys Ala Phe Ile Asn Ala Phe Lys Lys Glu His His Gly Val
            1235              1240              1245

Asn Leu Thr Thr Arg Thr Val Leu Glu Ser Gln Gly Ser Ala Glu Leu
1250              1255              1260

Ala Lys Lys Leu Lys Asn Thr Leu Leu Ser Leu Asp Ser Gly Glu Ser
1265              1270              1275              1280

Met Ser Phe Ser Arg Ser Tyr Gly Gly Gly Val Ser Thr Val Phe Val
            1285              1290              1295

Pro Thr Leu Ser Lys Lys Val Pro Val Pro Val Ile Pro Gly Ala Gly
            1300              1305              1310

Ile Thr Leu Asp Arg Ala Tyr Asn Leu Ser Phe Ser Arg Thr Ser Gly
            1315              1320              1325

Gly Leu Asn Val Ser Phe Gly Arg Asp Gly Val Ser Gly Asn Ile
            1330              1335              1340

Met Val Ala Thr Gly His Asp Val Met Pro Tyr Met Thr Gly Lys Lys
1345              1350              1355              1360

Thr Ser Ala Gly Asn Ala Ser Asp Trp Leu Ser Ala Lys His Lys Ile
            1365              1370              1375

Ser Pro Asp Leu Arg Ile Gly Ala Ala Val Ser Gly Thr Leu Gln Gly
            1380              1385              1390

Thr Leu Gln Asn Ser Leu Lys Phe Lys Leu Thr Glu Asp Glu Leu Pro
            1395              1400              1405

Gly Phe Ile His Gly Leu Thr His Gly Thr Leu Thr Pro Ala Glu Leu
            1410              1415              1420

Leu Gln Lys Gly Ile Glu His Gln Met Lys Gln Gly Ser Lys Leu Thr
1425              1430              1435              1440

Phe Ser Val Asp Thr Ser Ala Asn Leu Asp Leu Arg Ala Gly Ile Asn
            1445              1450              1455

Leu Asn Glu Asp Gly Ser Lys Pro Asn Gly Val Thr Ala Arg Val Ser
            1460              1465              1470

Ala Gly Leu Ser Ala Ser Ala Asn Leu Ala Ala Gly Ser Arg Glu Arg
            1475              1480              1485

Ser Thr Thr Ser Gly Gln Phe Gly Ser Thr Thr Ser Ala Ser Asn Asn
            1490              1495              1500

Arg Pro Thr Phe Leu Asn Gly Val Gly Ala Gly Ala Asn Leu Thr Ala
1505              1510              1515              1520

Ala Leu Gly Val Ala His Ser Ser Thr His Glu Gly Lys Pro Val Gly
            1525              1530              1535

Ile Phe Pro Ala Phe Thr Ser Thr Asn Val Ser Ala Ala Leu Ala Leu
            1540              1545              1550

Asp Asn Arg Thr Ser Gln Ser Ile Ser Leu Glu Leu Lys Arg Ala Glu
            1555              1560              1565

Pro Val Thr Ser Asn Asp Ile Ser Glu Leu Thr Ser Thr Leu Gly Lys
            1570              1575              1580

His Phe Lys Asp Ser Ala Thr Thr Lys Met Leu Ala Ala Leu Lys Glu
1585              1590              1595              1600

Leu Asp Asp Ala Lys Pro Ala Glu Gln Leu His Ile Leu Gln Gln His
            1605              1610              1615

Phe Ser Ala Lys Asp Val Val Gly Asp Glu Arg Tyr Glu Ala Val Arg
            1620              1625              1630

Asn Leu Lys Lys Leu Val Ile Arg Gln Gln Ala Ala Asp Ser His Ser
            1635              1640              1645
```

-continued

Met Glu Leu Gly Ser Ala Ser His Ser Thr Thr Tyr Asn Asn Leu Ser
      1650                1655                1660

Arg Ile Asn Asn Asp Gly Ile Val Glu Leu Leu His Lys His Phe Asp
1665                1670                1675                1680

Ala Ala Leu Pro Ala Ser Ser Ala Lys Arg Leu Gly Glu Met Met Asn
          1685                1690                1695

Asn Asp Pro Ala Leu Lys Asp Ile Ile Lys Gln Leu Gln Ser Thr Pro
              1700                1705                1710

Phe Ser Ser Ala Ser Val Ser Met Glu Leu Lys Asp Gly Leu Arg Glu
          1715                1720                1725

Gln Thr Glu Lys Ala Ile Leu Asp Gly Lys Val Gly Arg Glu Glu Val
      1730                1735                1740

Gly Val Leu Phe Gln Asp Arg Asn Asn Leu Arg Val Lys Ser Val Ser
1745                1750                1755                1760

Val Ser Gln Ser Val Ser Lys Ser Glu Gly Phe Asn Thr Pro Ala Leu
              1765                1770                1775

Leu Leu Gly Thr Ser Asn Ser Ala Ala Met Ser Met Glu Arg Asn Ile
          1780                1785                1790

Gly Thr Ile Asn Phe Lys Tyr Gly Gln Asp Gln Asn Thr Pro Arg Arg
      1795                1800                1805

Phe Thr Leu Glu Gly Gly Ile Ala Gln Ala Asn Pro Gln Val Ala Ser
    1810                1815                1820

Ala Leu Thr Asp Leu Lys Lys Glu Gly Leu Glu Met Lys Ser
1825                1830                1835

<210> SEQ ID NO 9
<211> LENGTH: 420
<212> TYPE: DNA
<213> ORGANISM: Erwinia amylovora

<400> SEQUENCE: 9
atgacatcgt cacagcagcg ggttgaaagg ttttttacagt atttctccgc cgggtgtaaa     60
acgcccatac atctgaaaga cggggtgtgc gccctgtata cgaacaaga tgaggaggcg     120 gcggtgctgg aagtaccgca acacagcgac agcctgttac tacactgccg aatcattgag     180
gctgacccac aaacttcaat aaccctgtat tcgatgctat tacagctgaa ttttgaaatg     240
gcggccatgc gcggctgttg gctggcgctg gatgaactgc acaacgtgcg tttatgtttt     300
cagcagtcgc tggagcatct ggatgaagca agttttagcg atatcgttag cggcttcatc     360
gaacatgcgg cagaagtgcg tgagtatata gcgcaattag acgagagtag cgcggcataa     420

<210> SEQ ID NO 10
<211> LENGTH: 139
<212> TYPE: PRT
<213> ORGANISM: Erwinia amylovora

<400> SEQUENCE: 10

Met Thr Ser Ser Gln Gln Arg Val Glu Arg Phe Leu Gln Tyr Phe Ser
  1                 5                  10                  15

Ala Gly Cys Lys Thr Pro Ile His Leu Lys Asp Gly Val Cys Ala Leu
              20                  25                  30

Tyr Asn Glu Gln Asp Glu Glu Ala Val Leu Glu Val Pro Gln His
          35                  40                  45

Ser Asp Ser Leu Leu His Cys Arg Ile Ile Glu Ala Asp Pro Gln
      50                  55                  60

```
Thr Ser Ile Thr Leu Tyr Ser Met Leu Leu Gln Leu Asn Phe Glu Met
 65                  70                  75                  80

Ala Ala Met Arg Gly Cys Trp Leu Ala Leu Asp Glu Leu His Asn Val
                 85                  90                  95

Arg Leu Cys Phe Gln Gln Ser Leu Glu His Leu Asp Glu Ala Ser Phe
                100                 105                 110

Ser Asp Ile Val Ser Gly Phe Ile Glu His Ala Ala Glu Val Arg Glu
            115                 120                 125

Tyr Ile Ala Gln Leu Asp Glu Ser Ser Ala Ala
        130                 135

<210> SEQ ID NO 11
<211> LENGTH: 341
<212> TYPE: PRT
<213> ORGANISM: Pseudomonas syringae

<400> SEQUENCE: 11

Met Gln Ser Leu Ser Leu Asn Ser Ser Leu Gln Thr Pro Ala Met
  1               5                  10                  15

Ala Leu Val Leu Val Arg Pro Glu Ala Glu Thr Thr Gly Ser Thr Ser
                 20                  25                  30

Ser Lys Ala Leu Gln Glu Val Val Lys Leu Ala Glu Glu Leu Met
         35                  40                  45

Arg Asn Gly Gln Leu Asp Asp Ser Ser Pro Leu Gly Lys Leu Leu Ala
     50                  55                  60

Lys Ser Met Ala Ala Asp Gly Lys Ala Gly Gly Ile Glu Asp Val
 65                  70                  75                  80

Ile Ala Ala Leu Asp Lys Leu Ile His Glu Lys Leu Gly Asp Asn Phe
                 85                  90                  95

Gly Ala Ser Ala Asp Ser Ala Ser Gly Thr Gly Gln Gln Asp Leu Met
                100                 105                 110

Thr Gln Val Leu Asn Gly Leu Ala Lys Ser Met Leu Asp Asp Leu Leu
            115                 120                 125

Thr Lys Gln Asp Gly Gly Thr Ser Phe Ser Glu Asp Met Pro Met
130                 135                 140

Leu Asn Lys Ile Ala Gln Phe Met Asp Asp Asn Pro Ala Gln Phe Pro
145                 150                 155                 160

Lys Pro Asp Ser Gly Ser Trp Val Asn Glu Leu Lys Glu Asp Asn Phe
                165                 170                 175

Leu Asp Gly Asp Glu Thr Ala Ala Phe Arg Ser Ala Leu Asp Ile Ile
            180                 185                 190

Gly Gln Gln Leu Gly Asn Gln Gln Ser Asp Ala Gly Ser Leu Ala Gly
        195                 200                 205

Thr Gly Gly Leu Gly Thr Pro Ser Ser Phe Ser Asn Asn Ser Ser
210                 215                 220

Val Met Gly Asp Pro Leu Ile Asp Ala Asn Thr Gly Pro Gly Asp Ser
225                 230                 235                 240

Gly Asn Thr Arg Gly Glu Ala Gly Gln Leu Ile Gly Glu Leu Ile Asp
                245                 250                 255

Arg Gly Leu Gln Ser Val Leu Ala Gly Gly Leu Gly Thr Pro Val
            260                 265                 270

Asn Thr Pro Gln Thr Gly Thr Ser Ala Asn Gly Gly Gln Ser Ala Gln
        275                 280                 285

Asp Leu Asp Gln Leu Leu Gly Leu Leu Leu Lys Gly Leu Glu Ala
    290                 295                 300
```

```
Thr Leu Lys Asp Ala Gly Gln Thr Gly Thr Asp Val Gln Ser Ser Ala
305                 310                 315                 320

Ala Gln Ile Ala Thr Leu Leu Val Ser Thr Leu Leu Gln Gly Thr Arg
            325                 330                 335

Asn Gln Ala Ala Ala
            340

<210> SEQ ID NO 12
<211> LENGTH: 1026
<212> TYPE: DNA
<213> ORGANISM: Pseudomonas syringae

<400> SEQUENCE: 12
atgcagagtc tcagtcttaa cagcagctcg ctgcaaaccc cggcaatggc ccttgtcctg      60
gtacgtcctg aagccgagac gactggcagt acgtcgagca aggcgcttca ggaagttgtc     120
gtgaagctgg ccgaggaact gatgcgcaat ggtcaactcg acgacagctc gccattggga     180
aaactgttgg ccaagtcgat ggccgcagat ggcaaggcgg cggcggtat  tgaggatgtc     240 atcgctgcgc tggacaagct gatccatgaa agctcggtg  acaacttcgg cgcgtctgcg     300
gacagcgcct cgggtaccgg acagcaggac ctgatgactc aggtgctcaa tggcctggcc     360
aagtcgatgc tcgatgatct tctgaccaag caggatggcg ggacaagctt ctccgaagac     420
gatatgccga tgctgaacaa gatcgcgcag ttcatggatg acaatcccgc acagtttccc     480
aagccggact cgggctcctg ggtgaacgaa ctcaaggaag acaacttcct tgatggcgac     540
gaaacggctg cgttccgttc ggcactcgac atcattggcc agcaactggg taatcagcag     600
agtgacgctg gcagtctggc agggacgggt ggaggtctgg gcactccgag cagtttttcc     660
aacaactcgt ccgtgatggg tgatccgctg atcgacgcca ataccggtcc cggtgacagc     720
ggcaataccc gtggtgaagc ggggcaactg atcggcgagc ttatcgaccg tggcctgcaa     780
tcggtattgg ccggtggtgg actgggcaca cccgtaaaca ccccgcagac cggtacgtcg     840
gcgaatggcg gacagtccgc tcaggatctt gatcagttgc tgggcggctt gctgctcaag     900
ggcctggagg caacgctcaa ggatgccggg caaacaggca ccgacgtgca gtcgagcgct     960
gcgcaaatcg ccaccttgct ggtcagtacg ctgctgcaag gcacccgcaa tcaggctgca    1020
gcctga                                                              1026

<210> SEQ ID NO 13
<211> LENGTH: 1729
<212> TYPE: DNA
<213> ORGANISM: Pseudomonas syringae

<400> SEQUENCE: 13
tccacttcgc tgattttgaa attggcagat tcatagaaac gttcaggtgt ggaaatcagg      60
ctgagtgcgc agatttcgtt gataagggtg tggtactggt cattgttggt catttcaagg     120
cctctgagtg cggtgcggag caataccagt cttcctgctg gcgtgtgcac actgagtcgc     180
aggcataggc atttcagttc cttgcgttgg ttgggcatat aaaaaaagga acttttaaaa     240
acagtgcaat gagatgccgg caaaacggga accggtcgct cgctttgcc  actcacttcg     300 agcaagctca accccaaaca tccacatccc tatcgaacgg acagcgatac ggccacttgc     360
tctggtaaac cctggagctg gcgtcggtcc aattgcccac ttagcgaggt aacgcagcat     420
gagcatcggc atcacacccc ggccgcaaca gaccaccacg ccactcgatt tttcggcgct     480
aagcggcaag agtcctcaac caaacacgtt cggcgagcag aacactcagc aagcgatcga     540
```

-continued

```
cccgagtgca ctgttgttcg gcagcgacac acagaaagac gtcaacttcg gcacgcccga    600
cagcaccgtc cagaatccgc aggacgccag caagcccaac gacagccagt ccaacatcgc    660
taaattgatc agtgcattga tcatgtcgtt gctgcagatg ctcaccaact ccaataaaaa    720
gcaggacacc aatcaggaac agcctgatag ccaggctcct ttccagaaca acggcgggct    780
cggtacaccg tcggccgata gcgggggcgg cggtacaccg gatgcgacag gtggcggcgg    840
cggtgatacg ccaagcgcaa caggcggtgg cggcggtgat actccgaccg caacaggcgg    900
tggcggcagc ggtggcggcg gcacacccac tgcaacaggt ggcggcagcg gtggcacacc    960
cactgcaaca ggcggtggcg agggtggcgt aacaccgcaa atcactccgc agttggccaa   1020
ccctaaccgt acctcaggta ctggctcggt gtcggacacc gcaggttcta ccgagcaagc   1080
cggcaagatc aatgtggtga agacaccat caaggtcggc gctggcgaag tctttgacgg   1140
ccacggcgca accttcactg ccgacaaatc tatgggtaac ggagaccagg gcgaaaatca   1200
gaagcccatg ttcgagctgg ctgaaggcgc tacgttgaag aatgtgaacc tgggtgagaa   1260
cgaggtcgat ggcatccacg tgaaagccaa aaacgctcag gaagtcacca ttgacaacgt   1320
gcatgcccag aacgtcggtg aagacctgat tacggtcaaa ggcgagggag gcgcagcggt   1380
cactaatctg aacatcaaga acagcagtgc caaaggtgca gacgacaagg ttgtccagct   1440
caacgccaac actcacttga aaatcgacaa cttcaaggcc gacgatttcg gcacgatggt   1500
tcgcaccaac ggtggcaagc agtttgatga catgagcatc gagctgaacg gcatcgaagc   1560
taaccacggc aagttcgccc tggtgaaaag cgacagtgac gatctgaagc tggcaacggg   1620
caacatcgcc atgaccgacg tcaaacacgc ctacgataaa acccaggcat cgacccaaca   1680
caccgagctt tgaatccaga caagtagctt gaaaaaaggg ggtggactc              1729
```

<210> SEQ ID NO 14
<211> LENGTH: 424
<212> TYPE: PRT
<213> ORGANISM: Pseudomonas syringae

<400> SEQUENCE: 14

```
Met Ser Ile Gly Ile Thr Pro Arg Pro Gln Gln Thr Thr Thr Pro Leu
 1               5                  10                  15

Asp Phe Ser Ala Leu Ser Gly Lys Ser Pro Gln Pro Asn Thr Phe Gly
                20                  25                  30

Glu Gln Asn Thr Gln Gln Ala Ile Asp Pro Ser Ala Leu Leu Phe Gly
            35                  40                  45

Ser Asp Thr Gln Lys Asp Val Asn Phe Gly Thr Pro Asp Ser Thr Val
        50                  55                  60

Gln Asn Pro Gln Asp Ala Ser Lys Pro Asn Asp Ser Gln Ser Asn Ile
 65                  70                  75                  80

Ala Lys Leu Ile Ser Ala Leu Ile Met Ser Leu Leu Gln Met Leu Thr
                85                  90                  95

Asn Ser Asn Lys Lys Gln Asp Thr Asn Gln Glu Gln Pro Asp Ser Gln
            100                 105                 110

Ala Pro Phe Gln Asn Asn Gly Gly Leu Gly Thr Pro Ser Ala Asp Ser
        115                 120                 125

Gly Gly Gly Gly Thr Pro Asp Ala Thr Gly Gly Gly Gly Asp Thr
    130                 135                 140

Pro Ser Ala Thr Gly Gly Gly Gly Asp Thr Pro Thr Ala Thr Gly
145                 150                 155                 160
```

-continued

```
Gly Gly Gly Ser Gly Gly Gly Thr Pro Ala Thr Gly Gly
                165                 170                 175

Ser Gly Gly Thr Pro Thr Ala Thr Gly Gly Glu Gly Gly Val Thr
            180                 185                 190

Pro Gln Ile Thr Pro Gln Leu Ala Asn Pro Asn Arg Thr Ser Gly Thr
            195                 200                 205

Gly Ser Val Ser Asp Thr Ala Gly Ser Thr Glu Gln Ala Gly Lys Ile
    210                 215                 220

Asn Val Val Lys Asp Thr Ile Lys Val Gly Ala Gly Glu Val Phe Asp
225                 230                 235                 240

Gly His Gly Ala Thr Phe Thr Ala Asp Lys Ser Met Gly Asn Gly Asp
                245                 250                 255

Gln Gly Glu Asn Gln Lys Pro Met Phe Glu Leu Ala Glu Gly Ala Thr
            260                 265                 270

Leu Lys Asn Val Asn Leu Gly Glu Asn Glu Val Asp Gly Ile His Val
    275                 280                 285

Lys Ala Lys Asn Ala Gln Glu Val Thr Ile Asp Asn Val His Ala Gln
290                 295                 300

Asn Val Gly Glu Asp Leu Ile Thr Val Lys Gly Glu Gly Gly Ala Ala
305                 310                 315                 320

Val Thr Asn Leu Asn Ile Lys Asn Ser Ser Ala Lys Gly Ala Asp Asp
                325                 330                 335

Lys Val Val Gln Leu Asn Ala Asn Thr His Leu Lys Ile Asp Asn Phe
            340                 345                 350

Lys Ala Asp Asp Phe Gly Thr Met Val Arg Thr Asn Gly Lys Gln
            355                 360                 365

Phe Asp Asp Met Ser Ile Glu Leu Asn Gly Ile Glu Ala Asn His Gly
    370                 375                 380

Lys Phe Ala Leu Val Lys Ser Asp Ser Asp Leu Lys Leu Ala Thr
385                 390                 395                 400

Gly Asn Ile Ala Met Thr Asp Val Lys His Ala Tyr Asp Lys Thr Gln
                405                 410                 415

Ala Ser Thr Gln His Thr Glu Leu
            420
```

<210> SEQ ID NO 15
<211> LENGTH: 344
<212> TYPE: PRT
<213> ORGANISM: Pseudomonas solanacearum

<400> SEQUENCE: 15

```
Met Ser Val Gly Asn Ile Gln Ser Pro Ser Asn Leu Pro Gly Leu Gln
  1               5                  10                  15

Asn Leu Asn Leu Asn Thr Asn Thr Asn Ser Gln Gln Ser Gly Gln Ser
                20                  25                  30

Val Gln Asp Leu Ile Lys Gln Val Glu Lys Asp Ile Leu Asn Ile Ile
            35                  40                  45

Ala Ala Leu Val Gln Lys Ala Gln Ser Ala Gly Gly Asn Thr Gly
        50                  55                  60

Asn Thr Gly Asn Ala Pro Ala Lys Asp Gly Asn Ala Asn Ala Gly Ala
 65                  70                  75                  80

Asn Asp Pro Ser Lys Asn Asp Pro Ser Lys Ser Gln Ala Pro Gln Ser
                85                  90                  95

Ala Asn Lys Thr Gly Asn Val Asp Asp Ala Asn Asn Gln Asp Pro Met
            100                 105                 110
```

-continued

```
Gln Ala Leu Met Gln Leu Leu Glu Asp Leu Val Lys Leu Leu Lys Ala
        115                 120                 125

Ala Leu His Met Gln Gln Pro Gly Gly Asn Asp Lys Gly Asn Gly Val
    130                 135                 140

Gly Gly Ala Asn Gly Ala Lys Gly Ala Gly Gly Gln Gly Gly Leu Ala
145                 150                 155                 160

Glu Ala Leu Gln Glu Ile Glu Gln Ile Leu Ala Gln Leu Gly Gly Gly
                165                 170                 175

Gly Ala Gly Ala Gly Gly Ala Gly Gly Gly Val Gly Gly Ala Gly Gly
            180                 185                 190

Ala Asp Gly Gly Ser Gly Ala Gly Gly Ala Gly Gly Ala Asn Gly Ala
        195                 200                 205

Asp Gly Gly Asn Gly Val Asn Gly Asn Gln Ala Asn Gly Pro Gln Asn
    210                 215                 220

Ala Gly Asp Val Asn Gly Ala Asn Gly Ala Asp Asp Gly Ser Glu Asp
225                 230                 235                 240

Gln Gly Gly Leu Thr Gly Val Leu Gln Lys Leu Met Lys Ile Leu Asn
                245                 250                 255

Ala Leu Val Gln Met Met Gln Gln Gly Gly Leu Gly Gly Gly Asn Gln
            260                 265                 270

Ala Gln Gly Gly Ser Lys Gly Ala Gly Asn Ala Ser Pro Ala Ser Gly
        275                 280                 285

Ala Asn Pro Gly Ala Asn Gln Pro Gly Ser Ala Asp Asp Gln Ser Ser
    290                 295                 300

Gly Gln Asn Asn Leu Gln Ser Gln Ile Met Asp Val Val Lys Glu Val
305                 310                 315                 320

Val Gln Ile Leu Gln Gln Met Leu Ala Ala Gln Asn Gly Gly Ser Gln
                325                 330                 335

Gln Ser Thr Ser Thr Gln Pro Met
            340
```

<210> SEQ ID NO 16
<211> LENGTH: 1035
<212> TYPE: DNA
<213> ORGANISM: Pseudomonas solanacearum

<400> SEQUENCE: 16

```
atgtcagtcg gaaacatcca gagcccgtcg aacctcccgg gtctgcagaa cctgaacctc      60
aacaccaaca ccaacagcca gcaatcgggc cagtccgtgc aagacctgat caagcaggtc     120
gagaaggaca tcctcaacat catcgcagcc ctcgtgcaga aggccgcaca gtcggcgggc     180
ggcaacaccg gtaacaccgg caacgcgccg gcgaaggacg gcaatgccaa cgcgggcgcc     240
aacgacccga gcaagaacga cccgagcaag agccaggctc cgcagtcggc caacaagacc     300
ggcaacgtcg acgacgccaa caaccaggat ccgatgcaag cgctgatgca gctgctggaa     360
gacctggtga agctgctgaa ggcggccctg cacatgcagc agcccggcgg caatgacaag     420
ggcaacggcg tgggcggtgc caacggcgcc aagggtgccg gcggccaggg cggcctggcc     480
gaagcgctgc aggagatcga gcagatcctc gcccagctcg gcggcggcgg tgctggcgcc     540
ggcggcgcgg gtggcggtgt cggcggtgct ggtggcgcgg atggcggctc cggtgcgggt     600
ggcgcaggcg gtgcgaacgg cgccgacggc ggcaatggcg tgaacggcaa ccaggcgaac     660
ggcccgcaga acgcaggcga tgtcaacggt gccaacggcg cggatgacgg cagcgaagac     720
cagggcggcc tcaccggcgt gctgcaaaag ctgatgaaga tcctgaacgc gctggtgcag     780
```

-continued

```
atgatgcagc aaggcggcct cggcggcggc aaccaggcgc agggcggctc gaagggtgcc      840
ggcaacgcct cgccggcttc cggcgcgaac ccgggcgcga accagcccgg ttcggcggat      900
gatcaatcgt ccggccagaa caatctgcaa tcccagatca tggatgtggt gaaggaggtc      960
gtccagatcc tgcagcagat gctggcggcg cagaacggcg gcagccagca gtccacctcg     1020
acgcagccga tgtaa                                                      1035
```

<210> SEQ ID NO 17
<211> LENGTH: 26
<212> TYPE: PRT
<213> ORGANISM: Xanthomonas campestris pv. glycines

<400> SEQUENCE: 17

```
Thr Leu Ile